US009687679B2

(12) United States Patent
Iwata et al.

(10) Patent No.: US 9,687,679 B2
(45) Date of Patent: Jun. 27, 2017

(54) PARTICLE BEAM THERAPY SYSTEM

(71) Applicant: MITSUBISHI ELECTRIC CORPORATION, Chiyoda-ku, Tokyo (JP)

(72) Inventors: Takaaki Iwata, Tokyo (JP); Hisashi Harada, Tokyo (JP); Masahiro Ikeda, Tokyo (JP); Yuehu Pu, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 0 days.

(21) Appl. No.: 14/903,177

(22) PCT Filed: Nov. 21, 2013

(86) PCT No.: PCT/JP2013/081386
§ 371 (c)(1),
(2) Date: Jan. 6, 2016

(87) PCT Pub. No.: WO2015/075797
PCT Pub. Date: May 28, 2015

(65) Prior Publication Data
US 2016/0136461 A1 May 19, 2016

(51) Int. Cl.
*A61N 5/10* (2006.01)
*G21K 5/04* (2006.01)

(52) U.S. Cl.
CPC .......... *A61N 5/1079* (2013.01); *A61N 5/1067* (2013.01); *A61N 5/1068* (2013.01);
(Continued)

(58) Field of Classification Search
CPC ...... A61N 5/10; A61N 5/1049; A61N 5/1077; A61N 5/1064; A61N 5/1067; A61N 5/107;
(Continued)

(56) References Cited

U.S. PATENT DOCUMENTS 7,525,104 B2 * 4/2009 Harada .................... A61N 5/10
  250/396 R
8,481,979 B2 * 7/2013 Iwata .................... A61N 5/1068
  250/492.1
(Continued)

FOREIGN PATENT DOCUMENTS

JP    2012-024254 A    2/2012
WO    WO 2012/032632 A1    3/2012

OTHER PUBLICATIONS

International Search Report (PCT/ISA/210) issued on Feb. 18, 2014, by the Japanese Patent Office as the International Searching Authority for International Application No. PCT/JP2013/081386.
(Continued)

*Primary Examiner* — David A Vanore
(74) *Attorney, Agent, or Firm* — Buchanan Ingersoll & Rooney PC

(57) ABSTRACT

In the particle beam therapy system, a beam transport system includes a beam-path changer for changing a beam path so as to transport a charged particle beam to any one of the plurality of particle beam irradiation apparatuses; and a treatment management device includes a beam-path controller that generates an emitter control signal for controlling an emitter of an accelerator and a beam-path changer control signal for controlling the beam-path changer so that, with respect to the plurality of particle beam irradiation apparatuses in which treatment is performed at the same treatment period of time, the charged particle beam is transported to each one of the plurality of particle beam irradiation apparatuses for each time period allocated thereto.

20 Claims, 41 Drawing Sheets

(52) U.S. Cl.
CPC ............... *A61N 2005/1074* (2013.01); *A61N 2005/1087* (2013.01)

(58) Field of Classification Search
CPC .. A61N 5/1079; A61N 5/1082; A61N 5/1039; A61N 5/1044; A61N 5/1048; A61N 5/1068; A61N 5/1081; A61N 5/103; A61N 5/1031; A61N 5/1037; A61N 5/1038; A61N 5/1042; A61N 5/1043; A61N 5/1045; A61N 5/1065; A61N 5/1069; A61N 5/1071; A61N 5/1075; A61N 5/1078; A61N 5/1084; G21K 5/04; G21K 1/093; G21K 1/087; A61B 6/03; A61B 6/037; A61B 6/4216; A61B 6/5235
USPC .......... 250/492.3, 492.1, 396 R, 398, 493.1, 250/503.1, 505.1; 600/407, 529, 1, 415, 600/425, 427, 534
See application file for complete search history.

(56) References Cited

U.S. PATENT DOCUMENTS

| | | | |
|---|---|---|---|
| 9,168,392 B1* | 10/2015 | Balakin | A61N 5/1049 |
| 2006/0118736 A1* | 6/2006 | Moriyama | A61N 5/10 |
| | | | 250/493.1 |
| 2007/0043286 A1* | 2/2007 | Lu | A61N 5/103 |
| | | | 600/407 |
| 2008/0258083 A1* | 10/2008 | Naumann | A61N 5/10 |
| | | | 250/492.3 |
| 2010/0006106 A1* | 1/2010 | Balakin | A61N 5/10 |
| | | | 128/845 |
| 2010/0207042 A1* | 8/2010 | Harada | A61N 5/1049 |
| | | | 250/492.3 |
| 2012/0061582 A1 | 3/2012 | Iwata | |
| 2013/0253253 A1 | 9/2013 | Iwata | |
| 2016/0250503 A1* | 9/2016 | Balakin | A61N 5/1077 |
| | | | 600/1 |
| 2016/0303399 A1* | 10/2016 | Balakin | A61N 5/1039 |
| 2016/0310764 A1* | 10/2016 | Bharadwaj | A61N 5/1078 |
| 2016/0332000 A1* | 11/2016 | Hale | G06T 15/04 |
| 2017/0014648 A1* | 1/2017 | Mostafavi | A61N 5/1069 |

OTHER PUBLICATIONS

Office Action (Examination Report) issued on Jul. 6, 2016, by the Taiwanese Intellectual Property Office in corresponding Taiwanese Patent Application No. 103122050, and an English Translation of the Office Action. (8 pages).

* cited by examiner

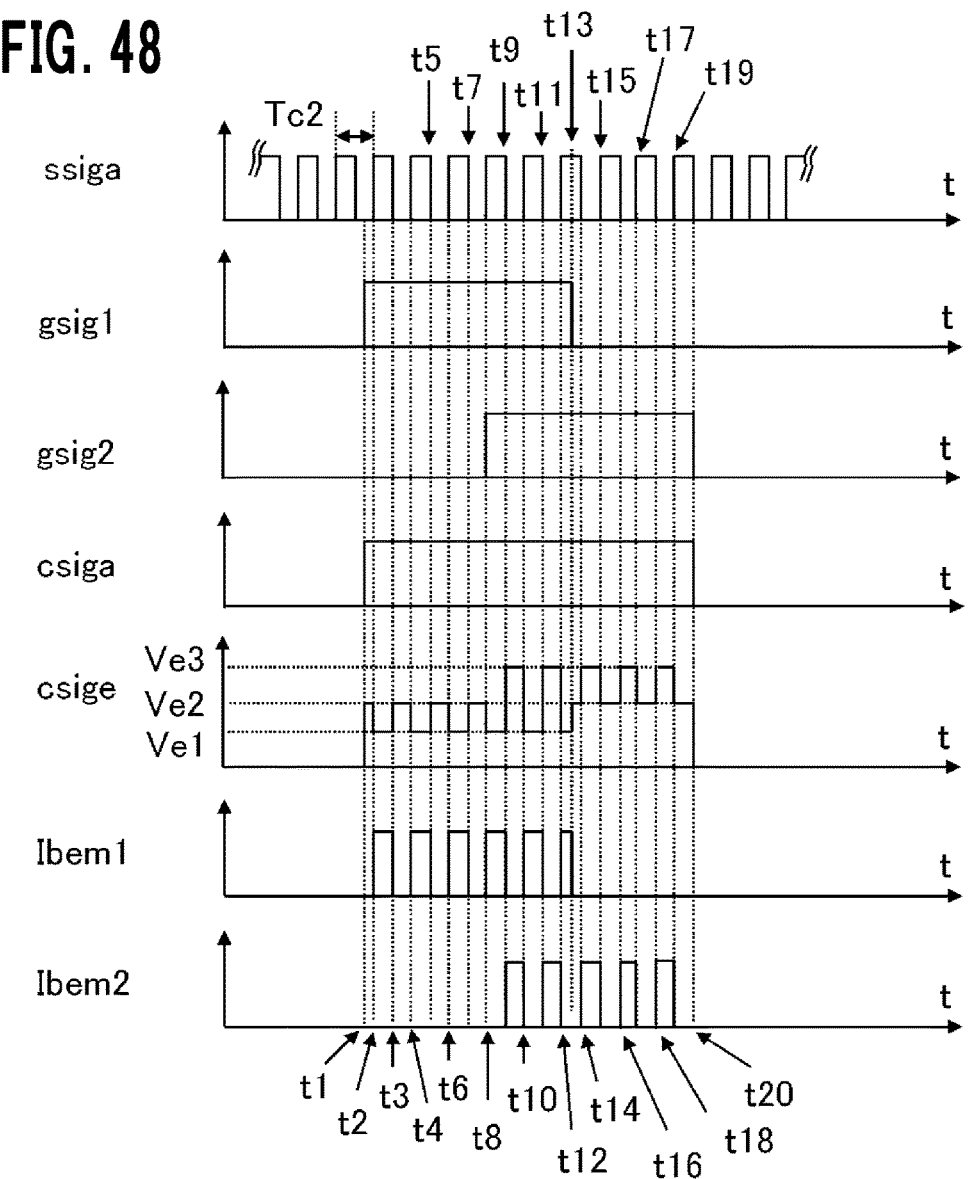

PARTICLE BEAM THERAPY SYSTEM

TECHNICAL FIELD

The present invention relates to a particle beam therapy system used for medical use or research use, and in particular, relates to a particle beam therapy system which can transport a beam to a plurality of treatment rooms as if simultaneously by time-sharing.

BACKGROUND ART

Heretofore, among particle beam therapy systems, there have been reported those with the presence of a plurality of treatment rooms. In such conventional particle beam therapy systems, beam paths are each configured to guide a beam to selected one of the treatment rooms by way of electromagnets of a beam transport system referred to as an HEBT (High Energy Beam Transport) system. Thus, it is basically unable to perform treatment simultaneously in the plurality of treatment rooms. Meanwhile, it is general to perform switching of the beam path by use of a bending magnet.

In Patent Document 1, there is described a particle beam therapy system that, for the purpose of improving throughput of the treatment in the case with the presence of a plurality of treatment rooms, performs treatment as if simultaneously in the plurality of treatment rooms, exceptionally by shifting respiratory phases of the patients in the respective treatment rooms from each other by way of respiratory navigation (breathing guidance).

CITATION LIST

Patent Document

Patent Document 1: International Patent Publication No. WO2012/032632A1 (Paragraph 0036 to Paragraph 0038, FIG. 1)

SUMMARY OF THE INVENTION

Problems to be Solved by the Invention

According to the particle beam therapy system of Patent Document 1, it is able to perform treatment as if simultaneously in the plurality of treatment rooms byway of respiratory navigation; however, because of the assumption that respiratory navigation has to be applied, it is unable to meet a demand for performing treatment simultaneously in the plurality of treatment rooms without using respiratory navigation.

This invention has been made to solve the problem as described above, and an object thereof is to provide a particle beam therapy system which can transport a beam to a plurality of treatment rooms as if simultaneously by time-sharing, even without using respiratory navigation.

Means for Solving the Problems

A particle beam therapy system of the invention comprises: a plurality of treatment rooms; a plurality of particle beam irradiation apparatuses placed respectively in the plurality of treatment rooms; an accelerator that accelerates a charged particle beam; a beam transport system that transports the charged particle beam accelerated by the accelerator to the plurality of particle beam irradiation apparatuses; and a treatment management device that controls the accelerator, the beam transport system and the plurality of particle beam irradiation apparatuses. It is characterized in that: the beam transport system includes a beam-path changer for changing a beam path so as to transport the charged particle beam to any one of the plurality of particle beam irradiation apparatuses; the treatment management device includes a beam-path controller that generates an emitter control signal for controlling an emitter of the accelerator and a beam-path changer control signal for controlling the beam-path changer so that, with respect to the plurality of particle beam irradiation apparatuses in which treatment is performed at a same treatment period of time, the charged particle beam is transported to each one of the plurality of particle beam irradiation apparatuses for each time period allocated thereto. And it is characterized in that with respect to a plurality of respiration gate signals for permitting radiation of the charged particle beam that are generated, from individual monitoring of respiratory states of a plurality of patients to be irradiated with the charged particle beam by the plurality of particle beam irradiation apparatuses, respectively for the plurality of patients, when at least two of them become simultaneously "ON", the beam-path controller generates the emitter control signal and the beam-path changer control signal so that the charged particle beam is transported, without depending on the plurality of respiratory gate signals, to the particle beam irradiation apparatus in the treatment room designated by a time-sharing signal for cyclically selecting each one of the plurality of particle beam irradiation apparatuses, on the basis of the plurality of respiratory gate signals and the time-sharing signal.

Effect of the Invention

According to the particle beam therapy system of the invention, the beam-path changer of the beam transport system and the emitter of the accelerator are controlled based on the plurality of respiratory gate signals and the time-sharing signal so that, with respect to the plurality of particle beam irradiation apparatuses in which treatment is performed at the same treatment period of time, the charged particle beam is transported to each one of the plurality of particle beam irradiation apparatuses for each time period allocated thereto. Thus, it is possible to transport the beam to the plurality of treatment rooms as if simultaneously by time-sharing, even without using respiratory navigation.

BRIEF DESCRIPTION OF THE DRAWINGS

FIG. 48 is a timing chart illustrating a beam distribution to a plurality of treatment rooms according to Embodiment 12 of the invention.

MODES FOR CARRYING OUT THE INVENTION

Embodiment 1

Figure 1:
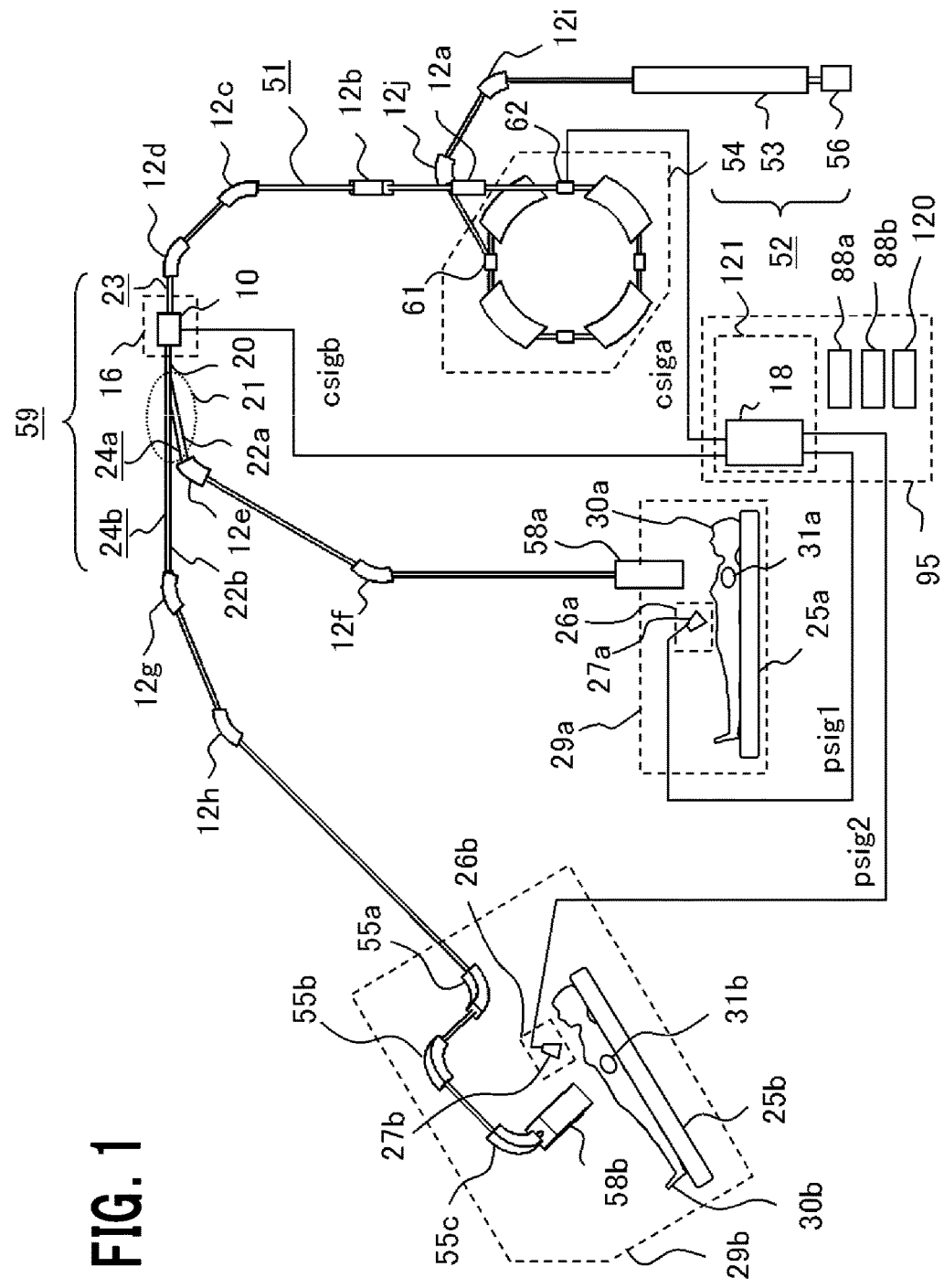
FIG. 1 is a configuration diagram showing a particle beam therapy system according to Embodiment 1 of the invention.
Figure 2:
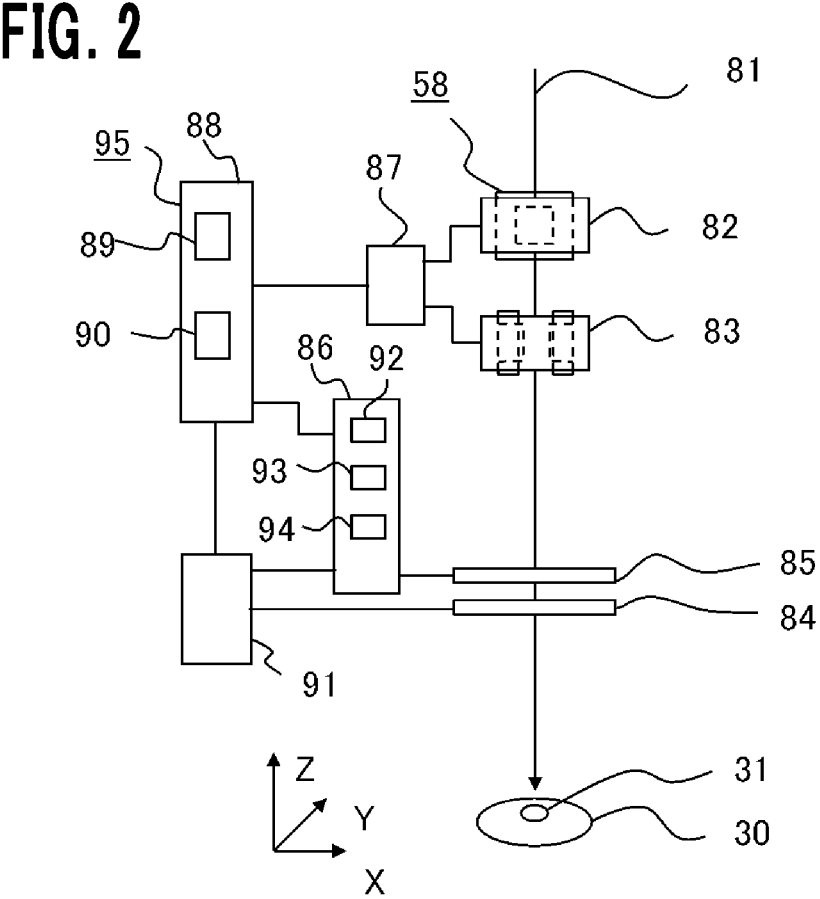
FIG. 2 is a schematic configuration diagram of a particle beam irradiation apparatus in FIG. 1.

FIG. 1 is a configuration diagram showing a particle beam therapy system according to Embodiment 1 of the invention. FIG. 2 is a schematic configuration diagram of a particle beam irradiation apparatus in FIG. 1. A particle beam therapy system 51 includes a beam generation apparatus 52, a beam transport system 59 and a plurality of particle beam irradiation apparatuses 58a, 58b. The particle beam irradiation apparatus 58b is placed in a rotary gantry (not shown) provided in a treatment room 29b. The particle beam irradiation apparatus 58a is placed in a treatment room 29a including no rotary gantry. Note that, in FIG. 1, for simplification's sake, description will be made assuming that the number of treatment rooms is two; however, this does not mean that the number of treatment rooms is limited to two in the invention.

The beam generation apparatus 52 includes an ion source 56, a linear accelerator 53 and a circular accelerator (hereinafter, referred to simply as "accelerator") 54 that is a synchrotron. The role of the beam transport system 59 is to communicate between the accelerator 54 and the particle beam irradiation apparatuses 58a, 58b. The beam transport system 59 includes: a beam-path changer 16 for changing a beam path directed toward each of the particle beam irradiation apparatuses 58a, 58b, of a charged particle beam 81

(see, FIG. 2) emitted from an emitter 62 of the accelerator 54; an upstream beam-transport system 23 that is from the emitter 62 of the accelerator 54 up to the beam-path changer 16; a downstream beam-transport system 24a that is from the beam-path changer 16 up to the particle beam irradiation apparatus 58a; and a downstream beam-transport system 24b that is from the beam-path changer 16 up to the particle beam irradiation apparatus 58b. The downstream beam-transport system 24b is partly placed in the rotary gantry (not shown) and includes, at that part, a plurality of bending magnets 55a, 55b and 55c. The beam generation apparatus 52, the beam transport system 59 and the particle beam irradiation apparatuses 58a, 58b are controlled in their cooperative manner by a treatment management device 95.

The charged particle beam 81 that is a particle beam, such as a proton beam, a carbon beam (heavy particle beam), etc., generated by the ion source 56, is accelerated by the linear accelerator 53 and entered into the accelerator 54 through an injector 61. The charged particle beam 81 is accelerated up to a given energy. In the accelerator 54, it is accelerated by a high-frequency electric field up to approx. 70 to 80% of the light velocity while being bent by magnets. The charged particle beam 81 emitted from the emitter 62 of the accelerator 54 is transported through the beam transport system 59 to the particle beam irradiation apparatuses 58a, 58b. In the beam transport system 59, the charged particle beam 81 having been sufficiently given with energy is guided to the particle beam irradiation apparatus 58a or 58b in the designated treatment room, through a passage formed of vacuum ducts (a main duct 20, a downstream duct 22a, a downstream duct 22b) in such a manner that its trajectory is changed as necessary by a plurality of bending magnets 12a to 12h. The particle beam irradiation apparatus 58a or 58b, while forming an irradiation field according to the size and depth of an diseased site that is an irradiation target 31 of a patient 30, radiates the charged particle beam 81 to the irradiation target 31 (see, FIG. 2). The charged particle beam 81 accelerated by the linear accelerator 53 is guided, while changing its trajectory by bending magnets 12i, 12j, to the injector 61 of the accelerator 54. The downstream duct 22a branched from the main duct 20 is connected to the particle beam irradiation apparatus 58a, and the downstream duct 22b branched from the main duct 20 is connected to the particle beam irradiation apparatus 58b. A portion indicated by a broken line circle is a duct branching section 21 in which the downstream ducts 22a, 22b are branched from the main duct 20.

Here, as is stated as "the designated treatment room", a particle beam therapy system generally includes a plurality of treatment rooms as described previously, from a viewpoint of treatment efficiency. Namely, it is necessary to provide the particle beam irradiation apparatuses 58 as many as the number of the treatment rooms. Generally, a large and complex system formed of such a plurality of sub-systems comprises sub-control devices for exclusively controlling the respective sub-systems and a main control device for supervising and controlling the entire system, in many cases. With respect also to the particle beam therapy system 51 shown in Embodiment 1 of the invention, description will be made citing a case where a configuration with a main control device and sub-control devices is applied. For simplification's sake, here, a sub-system including the beam generation apparatus 52 and the beam transport system 59 will be totally referred to as an acceleration system. The particle beam irradiation apparatus 58, or the particle beam irradiation apparatus 58 and the rotary gantry will be referred to as an irradiation system. The treatment management device 95 includes a main management device 120 for controlling the whole of the particle beam therapy system 51, an accelerator-system control device 121 for controlling the accelerator system, an irradiation management device 88a for controlling the particle beam irradiation apparatus 58a, and an irradiation management device 88b for controlling the particle beam irradiation apparatus 58b. The accelerator-system control device 121 includes a beam-path controller 18 for controlling the emitter 62 and the beam-path changer 16.

On a treatment table 25a in the treatment room 29a, a patient 30a is laid. In the treatment room 29a, there is placed a respiratory signal generator 26a for detecting a respiratory state of the patient 30a using a patient sensor 27a to thereby generate a respiratory signal psig1. On a treatment table 25b in the treatment room 29b, a patient 30b is laid. In the treatment room 29b, there is placed a respiratory signal generator 26b for detecting a respiratory state of the patient 30b using a patient sensor 27b to thereby generate a respiratory signal psig2. The diseased site of the patient 30a is an irradiation target 31a, and the diseased site of the patient 30b is an irradiation target 31b. For the particle beam irradiation apparatuses, numeral 58 is used collectively, and numerals 58a, 58b are used when they are to be described distinctively. With respect to the treatment rooms, the treatment tables, the patients, the irradiation targets, the patient sensors and the respiratory signal generators, numerals 29, 25, 30, 31, 27 and 26 are collectively used, respectively, and these numerals are each used as being suffixed with "a" or "b" when its corresponding objects are to be described distinctively.

In FIG. 2, the particle beam irradiation apparatus 58 includes: an X-direction scanning electromagnet 82 and a Y-direction scanning electromagnet 83 which scan the charged particle beam 81, respectively in an X-direction and a Y-direction that are directions perpendicular to the charged particle beam 81; a position monitor 84; a dose monitor 85; a dose-data converter 86; a beam-data processing device 91; and a scanning-electromagnet power source 87. The irradiation management device 88 for controlling particle beam irradiation apparatus 58 in the treatment management device 95 includes an irradiation control computer 89 and an irradiation control device 90. The dose-data converter 86 includes a trigger generator 92, a spot counter 93 and an inter-spot counter 94. Note that in FIG. 2, the travelling direction of the charged particle beam 81 is a direction of −Z.

The X-direction scanning electromagnet 82 is a scanning electromagnet for scanning the charged particle beam 81 in the X-direction, and the Y-direction scanning electromagnet 83 is a scanning electromagnet for scanning the charged particle beam 81 in the Y-direction. With respect to the charged particle beam 81 scanned by the X-direction scanning electromagnet 82 and the Y-direction scanning electromagnet 83, the position monitor 84 detects beam information for calculating a passing position (gravity center position) and a size of the beam that passes therethrough. The beam-data processing device 91 calculates the passing position (gravity center position) and the size of the charged particle beam 81 on the basis of the beam information that comprises a plurality of analog signals detected by the position monitor 84. Further, the beam-data processing device 91 generates an abnormality detection signal indicative of a position abnormality and/or a size abnormality of the charged particle beam 81, and outputs the abnormality detection signal to the irradiation management device 88.

The dose monitor 85 detects the dose of the charged particle beam 81. The irradiation management device 88 controls the irradiation position of the charged particle beam 81 in the irradiation target 31 of the patient 30 on the basis of treatment plan data prepared by an unshown treatment plan device, and moves the charged particle beam 81 to a next irradiation position when the dose having been measured by the dose monitor 85 and converted by the dose-data converter 86 into digital data, reaches a desired dose. The scanning-electromagnet power source 87 changes setup currents for the X-direction scanning electromagnet 82 and the Y-direction scanning electromagnet 83 on the basis of control inputs (commands) outputted from the irradiation management device 88 for the X-direction scanning electromagnet 82 and the Y-direction scanning electromagnet 83.

Here, the scanning irradiation method of the particle beam irradiation apparatus 58 is assumed to be a raster-scanning irradiation method in which the charged particle beam 81 is not stopped when the irradiation position of the charged particle beam 81 is changed, and in which the beam irradiation position moves between spot positions successively like a spot-scanning irradiation method. The spot counter 93 serves to measure an irradiation dose during when the beam irradiation position of the charged particle beam 81 is staying. The inter-spot counter 94 serves to measure an irradiation dose during when the beam irradiation position of the charged particle beam 81 is moving. The trigger generator 92 serves to generate a dose completion signal when the dose of the charged particle beam 81 at a beam irradiation position reaches the desired irradiation dose.

Figure 3:
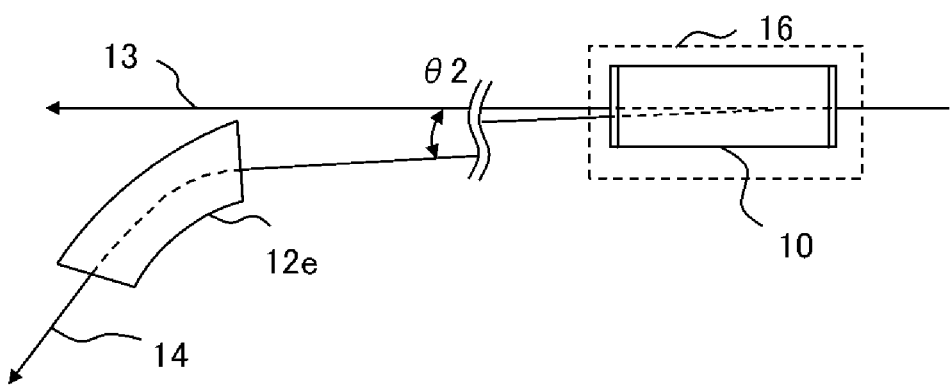
FIG. 3 is a schematic diagram illustrating a main part in a beam transport system in FIG. 1.
Figure 4:
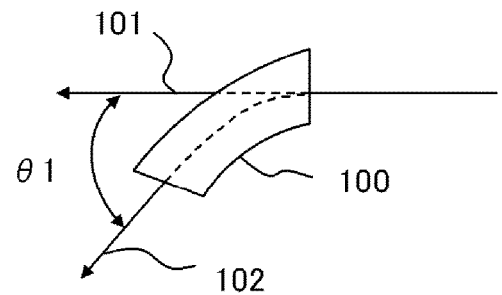
FIG. 4 is a schematic diagram illustrating a main part in a beam transport system in Comparative Example.

The abstract of beam-path switching in the particle beam therapy system 51 of Embodiment 1 will be described in comparison with the particle beam therapy system of Patent Document 1 (Comparative Example). FIG. 3 is a schematic diagram illustrating a main part in the beam transport system in FIG. 1, and FIG. 4 is a schematic diagram illustrating a main part in a beam transport system in Comparative Example. In Comparative Example, switching is made using a bending magnet 100 between a charged particle beam 101 and a charged particle beam 102. In contrast, the particle beam therapy system 51 of Embodiment 1 differs from that of Comparative Example in using the beam-path changer 16 whose deflection angle is smaller than the deflection angle θ1 of the bending magnet 100 but whose switching speed is faster than the switching speed of the bending magnet. The beam-path changer 16 of Embodiment 1 is a kicker electromagnet 10. From the kicker electromagnet 10 as a beginning point, the beam path is branched into two paths. At a position that is sufficiently and linearly downstream in the beam traveling direction from the kicker electromagnet 10, there is placed the bending magnet 12e for guiding the beam path to the treatment room 29. A charged particle beam 13 is a beam traveling linearly from the kicker electromagnet 10. A charged particle beam 14 is a beam that is entered by the kicker electromagnet 10 into the bending magnet 12e by a deflection angle of θ2 relative to the charged particle beam 13, and then guided to the treatment room 29a.

In a particle beam therapy, it is wanted to give a dose according to a treatment plan to a diseased site that is the irradiation target 31, and to avoid unwanted radiation to the surrounding normal tissues as much as possible. Thus, respiratory gated irradiation is performed, in particular, in the case where the irradiation target 31 is such a site that moves with the breathing of the patient 30. More specifically, it is generally said that the movement of an organ due to breathing becomes most steady in a breathing-out state; thus, for the patient 30, his/her abdominal region or the like is subjected to measurement using a patient sensor 27, such as a laser displacement meter, etc., to thereby perform monitoring of his/her breathing state in real-time. As shown in FIG. 1, the respiratory signals psig1 and psig2, that are signals measured by the patient sensors 27 and each indicative of a breathing state, are inputted to the beam-path controller 18 that controls the emitter 62 and the beam-path changer 16.

Figure 6:
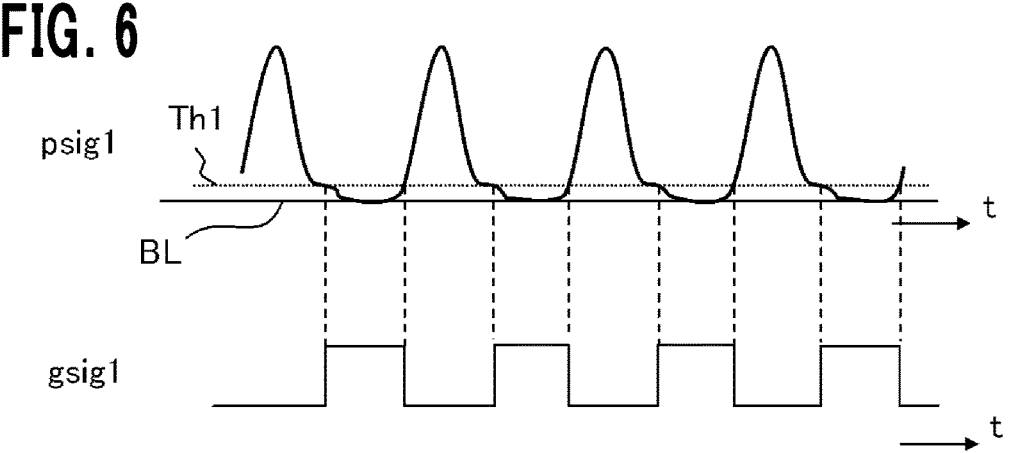
FIG. 6 is a diagram illustrating a respiratory signal and a respiratory gate signal of the invention.

A shown in FIG. 6, when the respiratory signal psig1 falls below a predetermined certain threshold value Th1, namely, in the case where it is determined to be in a breathing-out state, a respiratory gate signal gsig1 for permitting radiation becomes "ON". When the respiratory gate signal gsig1 is "ON", the beam-path controller 18 controls the emitter 62, so that the charged particle beam 81 is emitted. FIG. 6 is a diagram illustrating the respiratory signal and the respiratory gate signal of the invention. In FIG. 6, a relationship between the respiratory signal psig1 and the respiratory gate signal gsig1 is shown. Shown at the upper side is the respiratory signal psig1 and at the under side is the respiratory gate signal gsig1. The abscissa represents time t, and the ordinate represents a signal value of the respiratory signal psig1 or the respiratory gate signal gsig1. In the figure, indicated by BL is a base line of the respiratory signal psig1. Note that, in FIG. 6, the "ON" state of the respiratory gate signal gsig1 for permitting radiation is represented as a signal-value H state (high signal-value state). The relationship between the respiratory signal psig2 and the respiratory gate signal gsig2 is also similar to in FIG. 6, so that, when the respiratory signal psig2 falls below a predetermined certain threshold value Th2, namely, in the case where it is determined to be in a breathing-out state, a respiratory gate signal gsig2 for permitting radiation becomes "ON".

The accelerator-system control device 121 in the treatment management device 95 controls the accelerator 54 and the beam transport system 59 so that, with respect to the plurality of particle beam irradiation apparatuses 58 in which treatment is performed at the same treatment period of time, the charged particle beam 81 is transported to each one of the plurality of particle beam irradiation apparatuses 58 for each time period allocated thereto. In the case where the charged particle beam 81 is to be transported to only one of the plurality of treatment rooms 29a, 29b, the beam-path controller 18 in the accelerator-system control device 121 causes the beam-path changer 16 to switch the beam path to the corresponding one and then not to change the beam path until the irradiation treatment by the charged particle beam 81 is completed.

Figure 5:
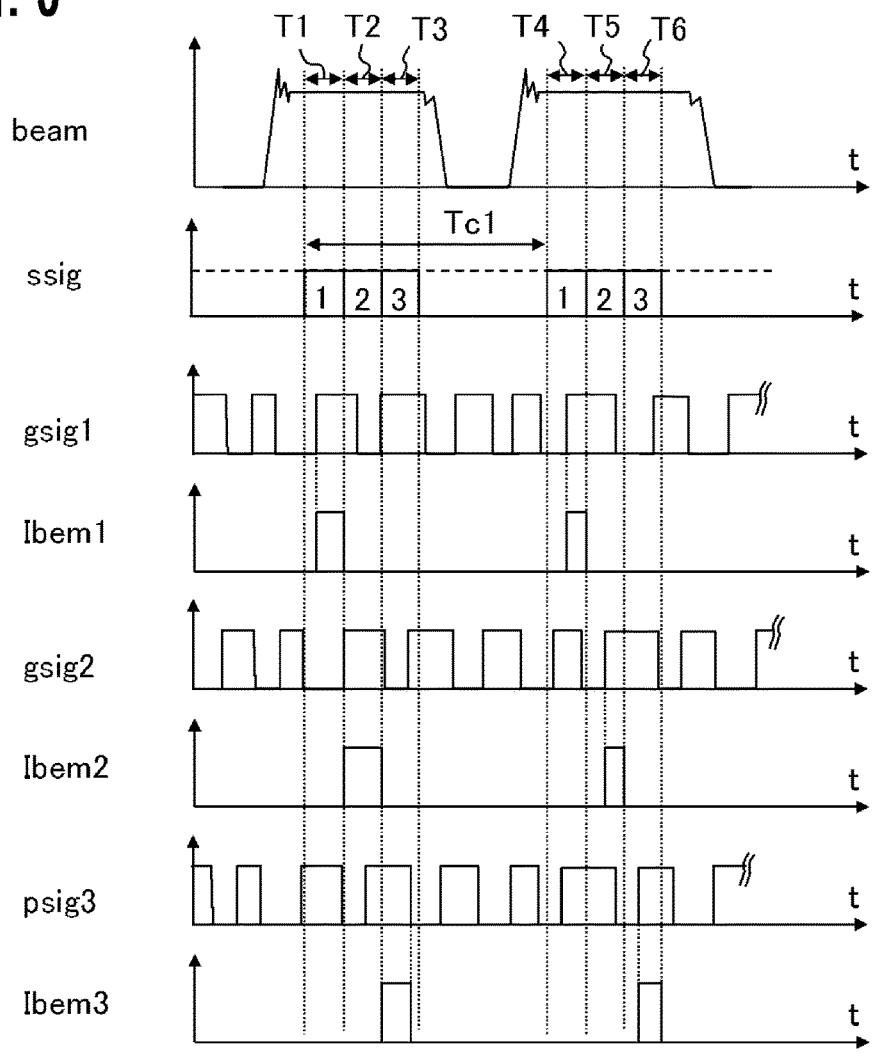
FIG. 5 is a timing chart illustrating a beam distribution to a plurality of treatment rooms according to the particle beam therapy system of Embodiment 1 of the invention.

Next, description will be made about the case where irradiation treatment is performed in the plurality of treatment rooms 29a, 29b, etc. in the same period of time, namely, about the case where requests for radiation of the charged particle beam 81 to the plurality of treatment rooms 29a, 29b, etc. are overlapping. FIG. 5 is a timing chart illustrating a beam distribution to the plurality of treatment rooms according to the particle beam therapy system of Embodiment 1 of the invention. In FIG. 5, there are illustrated: a beam waveform in the accelerator 54; a time-sharing signal ssig; the respiratory gate signal gsig1; an irradiation current Ibem1 for the treatment room 29a (treatment room 1); the respiratory gate signal gsig2; an irradiation current Ibem2 for the treatment room 29b (treatment room 2); a respiratory gate signal gsig3; and an irradiation current Ibem3 for another treatment room (treatment room 3). The time-share signal ssig is a predetermined cyclic signal for the beam-path changer 16, which is a signal for designating one from the plurality of treatment rooms 29 (particle beam irradiation apparatuses 58 in the plurality of treatment rooms). Specific example of the time-share signal ssig will be described later. The respiratory gate signal gsig3 is a respiratory gate signal for permitting radiation to the other treatment room (treatment room 3). The abscissa represents time t, and the uppermost ordinate for "Beam" represents energy. Each ordinate for the time-sharing signal ssig and the respiratory gate signals gsig1, gsig2, gsig3, represents a signal value of each of these signals, and each ordinate for the irradiation currents Ibem1, Ibem2, Ibem3 represents a current value.

According to the invention, in the plurality of treatment rooms 29, the respective patients 30 are each subjected to monitoring of his/her breathing state. FIG. 5 shows distribution examples of the charged particle beam 81 in the three treatment rooms, and thus, for each treatment room designated by the time-sharing signal ssig and when the respiratory gate signal for that treatment room becomes "ON", the particle beam therapy system 51 of the invention transports the charged particle beam 81 time-divisionally to that treatment room so as to radiate the charged particle beam 81 to the patient in that treatment room for a specified time to thereby supply the irradiation current Ibem to him/her. For the irradiation currents, a symbol of Ibem is used collectively, and the symbol is used as being suffixed with a number, such as Ibem1, Ibem2, Ibem3 or the like, when they are to be described distinctively.

In the beam shown uppermost in FIG. 5, the charged particles are accelerated to provide a flat-top form (a highly-energized stable state of the beam with the energy of a predetermined value), and are decelerated thereafter. In this manner, in the accelerator 54, the charged particles repeatedly fall in an under-acceleration state, a flat-top state, an under-deceleration state and a low-energy state. In the periods T1 and T4 where the time-sharing signal ssig designates the treatment room 1, when the respiratory gate signal gsig1 is "ON", it is controlled so that the charged particle beam 81 is emitted from the emitter 62 of the accelerator 54 and the beam-path changer 16 guides the charged particle beam 81 to the treatment room 1. By such controlling, in each of the periods T1, T4, the irradiation current Ibem1 is supplied to the irradiation target 31 of the patient 30.

In the periods T2 and T5 where the time-sharing signal ssig designates the treatment room 2, when the respiratory gate signal gsig2 is "ON", it is controlled so that the charged particle beam 81 is emitted from the emitter 62 of the accelerator 54 and the beam-path changer 16 guides the charged particle beam 81 to the treatment room 2. By such controlling, in each of the periods T2, T5, the irradiation current Ibem2 is supplied to the irradiation target 31 of the patient 30. Likewise, in the periods T3 and T6 where the time-sharing signal ssig designates the treatment room 3, when the respiratory gate signal gsig3 is "ON", it is controlled so that the charged particle beam 81 is emitted from the emitter 62 of the accelerator 54 and the beam-path changer 16 guides the charged particle beam 81 to the treatment room 3. By such controlling, in each of the periods T3, T6, the irradiation current Ibem3 is supplied to the irradiation target 31 of the patient 30.

Figure 7:
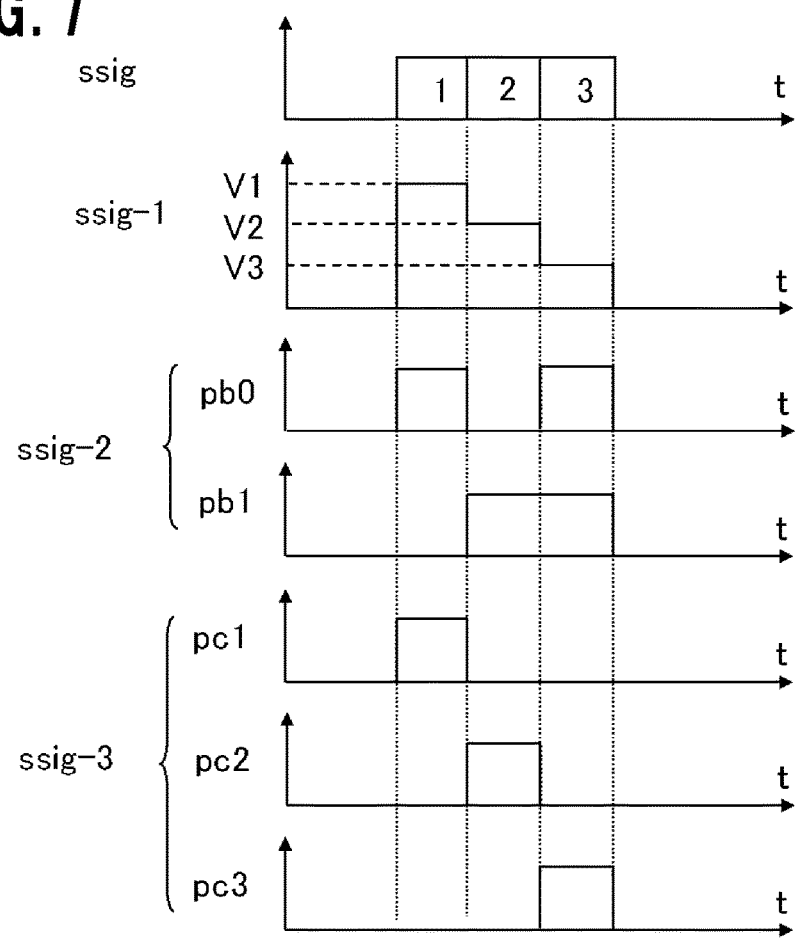
FIG. 7 is a diagram illustrating a time-sharing signal of the invention.

FIG. 7 is a diagram illustrating the time-sharing signal of the invention. In FIG. 7, there are shown three examples, namely, three time-sharing signals of ssig-1, ssig-2 and ssig-3. The time-sharing signal ssig-1 is exemplified for the case of selecting each treatment room depending on a voltage-value difference in a single signal. For example, the treatment room 1, the treatment room 2 and the treatment room 3 are selected when the voltage values of the time-sharing signal ssig-1 are V1, V2 and V3, respectively. The time-sharing signal ssig-2 is exemplified for the case of selecting each treatment room depending on a combination of voltage values of two signals pb0 and pb1. For example, when the voltage value of the signal pb0 is at a high level and the voltage value of the signal pb1 is at a low level, the treatment room 1 is selected. When the voltage value of the signal pb0 is at a low level and the voltage value of the signal pb1 is at a high level, the treatment room 2 is selected. When the voltage value of the signal pb0 is at a high level and the voltage value of the signal pb1 is at a high level, the treatment room 3 is selected. The time-sharing signal ssig-3 is exemplified for the case of selecting each treatment room depending on a combination of voltage values of three signals pc1, pc2 and pc3. For example, when the voltage values of the signals pc1, pc2 and pc3 are at a high level, a low level, and a low level, respectively, the treatment room 1 is selected. When the voltage values of the signals pc1, pc2 and pc3 are at a low level, a high level, and a low level, respectively, the treatment room 2 is selected. When the voltage values of the signals pc1, pc2 and pc3 are at a low level, a low level, and a high level, respectively, the treatment room 3 is selected.

Figure 8:
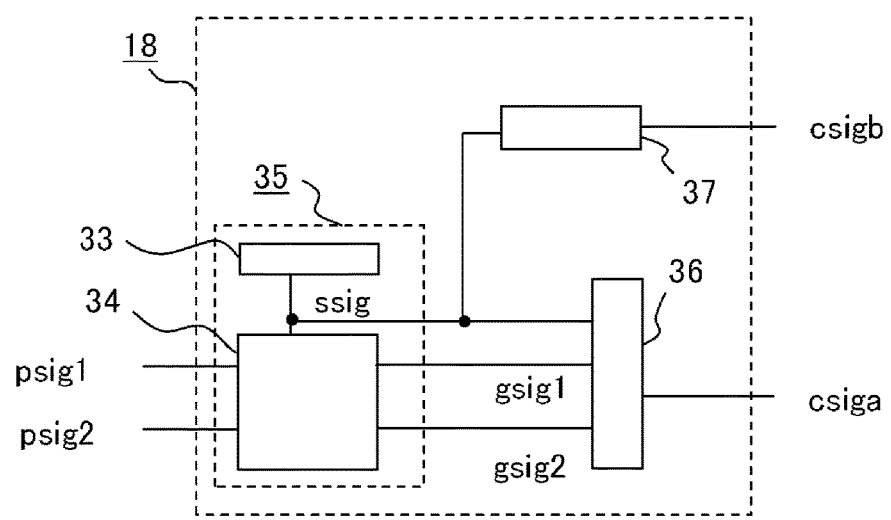
FIG. 8 is a diagram showing a beam-path controller in FIG. 1.
Figure 9:
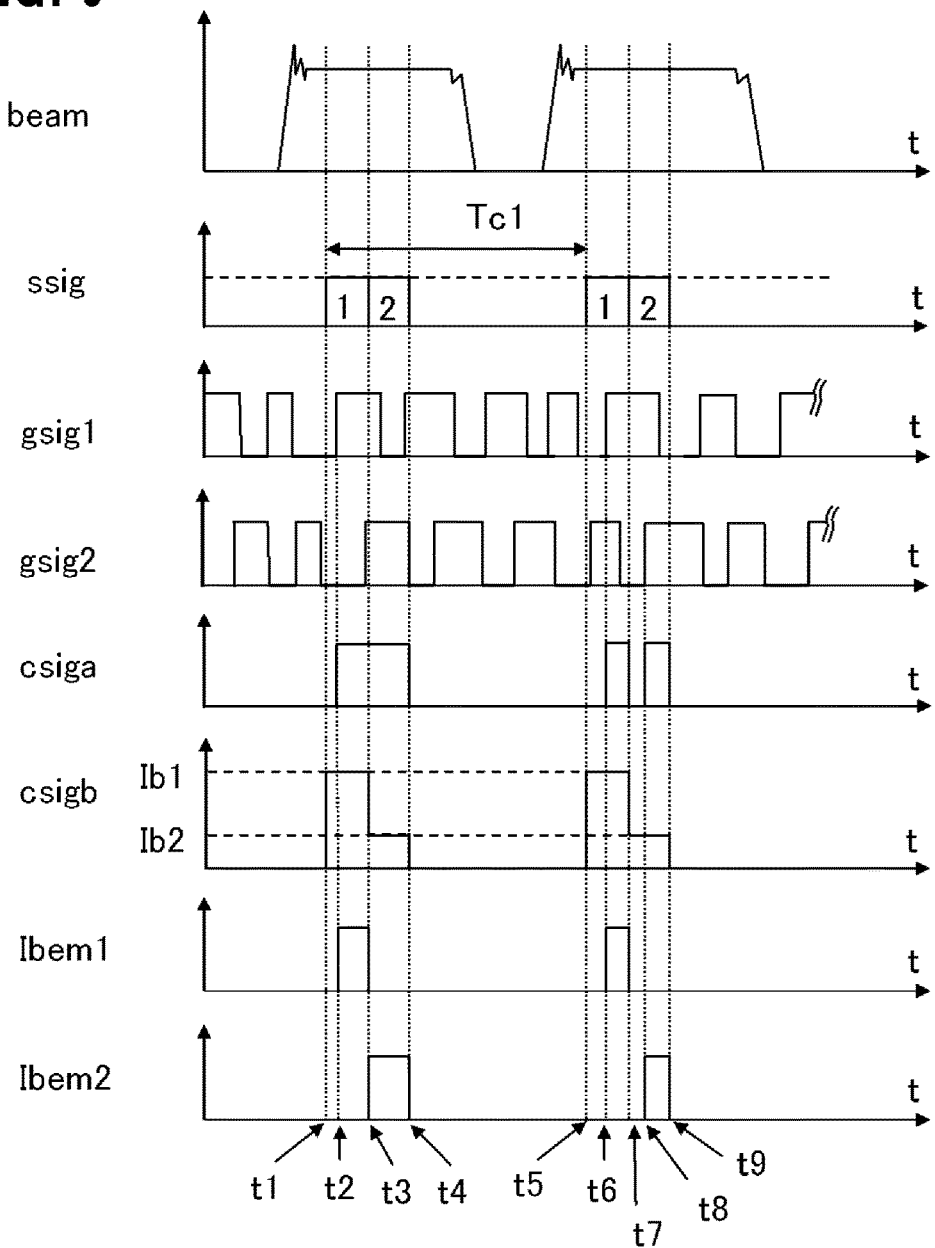
FIG. 9 is a timing chart illustrating a beam distribution to a plurality of treatment rooms according to Embodiment 1 of the invention.

The beam-path controller 18 will be described in detail. FIG. 8 is a diagram showing the beam-path controller in FIG. 1, and FIG. 9 is a timing chart illustrating a beam distribution to the plurality of treatment rooms according to Embodiment 1 of the invention. In FIG. 9, the abscissa represents time t. Each ordinate for the time-sharing signal ssig, the respiratory gate signals gsig1, gsig2, an emitter control signal csiga, and a kicker control signal csigb represents a signal value of each of these signals, and each ordinate for the irradiation currents Ibem1, Ibem2 represents a current value. The beam-path controller 18 includes: a time-sharing signal generator 33 for generating the time-sharing signal ssig; a respiratory gate-signal generator 34 for generating the respiratory gate signals gsig1, gsig2; an emitter control-signal generator 36 for generating the emitter control signal csiga; and a kicker control-signal generator (beam-path changer control-signal generator) 37 for generating the kicker control signal csigb that is a beam-path changer control signal. The time-sharing signal generator 33 and the respiratory gate-signal generator 34 constitute a control signal generator 35.

The time-sharing signal generator 33 generates the time-sharing signal ssig that corresponds to the treatment rooms in which irradiation treatment is performed in the same period of time. In FIG. 9, there is shown a case where irradiation treatment is performed in the two treatment rooms 29a, 29b in the same period of time. The time-sharing signal ssig is a cyclic signal and in FIG. 9, its one cycle is from the time t1 to the time t5. The cycle of the time-sharing signal ssig is Tc1. The time-sharing signal ssig shown in FIG. 9 is a signal that, in the first cyclic period, selects the treatment room 1 during the time t1 to the time t3 and selects the treatment room 2 during the time t3 to the time t4. In the second cyclic period, the time-sharing signal ssig is a signal that selects the treatment room 1 during the time t5 to the time t7 and selects the treatment room 2 during the time t7 to the time t9. The cycle Tc1 of the time-sharing signal ssig and an increase/decrease cycle in energy of the charged particle beam 81 in the accelerator 54, are controlled to be nearly matched to each other by the accelerator-system control device 121. The accelerator 54 is controlled so that the flat-top state is established at least in a period (from t1 to t4, and from t5 to t9) where the charged particle beam 81 is distributed to the plurality of treatment rooms.

A distribution time for each of the treatment room 1 and the treatment room 2 may be determined arbitrarily. When the total irradiation time for a patient in the treatment room 1 and that for a patient in the treatment room 2 are largely different to each other, it suffices to make longer the distribution time for the patient with the longer total irradiation time. When the total irradiation time for the patient 30a in the treatment room 29a (treatment room 1) is longer than the total irradiation time for the patient 30b in the treatment room 29b (treatment room 2), it suffices to make the distribution time (t3–t1) for the treatment room 1 longer than the distribution time (t4–t3) for the treatment room 2. In this manner, the distribution time for the treatment room 1 is varied according to the total irradiation time for the patient, so that, even though the energy is required to be changed at the time of slice change, if each hit rate is nearly equal, each irradiation completion time for the plurality of treatment rooms can be matched to each other. Thus, it is possible to efficiently utilize the charged particle beam 81 without wastefully shutting off the charged particle beam 81.

The respiratory gate-signal generator 34 generates the respiratory gate signal gsig1 from the respiratory signal psig1 transmitted from the respiratory signal generator 26a, and generates the respiratory gate signal gsig2 from the respiratory signal psig2 transmitted from the respiratory signal generator 26b. How to generate the respiratory gate signals gsig1, gsig2 is just as described previously. The emitter control-signal generator 36 receives the respiratory gate signals gsig1, gsig2 to thereby generate the emitter control signal csiga as follows. In FIG. 9, when the time-sharing signal ssig designates the treatment room 1 and the respiratory gate signal gsig1 for the treatment room 1 is "ON" (signal-value H state), the emitter control-signal generator 36 outputs an emission command (signal-value H state) for ordering the emitter 62 to emit the charged particle beam 81. Further, when the time-sharing signal ssig designates the treatment room 2 and the respiratory gate signal gsig2 for the treatment room 2 is "ON" (signal-value H state), the emitter control-signal generator 36 outputs an emission command (signal-value H state) for ordering the emitter 62 to emit the charged particle beam 81. The emitter control-signal generator 36, when the condition for outputting the emission command becomes unsatisfied, places the emitter control signal csiga in an emission stopped state and outputs an emission stop command (signal-value L state) for ordering the emitter 62 to stop emission of the charged particle beam 81. In FIG. 9, a period from the time t2 to the time t4 in the first cyclic period, and periods from the time t6 to the time t7 and from the time t8 to the time t9 in the second cyclic period are the periods where the emission command of the charged particle beam 81 is outputted.

The kicker control-signal generator 37 receives the time-sharing signal ssig to thereby generate the kicker control signal csigb as follows. In FIG. 9, when the time-sharing signal ssig designates the treatment room 1, the kicker control-signal generator 37 outputs a path-1 command (signal-value Ib1 state) for ordering switching of the path so that the charged particle beam 81 is guided to the treatment room 1 (treatment room 29a). When the time-sharing signal ssig designates the treatment room 2, the kicker control-signal generator 37 outputs a path-2 command (signal-value Ib2 state) for ordering switching of the path so that the charged particle beam 81 is guided to the treatment room 2 (treatment room 29b). The kicker control-signal generator 37 outputs, in the case of the path-1 command, a control current of the signal value Ib1 to the kicker electromagnet 10, and outputs, in the case of the path-2 command, a control current of the signal value Ib2 to the kicker electromagnet 10. Note that, in FIG. 9, such a case is shown where, when the time-sharing signal ssig does not designate anyone of the treatment rooms (neither the treatment room 1 nor the treatment room 2), the signal value of the kicker control signal csigb is at a signal level of other than Ib1 and also other than Ib2, for example, at zero level.

During the time t2 to the time t3 in the first cyclic period, the emitter control signal csiga provides the emission command (signal-value H state) and the kicker control signal csigb provides the path-1 command (signal-value Ib1 state), so that, in the particle beam therapy system 51 of Embodiment 1, the charged particle beam 81 is emitted and the irradiation current Ibem1 is supplied to the irradiation target 31a of the patient 30a in the treatment room 1 (treatment room 29a). During the time t3 to the time t4, the emitter control signal csiga provides the emission command (signal-value H state) and the kicker control signal csigb provides the path-2 command (signal-value Ib2 state), so that, in the particle beam therapy system 51 of Embodiment 1, the charged particle beam 81 is emitted and the irradiation current Ibem2 is supplied to the irradiation target 31b of the patient 30b in the treatment room 2 (treatment room 29b).

During the time t6 to the time t7 in the second cyclic period, the emitter control signal csiga provides the emission command (signal-value H state) and the kicker control signal csigb provides the path-1 command (signal-value Ib1 state), so that, in the particle beam therapy system 51 of Embodiment 1, the charged particle beam 81 is emitted and the irradiation current Ibem1 is supplied to the irradiation target 31a of the patient 30a in the treatment room 1 (treatment room 29a). During the time t8 to the time t9, the emitter control signal csiga provides the emission command (signal-value H state) and the kicker control signal csigb provides the path-2 command (signal-value Ib2 state), so that, in the particle beam therapy system 51 of Embodiment 1, the charged particle beam 81 is emitted and the irradiation current Ibem2 is supplied to the irradiation target 31b of the patient 30b in the treatment room 2 (treatment room 29b).

According to the particle beam therapy system 51 of Embodiment 1, the beam path is switched using the beam-path changer 16 whose deflection angle is smaller than that of the bending magnet 100 but whose switching speed is faster than that of the bending magnet. Thus, unlike the conventional one, it is possible to transport the beam to the plurality of treatment rooms 29 as if simultaneously by time-sharing, even without using respiratory navigation. According to the particle beam therapy system 51 of Embodiment 1, it is not required to perform respiratory navigation, so that a patient can be subjected to a particle beam therapy in a relaxed state specific to the patient. According to the particle beam therapy system 51 of Embodiment 1, since a respiratory cycle is not forcibly induced by respiratory navigation, the patient feels relief and thus can promptly enter his/her respiration stable state. This makes it possible to reduce the occupation time of the treatment room, to thereby improve throughput of the treatment as compared with the conventional case.

According to particle beam therapy system 51 of Embodiment 1, since a patient can be subjected to a particle beam therapy in a relaxed state specific to the patient, the breathing-out state of the patient in one respiration cycle can be made longer than the conventional case, and thus, it is possible to make longer a time period where each of the respiratory gate signals gsig1, gsig2 is made "ON". When the time period where each of the respiratory gate signals gsig1, gsig2 is made "ON" becomes longer, the number of irradiation interruption processes of the charged particle beam in one irradiation treatment becomes reduced, so that an irradiation time period where the charged particle beam 81 is intermittently radiated, namely, the irradiation time period from the start of irradiation to the completion of irradiation, can be reduced. This makes it possible to reduce the occupation time of the treatment room 29a, 29b, to thereby improve throughput of the treatment as compared with the conventional case.

It should be noted that the respiratory gate signal (gsig1, gsig2, gsig3 or the like) may be generated by a device other than the beam-path controller 18, and if this is the case, such a configuration may be applied in which an externally-generated respiratory gate signal is inputted to the beam-path controller 18. The same applies to other embodiments to be described later.

The particle beam therapy system 51 of Embodiment 1 comprises: the plurality of treatment rooms 29; the plurality of particle beam irradiation apparatuses 58 placed respectively in the plurality of treatment rooms 29; the accelerator 54 that accelerates the charged particle beam 81; the beam transport system 59 that transports the charged particle beam 81 accelerated by the accelerator 54 to the plurality of particle beam irradiation apparatuses 58; and the treatment management device 95 that controls the accelerator 54, the beam transport system 59 and the plurality of particle beam irradiation apparatuses 58. According to the particle beam therapy system 51 of Embodiment 1, it is characterized in that: the beam transport system 59 includes the beam-path changer 16 for changing a beam path so as to transport the charged particle beam 81 to any one of the plurality of particle beam irradiation apparatuses 58; the treatment management device 95 includes the beam-path controller 18 that generates the emitter control signal csiga for controlling the emitter 62 of the accelerator 54 and the beam-path changer control signal (kicker control signal csigb) for controlling the beam-path changer 16 so that, with respect to the plurality of particle beam irradiation apparatuses 58 in which treatment is performed at the same treatment period of time, the charged particle beam 81 is transported to each one of the plurality of particle beam irradiation apparatuses 58 for each time period allocated thereto; and the beam-path controller 18 generates the emitter control signal csiga and the beam-path changer control signal (kicker control signal csigb) on the basis of: the plurality of respiration gate signals gsig1, gsig2 for permitting radiation of the charged particle beam 81 that are generated, from individual monitoring of respiratory states of the plurality of patients 30 to be irradiated with the charged particle beam 81 by the plurality of particle beam irradiation apparatuses 58, respectively for the plurality of patients 30; and the time-sharing signal ssig for cyclically selecting each one of the plurality of particle beam irradiation apparatuses 58. Thus, it is possible to transport the beam to the plurality of treatment rooms 29 as if simultaneously by time-sharing, even without using respiratory navigation.

Embodiment 2

Figure 10:
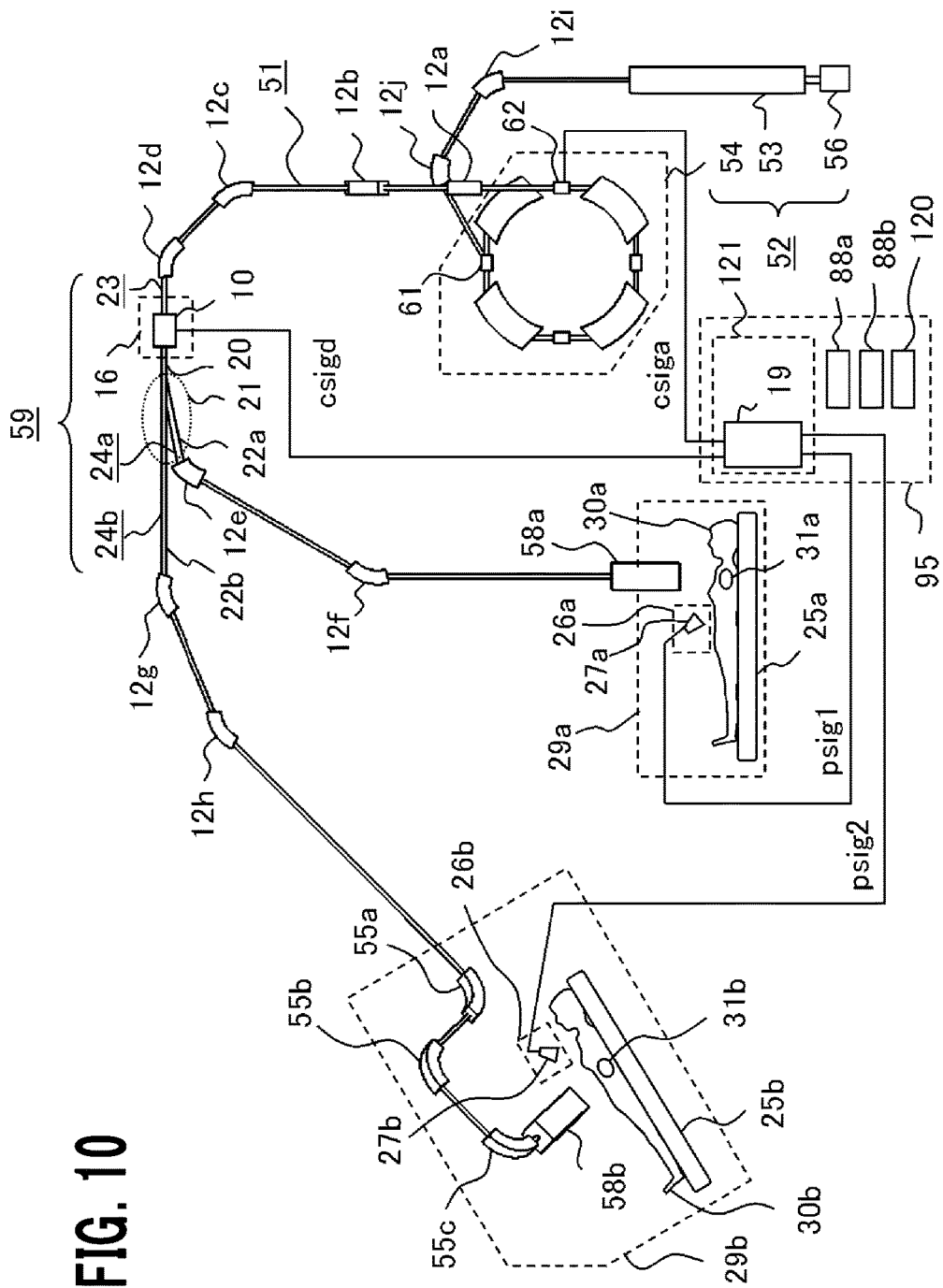
FIG. 10 is a configuration diagram showing a particle beam therapy system according to Embodiment 2 of the invention.
Figure 11:
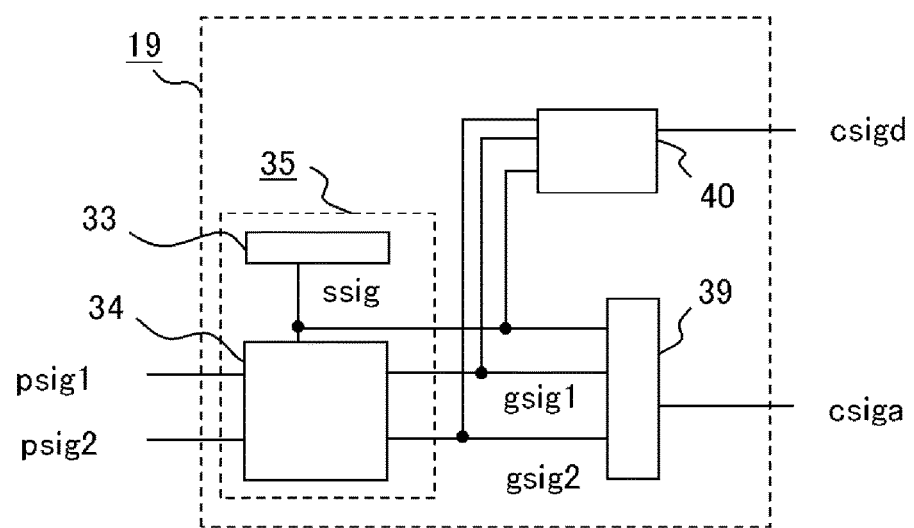
FIG. 11 is a diagram showing a beam-path controller in FIG. 10.
Figure 12:
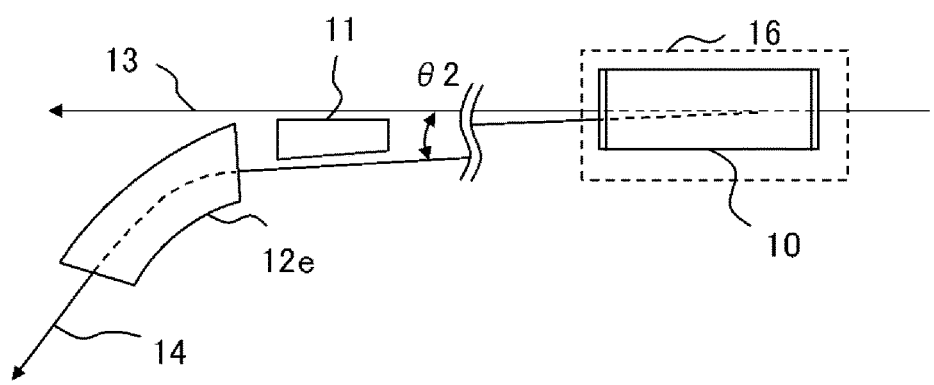
FIG. 12 is a diagram showing a damper placed near a duct branching point in FIG. 10.
Figure 13:
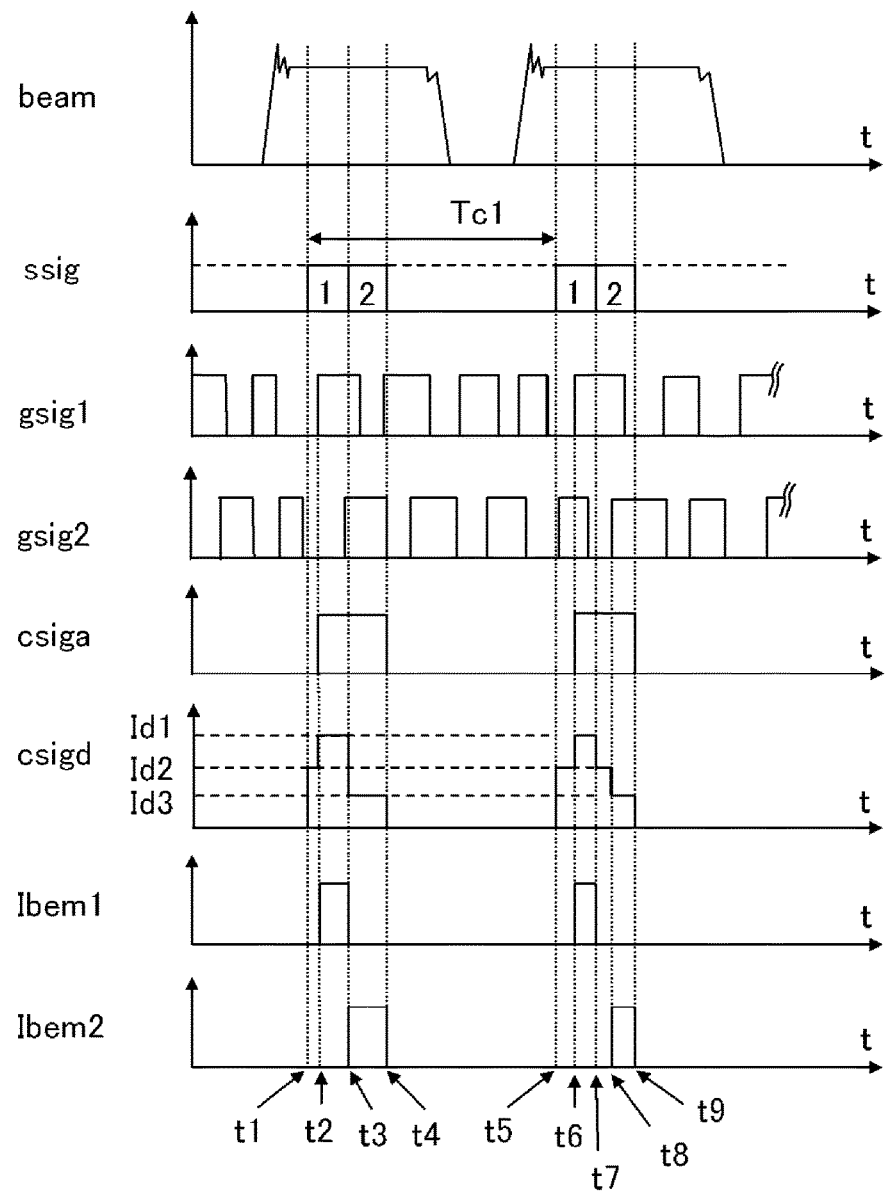
FIG. 13 is a timing chart illustrating a beam distribution to a plurality of treatment rooms according to Embodiment 2 of the invention.

FIG. 10 is a configuration diagram showing a particle beam therapy system according to Embodiment 2 of the invention, and FIG. 11 is a diagram showing a beam-path controller in FIG. 10. FIG. 12 is a diagram showing a damper placed near a duct branching point in FIG. 10, and FIG. 13 is a timing chart illustrating a beam distribution to a plurality of treatment rooms according to Embodiment 2 of the invention. The particle beam therapy system 51 of Embodiment 2 differs from the particle beam therapy system 51 of Embodiment 1 in that a damper 11 for shutting off the charged particle beam 81 is provided in a duct branching section 21 placed at the downstream side of the beam-path changer 16, and in that the treatment management device 95 includes a beam-path controller 19 for outputting to the beam-path changer 16, a kicker control signal csigd that is a beam-path changer control signal. The beam-path controller 19 includes, in place of the emitter control-signal generator 36 and the kicker control-signal generator 37 in Embodiment 1, an emitter control-signal generator 39 for generating an emitter control signal csiga and a kicker control-signal generator (beam-path changer control-signal generator) 40. The kicker control-signal generator 40 receives the respiratory gate signals gsig1, gsig2 and the time-sharing signal ssig to thereby output the kicker control signal csigd generated therein. The emitter control-signal generator 39 receives the respiratory gate signals gsig1, gsig2 and the time-sharing signal ssig to thereby generate the emitter control signal csiga corresponding to the kicker control signal csigd, and outputs it to the emitter 62.

Operations of the particle beam therapy system 51 of Embodiment 2 will be described using FIG. 13. Description will be made about part of operations which differs from Embodiment 1. The emitter control-signal generator 39 receives the respiratory gate signals gsig1, gsig2 and the time-sharing signal ssig, to thereby generate the emitter control signal csiga as follows. In each cyclic period of the time-sharing signal ssig, when the time-sharing signal ssig designates the treatment room 1 that is the first treatment room and the respiratory gate signal gsig1 for the treatment room 1 is "ON" (signal-value H state), the emitter control-signal generator 39 outputs an emission command (signal-value H state) for ordering the emitter 62 to emit the charged particle beam 81. The emitter control signal csiga, once becomes in an emission-ordering state, maintains the emission-ordering state until the designation of the treatment room 2 that corresponds to the last treatment room is removed in the time-sharing signal ssig. Namely, when the designation of the treatment room 2 that corresponds to the last treatment room is removed in the time-sharing signal ssig, the emitter control-signal generator 39 places the emitter control signal csiga in an emission stopped state and outputs an emission stop command (signal-value L state) for ordering the emitter 62 to stop emission of the charged particle beam 81. In FIG. 13, a period from the time t2 to the time t4 in the first cyclic period, and a period from the time t6 to the time t9 in the second cyclic period are the periods where the emission command of the charged particle beam 81 is outputted.

The kicker control-signal generator 40 receives the respiratory gate signals gsig1, gsig2 and the time-sharing signal ssig to thereby generate the kicker control signal csigd as follows. In FIG. 13, when the time-sharing signal ssig designates the treatment room 1 and the respiratory gate signal gsig1 is "ON", the kicker control-signal generator 40 outputs a path-1 command (signal-value Id1 state) for ordering switching of the path so that the charged particle beam 81 is guided to the treatment room 1 (treatment room 29a). When the time-sharing signal ssig designates the treatment room 2 and the respiratory gate signal gsig2 is "ON", the kicker control-signal generator 40 outputs a path-2 command (signal-value Id3 state) for ordering switching of the path so that the charged particle beam 81 is guided to the treatment room 2 (treatment room 29b). When the time-sharing signal ssig designates either one of the treatment rooms (treatment room 1, treatment room 2) and the respiratory gate signal corresponding to that treatment room (gsig1, gsig2) is "OFF", the kicker control-signal generator 40 outputs a path-3 command (signal-value Id2 state) for ordering switching of the path so that the charged particle beam 81 is guided to the damper 11. The path-3 command differs from the path command for transporting the charged particle beam 81 to the designated treatment room 29 in the plurality of treatment rooms 29, and can be also said to be a path shutoff command for shutting off the transportation of the charged particle beam 81 to the plurality of treatment rooms 29.

The kicker control-signal generator 40 outputs, in the case of the path-1 command, a control current of the signal value Id1 to the kicker electromagnet 10, outputs, in the case of the path-2 command, a control current of the signal value Id3 to the kicker electromagnet 10, and outputs, in the case of the path-3 command, a control signal of the signal value Id2 to the kicker electromagnet 10. Note that, in FIG. 13, such a case is shown where, when the time-sharing signal ssig does not designate anyone of the treatment rooms (neither the treatment room 1 nor the treatment room 2), the signal value of the kicker control signal csigd is at a signal level of other than Id1, Id2 and Id3, for example, at zero level.

During the time t2 to the time t3 in the first cyclic period, the emitter control signal csiga provides the emission command (signal-value H state) and the kicker control signal csigd provides the path-1 command (signal-value Id1 state), so that, in the particle beam therapy system 51 of Embodiment 2, the charged particle beam 81 is emitted and the irradiation current Ibem1 is supplied to the irradiation target 31a of the patient 30a in the treatment room 1 (treatment room 29a). During the time t3 to the time t4, the emitter control signal csiga provides the emission command (signal-value H state) and the kicker control signal csigd provides the path-2 command (signal-value Id3 state), so that, in the particle beam therapy system 51 of Embodiment 2, the charged particle beam 81 is emitted and the irradiation current Ibem2 is supplied to the irradiation target 31b of the patient 30b in the treatment room 2 (treatment room 29b). During the time t1 to the time t2, the emitter control signal csiga provides the emission stop command (signal-value L state), so that, in the particle beam therapy system 51 of Embodiment 2, the charged particle beam 81 is not emitted.

During the time t6 to the time t7 in the second cyclic period, the emitter control signal csiga provides the emission command (signal-value H state) and the kicker control signal csigd provides the path-1 command (signal-value Id1 state), so that, in the particle beam therapy system 51 of Embodiment 2, the charged particle beam 81 is emitted and the irradiation current Ibem1 is supplied to the irradiation target 31a of the patient 30a in the treatment room 1 (treatment room 29a). During the time t8 to the time t9, the emitter control signal csiga provides the emission command (signal-value H state) and the kicker control signal csigd provides the path-2 command (signal-value Id3 state), so that, in the particle beam therapy system 51 of Embodiment 2, the charged particle beam 81 is emitted and the irradiation current Ibem2 is supplied to the irradiation target 31b of the patient 30b in the treatment room 2 (treatment room 29b). During the time t5 to the time t6, the emitter control signal csiga provides the emission stop command (signal-value L state), so that, in the particle beam therapy system 51 of Embodiment 2, the charged particle beam 81 is not emitted. During the time t7 to the time t8, although the emitter control signal csiga provides the emission command (signal-value H state), the kicker control signal csigd provides the path-3 command (signal-value Id2 state), so that, in the particle beam therapy system 51 of Embodiment 2, the charged particle beam 81 is shut off by the damper 11.

Figure 14:
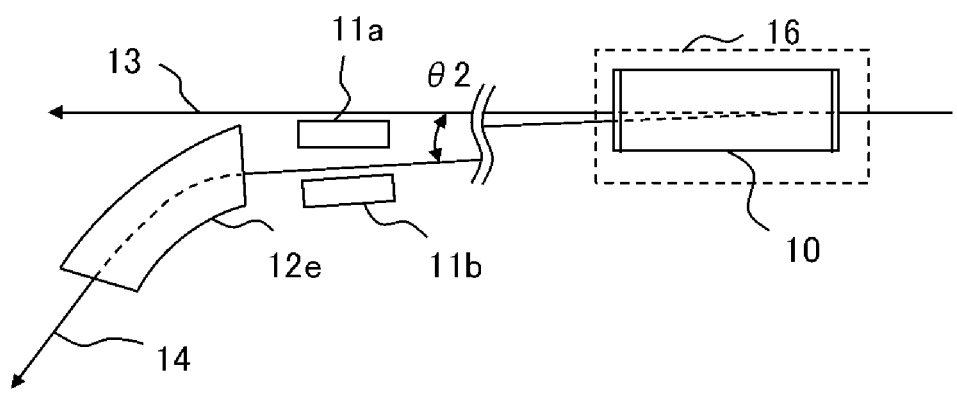
FIG. 14 is a diagram showing other dampers placed near a duct branching point in FIG. 10.

Note that in FIG. 13, such a case is shown where, during the time t1 to the time t2 and the time t5 to the time t6, the kicker control signal csigd provides the path-3 command (signal-value Id2 state); however, the kicker control signal csigd may be in another signal-value state, such as the signal-value Id1 state, the signal-value Id3 state or the like, because the emitter control signal csiga provides the emission stop command (signal-value L state) during the time t1 to the time t2 and the time t5 to the time t6. Further, the description has been made using the case where the damper 11 for shutting off the charged particle beam 81, which is single, is provided in the duct branching section 21 placed at the downstream side of the beam-path changer 16; however, as shown in FIG. 14, dampers 11a, 11b may be provided individually for each downstream beam-transport system. FIG. 14 is a diagram showing other dampers placed near a duct branching point in FIG. 10.

The particle beam therapy system 51 of Embodiment 2 achieves the same effect as in Embodiment 1. The particle beam therapy system 51 of Embodiment 2 includes the damper 11 or the dampers 11a, 11b, wherein in each cyclic period of the time-sharing signal ssig, the emitter control signal csiga, once becomes in an emission-ordering state, maintains the emission-ordering state until the designation of the treatment room 2 that corresponds to the last treatment room is removed in the time-sharing signal ssig, and wherein, when the charged particle beam 81 is to be shut off in the middle of the emission-ordering state, it is shut off by the damper 11, 11a or 11b. Thus, it is possible to shut off the charged particle beam 81 more rapidly than in Embodiment 1, so that the irradiation current with a time width shorter than that in Embodiment 1 can be supplied to the irradiation target 31 of the patient 30.

Embodiment 3

Figure 15:
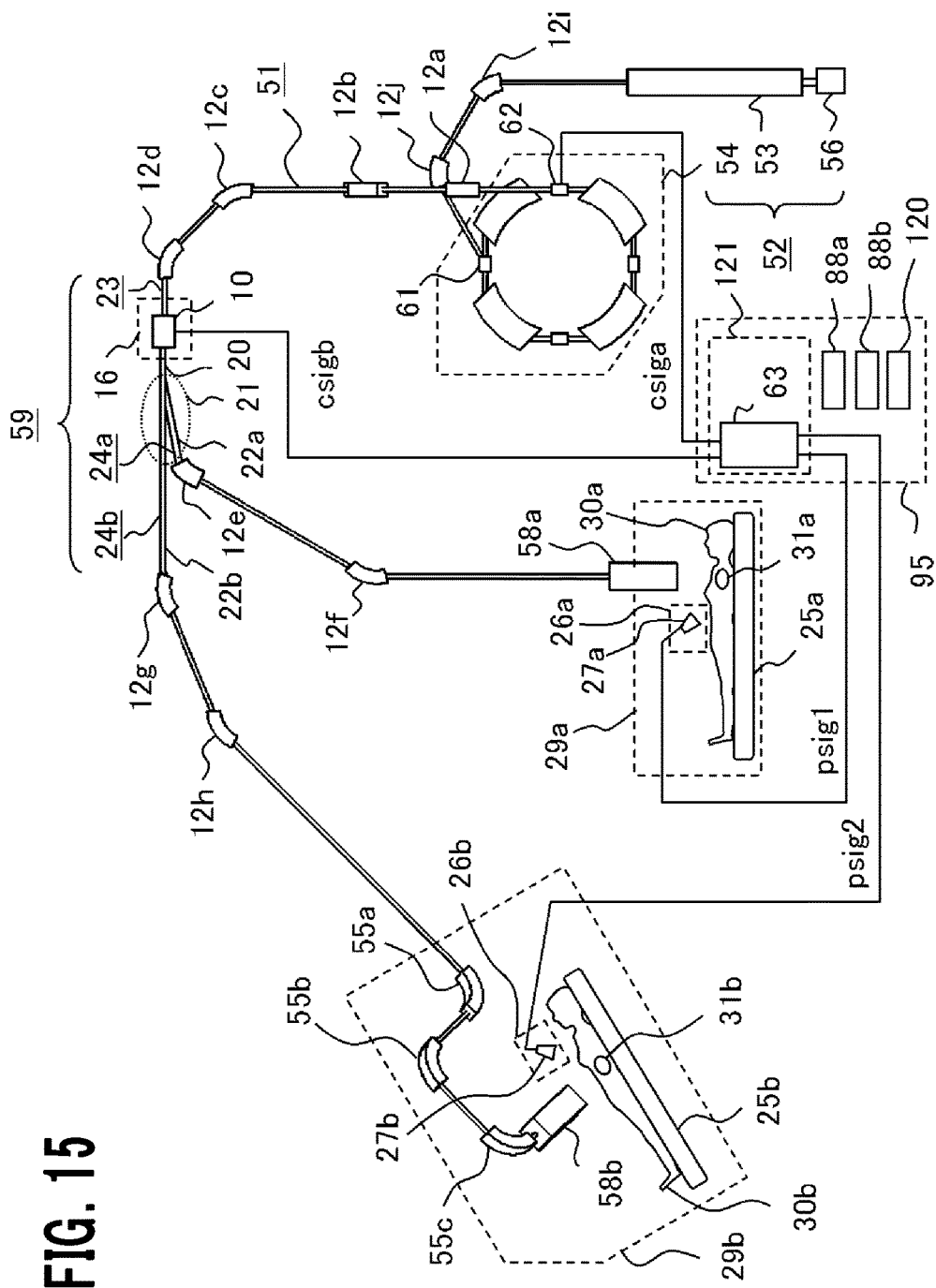
FIG. 15 is a configuration diagram showing a particle beam therapy system according to Embodiment 3 of the invention.
Figure 16:
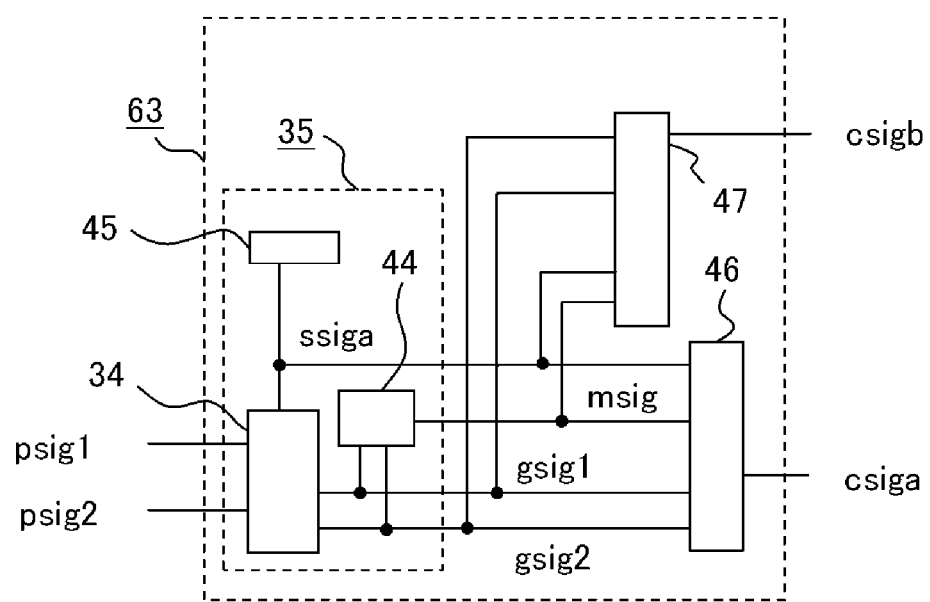
FIG. 16 is a diagram showing a beam-path controller in FIG. 15.
Figure 17:
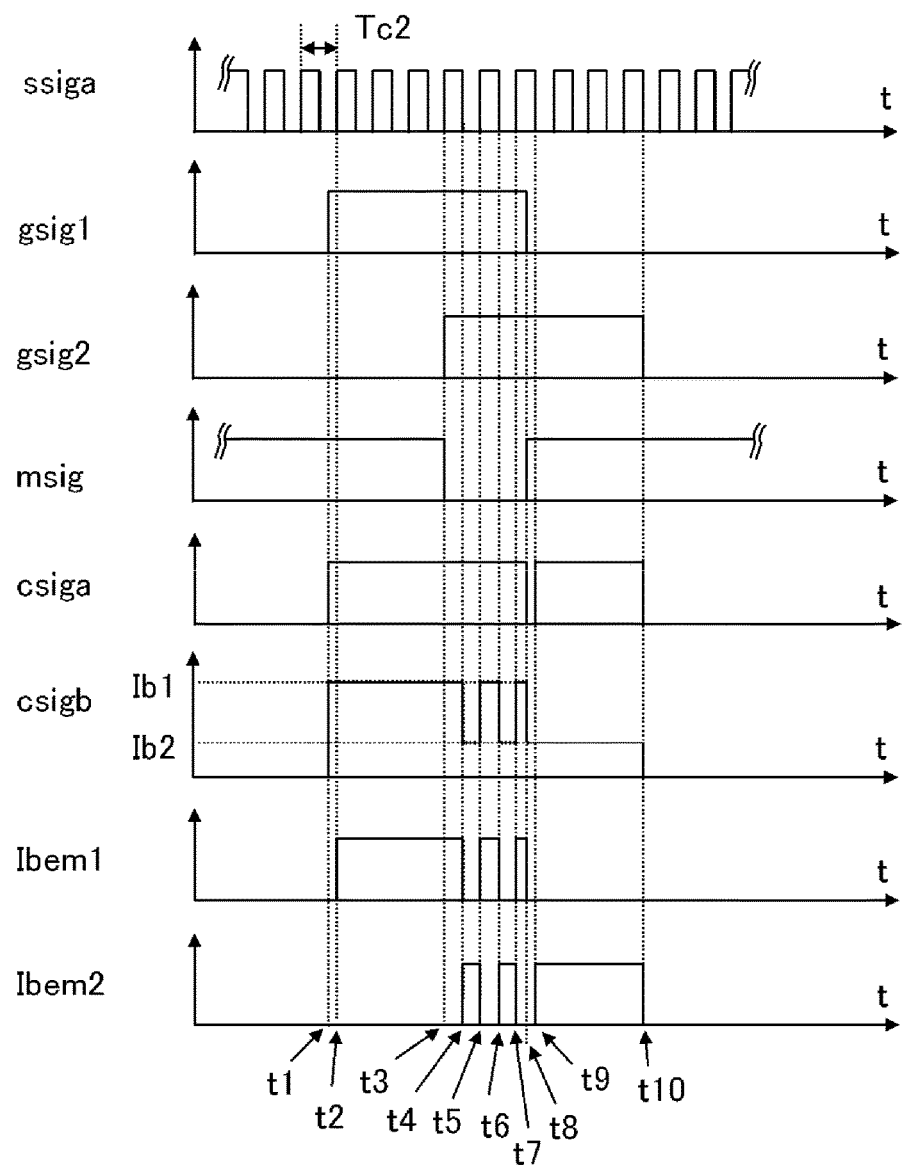
FIG. 17 is a timing chart illustrating a beam distribution to a plurality of treatment rooms according to Embodiment 3 of the invention.

FIG. 15 is a configuration diagram showing a particle beam therapy system according to Embodiment 3 of the invention, and FIG. 16 is a diagram showing a beam-path controller in FIG. 15. FIG. 17 is a timing chart illustrating a beam distribution to a plurality of treatment rooms according to Embodiment 3 of the invention. When irradiation requests from the plurality of treatment rooms 29 are overlapping, for example, when the respiratory gate signal gsig1 for the treatment room 1 is in "ON" state and the respiratory gate signal gsig2 for the treatment room 2 is in "ON" state, the particle beam therapy system 51 of Embodiment 3 controls so as to make switching of the charged particle beam 81 between toward the respective corresponding treatment rooms 1, 2 (treatment rooms 29a, 29b) in a short time, as shown below.

The treatment management device 95 in Embodiment 3 differs from that in Embodiment 1 in including a beam-path controller 63 that outputs a kicker control signal csigb whose signal value varies in a time period shorter than in Embodiment 1. The beam-path controller 63 includes: an emitter control-signal generator 46 for generating the emitter control signal csiga; a kicker control-signal generator (beam-path changer control-signal generator) 47 for generating the kicker control signal csigb; and a control signal generator 35 for outputting a plurality of control signals to the emitter control-signal generator 46 and the kicker control-signal generator 47. The control signal generator 35 includes: a time-sharing signal generator 45 for generating a time-sharing signal ssiga with a cycle of Tc2 that is shorter than that in Embodiment 1; a respiratory gate-signal generator 34 for generating the respiratory gate signals gsig1, gsig2; and a mask signal generator 44 for generating a mask signal msig for masking a treatment-room selection by the time-sharing signal ssiga. The time-sharing signal ssiga has the cycle Tc2 that causes the treatment-room designation to change two or more times in a period where the respiratory gate signals gsig1 and gsig2 keep "ON" states.

Operations of the particle beam therapy system 51 of Embodiment 3 will be described using FIG. 17. In FIG. 17, the abscissa represents time t. Each ordinate for the time-sharing signal ssiga, the respiratory gate signals gsig1, gsig2, the mask signal msig, the emitter control signal csiga, and the kicker control signal csigb represents a signal value of each of these signals, and each ordinate for the irradiation currents Ibem1, Ibem2 represents a current value. Note that, in order not to complicate the figure, illustrated here is a case where the time-sharing signal ssiga selects the treatment room 1 and the treatment room 2 at its H level and L level, respectively. When the time-sharing signal ssiga is at H level, the treatment room 1 is designated, and when the time-sharing signal ssiga is at L level, the treatment room 2 is designated. Note that the time-sharing signal ssiga can be constituted in a form of the time-sharing signals ssig-1, ssig-2 and ssig-3 shown in FIG. 7.

As shown in FIG. 17, the time-sharing signal generator 45 generates the time-sharing signal ssiga with the cycle Tc2 that is shorter than the cycle Tc1 in Embodiment 1. The mask signal generator 44 receives the respiratory gate signals gsig1, gsig2, to thereby generate the mask signal msig. The mask signal msig is, for example when its output signal value is in H state, a masking command for masking (for making ineffective) a treatment-room selection by the time-sharing signal ssiga. The mask signal msig is, when its output signal value is in L state, a mask cancelling command for making effective a treatment-room selection by the time-sharing signal ssiga. The mask signal generator 44 outputs the mask signal msig as the mask cancelling command when at least two respiratory gate signals in the plurality of respiratory gate signals, are "ON" simultaneously. The mask signal generator 44 outputs the mask signal msig as the masking command when there is no plural respiratory gate signals being simultaneously "ON", namely, when all of the respiratory gate signals are "OFF" or only one of the respiratory gate signals is "ON".

The respiratory gate signal gsig1 is "ON" during the time t1 to the time t8, and the respiratory gate signal gsig2 is "ON" during the time t3 to the time t10, so that the mask signal generator 44 outputs the mask signal msig as the masking command (signal-value H state) in a time period from the time t3 to the time t8 (Period A), and outputs the mask signal msig as the mask cancelling command (signal-value L state) during other than the time period of Period A.

The emitter control-signal generator 46 receives the respiratory gate signals gsig1, gsig2, the time-sharing signal ssiga and the mask signal msig, to thereby generate the emitter control signal csiga as follows. First of all, with respect to the emission command (signal-value H state) for ordering the emitter 62 to emit the charged particle beam 81, the following three cases arise. When the mask signal msig provides the masking command (signal-value H state) and one of the respiratory gate signals (respiratory gate signal gsig1 or respiratory gate signal gsig2) is "ON" (signal-value H state) (First Case), the emitter control-signal generator 46 outputs the emission command (signal-value H state) for ordering the emitter 62 to emit the charged particle beam 81. When the mask signal msig provides the mask canceling command (signal-value L state), the time-sharing signal ssiga designates the treatment room 1, and the respiratory gate signal gsig1 for the treatment room 1 is "ON" (signal-value H state) (Second Case), the emitter control-signal generator 46 outputs the emission command (signal-value H state) for ordering the emitter 62 to emit the charged particle beam 81. When the mask signal msig provides the mask canceling command (signal-value L state), the time-sharing signal ssiga designates the treatment room 2, and the respiratory gate signal gsig2 for the treatment room 2 is "ON" (signal-value H state) (Third Case), the emitter control-signal generator 46 outputs the emission command (signal-value H state) for ordering the emitter 62 to emit the charged particle beam 81. In other than the above three cases, the emitter control-signal generator 46 outputs an emission stop command (signal-value L state) for ordering the emitter 62 to stop emission of the charged particle beam 81. In FIG. 17, the period from the time t1 to the time t8 and the period from the time t9 to the time t10, are each a period where the emission command of the charged particle beam 81 is outputted.

The kicker control-signal generator 47 receives the respiratory gate signals gsig1, gsig2, the time-sharing signal ssiga and the mask signal msig, to thereby generate the kicker control signal csigb as follows. In FIG. 17, when the mask signal msig provides the masking command (signal-value H state) and the respiratory gate signal gsig1 is "ON" (signal-value H state), the kicker control-signal generator 47 outputs a path-1 command (signal-value Ib1 state) for ordering switching of the path so that the charged particle beam 81 is guided to the treatment room 1 (treatment room 29a). Further, when the mask signal msig provides the mask cancelling command (signal-value L state), the time-sharing signal ssiga designates the treatment room 1, and the respiratory gate signal gsig1 for the treatment room 1 is "ON" (signal-value H state), the kicker control-signal generator 47 outputs the path-1 command (signal-value Ib1 state) for ordering switching of the path so that the charged particle beam 81 is guided to the treatment room 1 (treatment room 29a).

When the mask signal msig provides the masking command (signal-value H state) and the respiratory gate signal gsig2 is "ON" (signal-value H state), the kicker control-signal generator 47 outputs a path-2 command (signal-value Ib2 state) for ordering switching of the path so that the charged particle beam 81 is guided to the treatment room 2 (treatment room 29b). Further, when the mask signal msig provides the mask cancelling command (signal-value L state), the time-sharing signal ssiga designates the treatment room 2, and the respiratory gate signal gsig2 for the treatment room is "ON" (signal-value H state), the kicker control-signal generator 47 outputs the path-2 command (signal-value Ib2 state) for ordering switching of the path so that the charged particle beam 81 is guided to the treatment room 2 (treatment room 29b).

The kicker control-signal generator 47 outputs, in the case of the path-1 command, a control current of the signal value Ib1 to the kicker electromagnet 10, and outputs, in the case of the path-2 command, a control current of the signal value Ib2 to the kicker electromagnet 10. Note that, in FIG. 17, such a case is shown where, when neither the path-1 command nor the path-2 command is outputted, the signal value of the kicker control signal csigb is at a signal level of other than Ib1 and also other than Ib2, for example, at zero level.

In each of periods from the time t2 to the time t4, from the time t5 to the time t6, and from the time t7 to the time t8, the emitter control signal csiga provides the emission command (signal-value H state) and the kicker control signal csigb provides the path-1 command (signal-value Ib1 state), so that, in the particle beam therapy system 51 of Embodiment 3, the charged particle beam 81 is emitted and the irradiation current Ibem1 is supplied to the irradiation target 31a of the patient 30a in the treatment room 1 (treatment room 29a). In each of periods from the time t4 to the time t5, from the time t6 to the time t7, and from the time t9 to the time t10, the emitter control signal csiga provides the emission command (signal-value H state) and the kicker control signal csigb provides the path-2 command (signal-value Ib2 state), so that, in the particle beam therapy system 51 of Embodiment 3, the charged particle beam 81 is emitted and the irradiation current Ibem2 is supplied to the irradiation target 31b of the patient 30b in the treatment room 2 (treatment room 29b).

The particle beam therapy system 51 of Embodiment 3 achieves the same effect as in Embodiment 1. The particle beam therapy system 51 of Embodiment 3 includes the beam-path controller 63 that generates the kicker control signal csigb and the emitter control signal csiga, by use of the time-sharing signal ssiga with a cycle shorter than that of the time-sharing signal ssig in Embodiment 1 and the mask signal msig for masking the treatment-room selection by the time-sharing signal ssiga; and can supply the irradiation current with a short time width to the irradiation target 31 of the patient 30 with respect to the treatment room from which an irradiation request is issued and which is designated by the time-sharing signal ssiga, when the mask signal msig provides the mask canceling command (signal-value L state). Describing more specifically, as shown from the time t3 to the time t8 in FIG. 17, when the mask signal msig provides the mask cancelling command (signal-value L state) and the respiratory gate signal gsig1 and the respiratory gate signal gsig2 are simultaneously in "ON" state, the beam-path controller 63 causes the path command provided in the kicker control signal csigb to change plural times in a short time period, so that the irradiation current with a short time width can be supplied to the irradiation target 31 of the patient 30.

The particle beam therapy system 51 of Embodiment 3 can supply the irradiation current with a time width shorter than that in Embodiment 1 to the irradiation target 31 of the patient 30; such a method of rapidly switching the beam path as in Embodiment 3 is profitable in the case, like repainting irradiation, where irradiation is performed plural times while decreasing each irradiation dose (the number of particles subjected to irradiation per a specified time period), namely, in the case of irradiation in a manner like that, in pictorial art, a light-colored paint is repeatedly painted.

It is noted that, in FIG. 17, such a case is shown where the number of the respiratory gate signals is two; instead, in the case where the number of the respiratory gate signals is three, the mask signal msig will be given as follows. The mask signal msig provides the masking command in a case where all of the respiratory signals are "OFF" and in each of three cases where only one of the respiratory gate signals becomes "ON", that is, in total four cases. The mask signal msig provides the mask cancelling command in a case where the three respiratory gate signals gsig1, gsig2, gsig3 are simultaneously "ON" and in each of cases (three cases) where two respiratory gate signals in the three respiratory gate signals are simultaneously "ON", that is, in total four cases. Thus, the particle beam therapy system 51 of Embodiment 3 can be applied also in a case where the number of the respiratory gate signals is three or more. Meanwhile, in the case where the number of the respiratory gate signals is three or more, the number of treatment rooms for which the charged particle beam 81 is controlled to be switched in a short time may be limited to two. Further, in the cycle Tc2 of the time-sharing signal ssiga, a time period allocated to each of the treatment rooms 29 for its selection is not limited to the case where it is evenly set, and may be set arbitrarily.

Embodiment 4

In Embodiment 3, such a case has been shown where, when irradiation requests from the plurality of treatment rooms 29 are overlapping, the charged particle beam 81 is controlled to be switched between toward the respective corresponding treatment rooms 1, 2 (treatment rooms 29a, 29b) in a short time, by use of the time-sharing signal ssiga with the cycle Tc2 that is shorter than that in Embodiment 1 and the mask signal msig for masking the treatment-room selection by the time-sharing signal ssiga. In Embodiment 4, such a case will be described where, in the particle beam irradiation system 51 provided with a damper 11 in the beam transport system 59, the charged particle beam 81 is controlled to be switched between toward the plurality of treatment rooms 29 in a short time.

Figure 18:
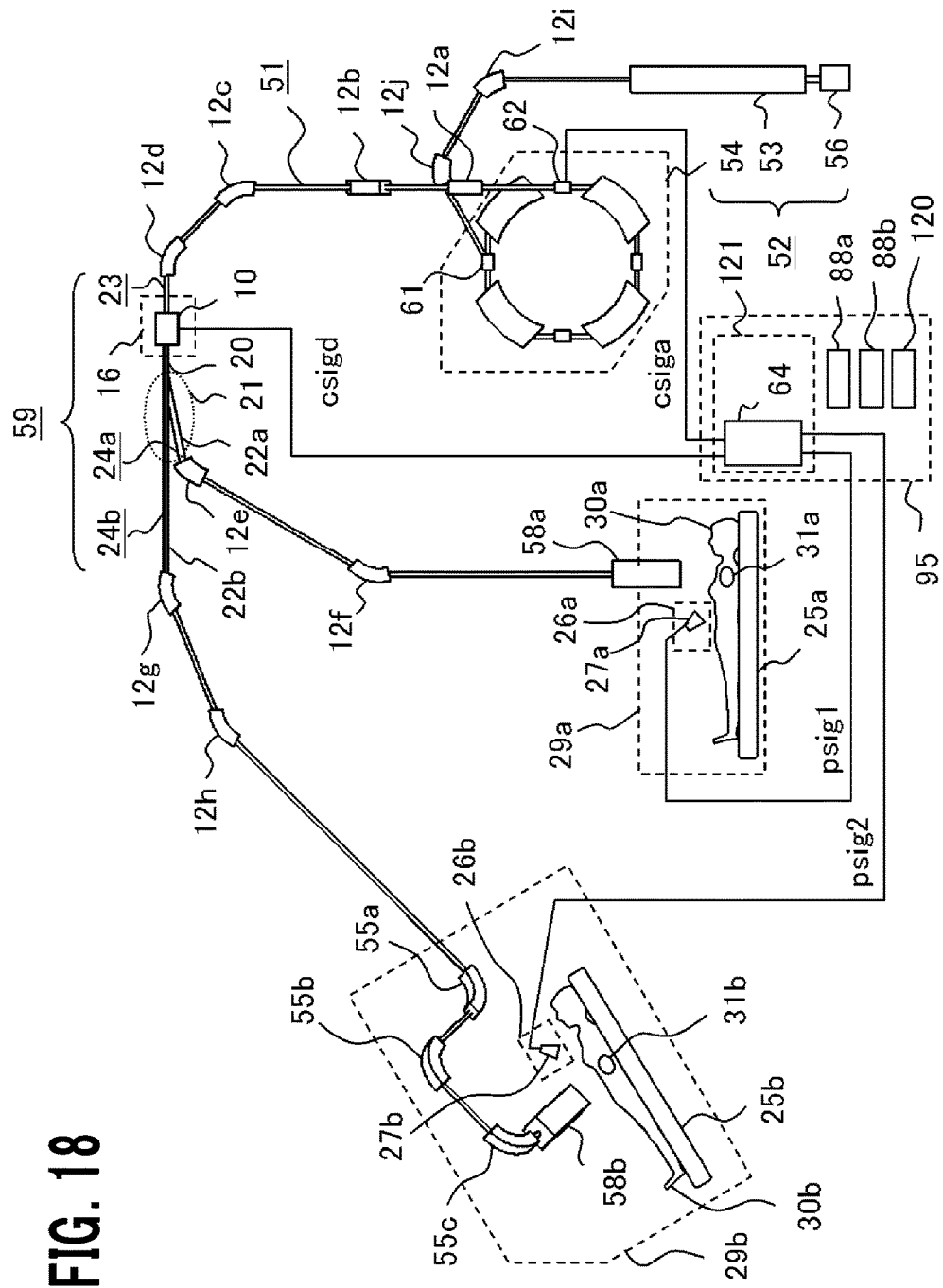
FIG. 18 is a configuration diagram showing a particle beam therapy system according to Embodiment 4 of the invention.
Figure 19:
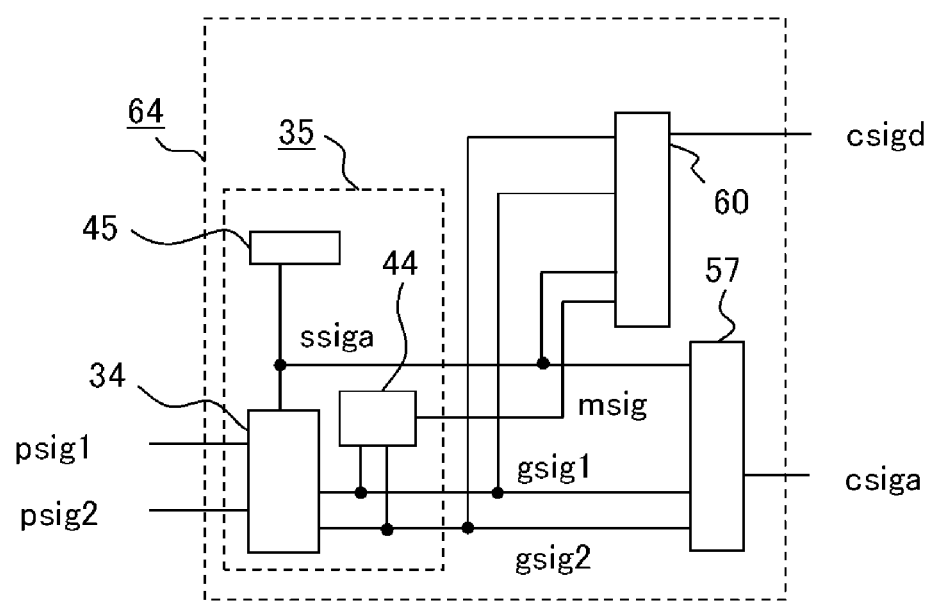
FIG. 19 is a diagram showing a beam-path controller in FIG. 18.
Figure 20:
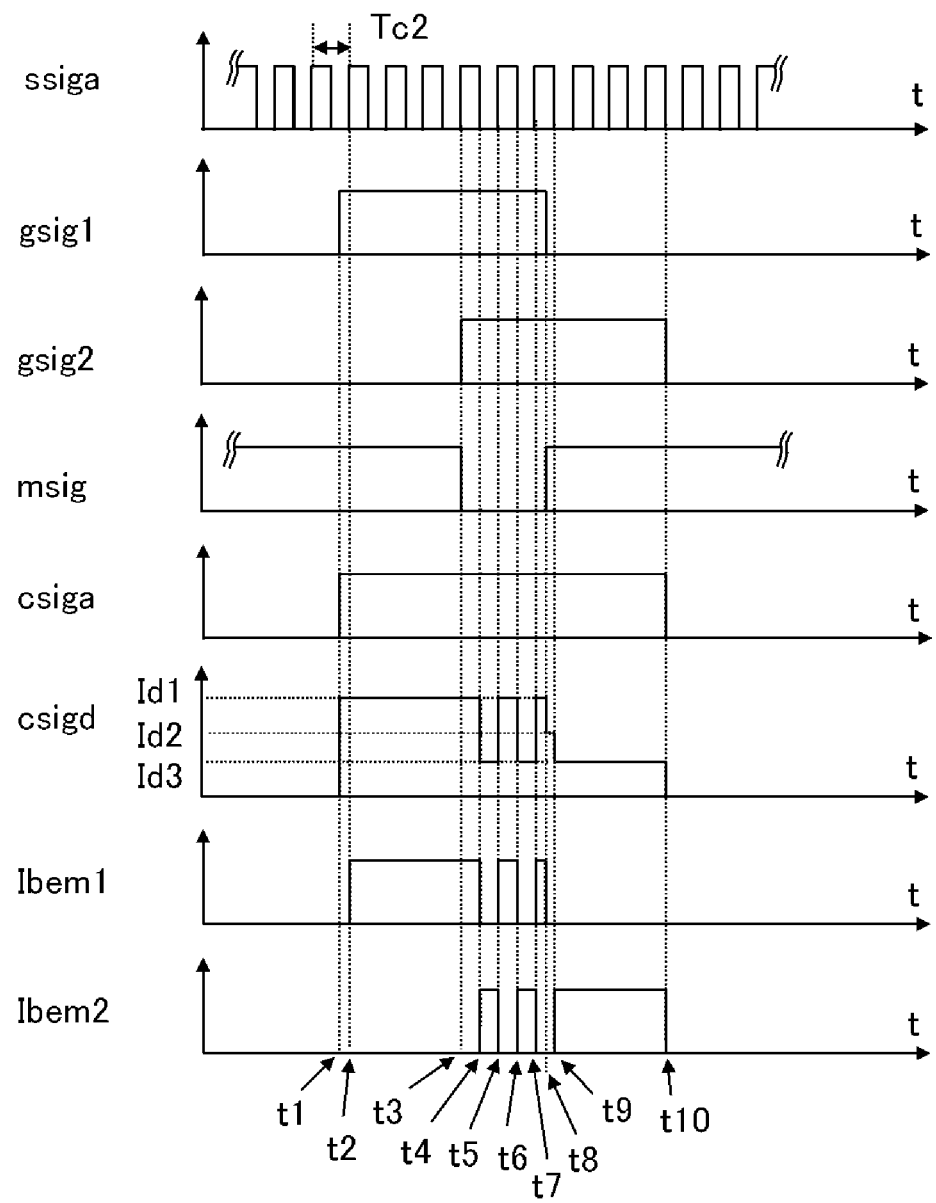
FIG. 20 is a timing chart illustrating a beam distribution to a plurality of treatment rooms according to Embodiment 4 of the invention.

FIG. 18 is a configuration diagram showing a particle beam therapy system according to Embodiment 4 of the invention, and FIG. 19 is a diagram showing a beam-path controller in FIG. 18. FIG. 20 is a timing chart illustrating a beam distribution to a plurality of treatment rooms according to Embodiment 4 of the invention. The treatment management device 95 in Embodiment 4 differs from that in Embodiment 2 in including a beam-path controller 64 that outputs a kicker control signal csigd whose signal value varies in a time period shorter than in Embodiment 2. The beam-path controller 64 includes: an emitter control-signal generator 57 for generating an emitter control signal csiga; a kicker control-signal generator (beam-path changer control-signal generator) 60 for generating the kicker control signal csigd; and a control signal generator 35 for outputting a plurality of control signals to the emitter control-signal generator 57 and the kicker control-signal generator 60. The control signal generator 35 includes: a time-sharing signal generator 45 for generating a time-sharing signal ssiga with a cycle of Tc2 that is shorter than that in Embodiment 2; a respiratory gate-signal generator 34 for generating the respiratory gate signals gsig1, gsig2; and a mask signal generator 44 for generating a mask signal msig for masking a treatment-room selection by the time-sharing signal ssiga.

When irradiation requests from the plurality of treatment rooms 29 are overlapping, for example, when the respiratory gate signal gsig1 for the treatment room 1 is in "ON" state and the respiratory gate signal gsig2 for the other treatment room 2 is in "ON" state, the particle beam therapy system 51 of Embodiment 4 controls so as to make switching of the charged particle beam 81 between toward the respective corresponding treatment rooms 1, 2 (treatment rooms 29a, 29b) in a short time. Further, at a time of switching between a period where irradiation requests from the plurality of treatment rooms 29 are given and a period where an irradiation request only from one of the treatment rooms 29 is given, the particle beam therapy system 51 of Embodiment 4 controls, depending on a situation, so as to switch in a short time between the beam path toward the corresponding treatment room 29 and the beam path toward the damper 11.

First, description will be made on how to control the charged particle beam 81 to be switched between toward the respective corresponding treatment rooms 1, 2 (treatment rooms 29a, 29b) in a short time, when irradiation requests from the plurality of treatment rooms 29 are overlapping. Operations of the particle beam therapy system 51 of Embodiment 4 will be described using FIG. 20. In FIG. 20, the abscissa represents time t. Each ordinate for the time-sharing signal ssiga, the respiratory gate signals gsig1, gsig2, the mask signal msig, the emitter control signal csiga, and the kicker control signal csigd represents a signal value of each of these signals, and each ordinate for the irradiation currents Ibem1, Ibem2 represents a current value. Note that, in order not to complicate the figure, illustrated here is a case where the time-sharing signal ssiga selects the treatment room 1 and the treatment room 2 at its H level and L level, respectively. When the time-sharing signal ssiga is at H level, the treatment room 1 is designated, and when the time-sharing signal ssiga is at L level, the treatment room 2 is designated. Note that the time-sharing signal ssiga can be constituted in a form of the time-sharing signals ssig-1, ssig-2 and ssig-3 shown in FIG. 7.

As shown in FIG. 20, the time-sharing signal generator 45 generates the time-sharing signal ssiga with the cycle Tc2 that is shorter than the cycle Tc1 in Embodiment 2. The mask signal generator 44 receives the respiratory gate signals gsig1, gsig2, to thereby generate the mask signal msig. The mask signal msig is, for example when its output signal value is in H state, a masking command for masking (for making ineffective) a treatment-room selection by the time-sharing signal ssiga. The mask signal msig is, when its output signal value is in L state, a mask cancelling command for making effective a treatment-room selection by the time-sharing signal ssiga. The mask signal generator 44 outputs the mask signal msig as the mask cancelling command when at least two respiratory gate signals in the plurality of respiratory gate signals, are "ON" simultaneously. The mask signal generator 44 outputs the mask signal msig as the masking command when there is no plural respiratory gate signals being simultaneously "ON", namely, when all of the respiratory gate signals are "OFF" or only one of the respiratory gate signals is "ON".

The respiratory gate signal gsig1 is "ON" during the time t1 to the time t8, and the respiratory gate signal gsig2 is "ON" during the time t3 to the time t10, so that the mask signal generator 44 outputs the mask signal msig as the masking command (signal-value H state) in a time period from the time t3 to the time t8 (Period B), and outputs the mask signal msig as the mask cancelling command (signal-value L state) during other than the time period of Period B.

The emitter control-signal generator 57 receives the respiratory gate signals gsig1, gsig2 and the time-sharing signal ssiga, to thereby generate the emitter control signal csiga as follows. When at least one of the respiratory gate signals (respiratory gate signal gsig1 or respiratory gate signal gsig2) is "ON" (signal-value H state) (First Case), the emitter control-signal generator 57 outputs the emission command (signal-value H state) for ordering the emitter 62 to emit the charged particle beam 81. In FIG. 20, the period from the time t1 to the time t10 is a period where the emission command of the charged particle beam 81 is outputted. FIG. 20 differs from FIG. 17 in Embodiment 3 in that, in a period from the time t8 to the time t9, the emitter control signal csiga is kept in the emission-ordering state.

The kicker control-signal generator 60 receives the respiratory gate signals gsig1, gsig2, the time-sharing signal ssiga and the mask signal msig, to thereby generate the kicker control signal csigd as follows. In FIG. 20, when the mask signal msig provides the masking command (signal-value H state) and the respiratory gate signal gsig1 is "ON" (signal-value H state), the kicker control-signal generator 60 outputs a path-1 command (signal-value Id1 state) for ordering switching of the path so that the charged particle beam 81 is guided to the treatment room 1 (treatment room 29a). Further, when the mask signal msig provides the mask cancelling command (signal-value L state), the time-sharing signal ssiga designates the treatment room 1, and the respiratory gate signal gsig1 for the treatment room 1 is "ON" (signal-value H state), the kicker control-signal generator 60 outputs the path-1 command (signal-value Id1 state) for ordering switching of the path so that the charged particle beam 81 is guided to the treatment room 1 (treatment room 29a).

When the mask signal msig provides the masking command (signal-value H state) and the respiratory gate signal gsig2 is "ON" (signal-value H state), the kicker control-signal generator 60 outputs a path-2 command (signal-value Id3 state) for ordering switching of the path so that the charged particle beam 81 is guided to the treatment room 2 (treatment room 29b). Further, when the mask signal msig provides the mask cancelling command (signal-value L state), the time-sharing signal ssiga designates the treatment room 2, and the respiratory gate signal gsig2 for the treatment room is "ON" (signal-value H state), the kicker control-signal generator 60 outputs the path-2 command (signal-value Id3 state) for ordering switching of the path so that the charged particle beam 81 is guided to the treatment room 2 (treatment room 29b).

When the mask signal msig provides the mask cancelling command (signal-value L state), the time-sharing signal ssiga designates either one of the treatment rooms (treatment room 1, treatment room 2), and the respiratory gate signal (gsig1, gsig2) corresponding to that treatment room is "OFF", the kicker control-signal generator 60 outputs the path-3 command (signal-value Id2 state) for ordering switching of the path so that the charged particle beam 81 is guided to the damper 11. Such a case occurs at a time of switching between the period where irradiation requests from the plurality of treatment rooms 29 are given, and the period where an irradiation request only from one of the treatment rooms 29 is given.

The kicker control-signal generator 60 outputs, in the case of the path-1 command, a control current of the signal value Id1 to the kicker electromagnet 10, outputs, in the case of the path-2 command, a control current of the signal value Id3 to the kicker electromagnet 10, and outputs, in the case of the path-3 command, a control current of the signal value Id2 to the kicker electromagnet 10. Note that, in FIG. 20, such a case is shown where, when none of the path-1 command, the path-2 command and the path-3 command is outputted, the signal value of the kicker control signal csigd is at a signal level of other than Id1, Id2 and Id3, for example, at zero level.

During the time t2 to the time t4, the time t5 to the time t6, and the time t7 to the time t8, the emitter control signal csiga provides the emission command (signal-value H state) and the kicker control signal csigd provides the path-1 command (signal-value Id1 state), so that, in the particle beam therapy system 51 of Embodiment 4, the charged particle beam 81 is emitted and the irradiation current Ibem1 is supplied to the irradiation target 31a of the patient 30a in the treatment room 1 (treatment room 29a). During the time t4 to the time t5, the time t6 to the time t7, and the time t9 to the time t10, the emitter control signal csiga provides the emission command (signal-value H state) and the kicker control signal csigd provides the path-2 command (signal-value Id3 state), so that, in the particle beam therapy system 51 of Embodiment 4, the charged particle beam 81 is emitted and the irradiation current Ibem2 is supplied to the irradiation target 31b of the patient 30b in the treatment room 2 (treatment room 29b). During the time t8 to the time t9, although the emitter control signal csiga provides the emission command (signal-value H state) the kicker control signal csigd provides the path-3 command (signal-value Id2 state), so that, in the particle beam therapy system 51 of Embodiment 4, the charged particle beam 81 is shut off by the damper 11.

The particle beam therapy system 51 of Embodiment 4 achieves the same effect as in Embodiment 2. The particle beam therapy system 51 of Embodiment 4 includes the beam-path controller 64 that generates the kicker control signal csigd and the emitter control signal csiga, by use of the time-sharing signal ssiga with a cycle shorter than that of the time-sharing signal ssig in Embodiment 2; and can supply the irradiation current with a short time width to the irradiation target 31 of the patient 30 with respect to the treatment room from which an irradiation request is issued and which is designated by the time-sharing signal ssiga, when the mask signal msig provides the mask canceling command (signal-value L state). Describing more specifically, as shown from the time t3 to the time t8 in FIG. 20, when the mask signal msig provides the mask cancelling command (signal-value L state) and the respiratory gate signal gsig1 and the respiratory gate signal gsig2 are simultaneously in "ON" state, the beam-path controller 64 causes the path command provided in the kicker control signal csigd to change plural times in a short time period, so that the irradiation current with a short time width can be supplied to the irradiation target 31 of the patient 30.

The particle beam therapy system 51 of Embodiment 4 an supply the irradiation current with a time width shorter than that in Embodiment 2 to the irradiation target 31 of the patient 30; such a method of rapidly switching the beam path as in Embodiment 4 is profitable in the case, like repainting irradiation, where irradiation is performed plural times while decreasing each irradiation dose (the number of particles subjected to irradiation per a specified time period), namely, in the case of irradiation in a manner like that, in pictorial art, a light-colored paint is repeatedly painted.

It is noted that, in FIG. 20, such a case is shown where the number of the respiratory gate signals is two; instead, in the case where the number of the respiratory gate signals is three, the mask signal msig will be given as follows. The mask signal msig provides the masking command in a case where all of the respiratory signals are "OFF" and in each of three cases where only one of the respiratory gate signals becomes "ON", that is, in total four cases. The mask signal msig provides the mask cancelling command in a case where the three respiratory gate signals gsig1, gsig2, gsig3 are simultaneously "ON" and in each of cases (three cases) where two respiratory gate signals in the three respiratory gate signals are simultaneously "ON", that is, in total four cases. Thus, the particle beam therapy system 51 of Embodiment 4 can be applied also in a case where the number of the respiratory gate signals is three or more. Meanwhile, in the case where the number of the respiratory gate signals is three or more, the number of treatment rooms for which the charged particle beam 81 is controlled to be switched in a short time may be limited to two. Further, in the cycle Tc2 of the time-sharing signal ssiga, a time period allocated to each of the treatment rooms 29 for its selection is not limited to the case where it is evenly set, and may be set arbitrarily.

Embodiment 5

In Embodiment 3, such a case has been shown where, when irradiation requests from the plurality of treatment rooms 29 are overlapping, the charged particle beam 81 is controlled to be switched between toward the respective corresponding treatment rooms 1, 2 (treatment rooms 29a, 29b) in a short time, by use of the time-sharing signal ssiga with the cycle Tc2 that is shorter than that in Embodiment 1 and the mask signal msig for masking the treatment-room selection by the time-sharing signal ssiga. In Embodiment 5, such a case will be described where the charged particle beam 81 is controlled to be switched between toward the plurality of treatment rooms 29 in a short time without using the mask signal msig, and an irradiation current with a short time width is supplied to one of the treatment rooms 29.

Figure 21:
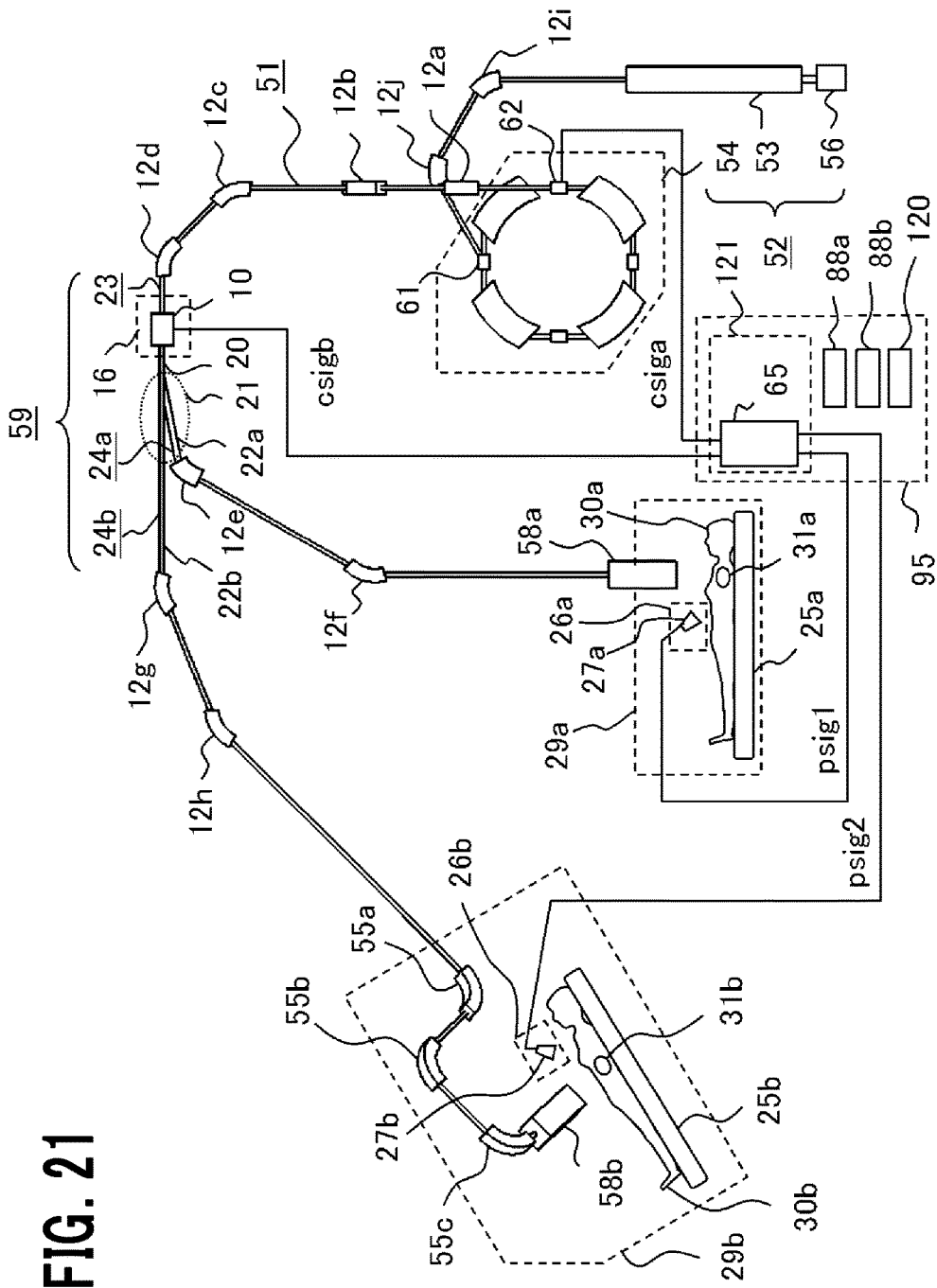
FIG. 21 is a configuration diagram showing a particle beam therapy system according to Embodiment 5 of the invention.
Figure 22:
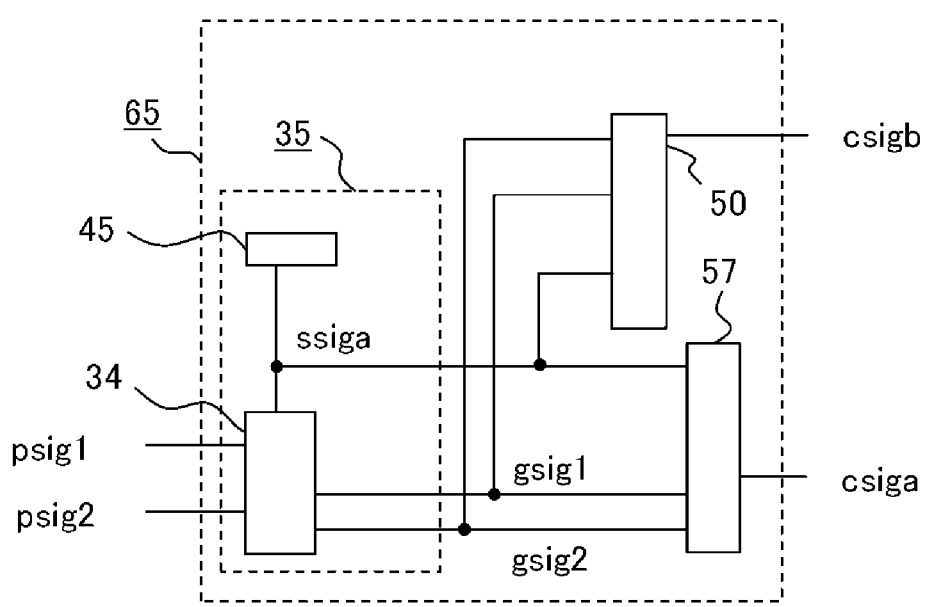
FIG. 22 is a diagram showing a beam-path controller in FIG. 21.
Figure 23:
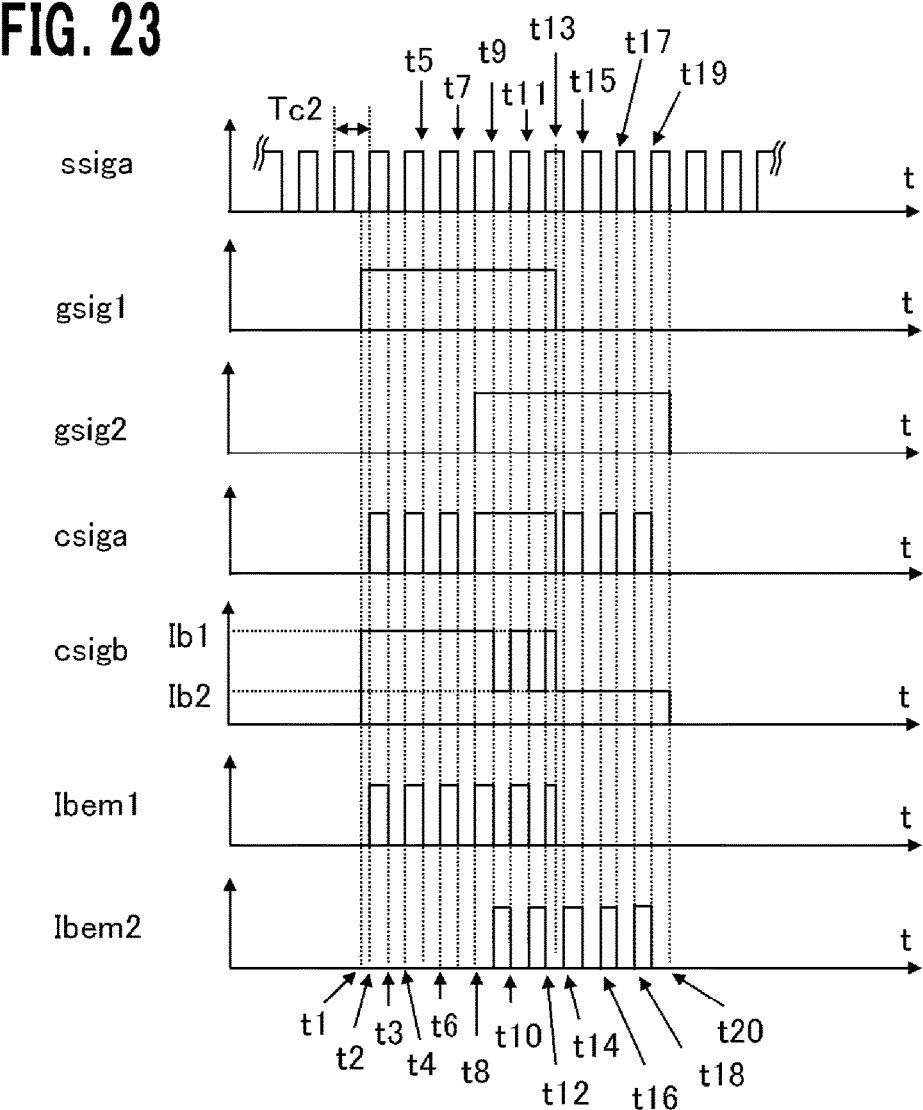
FIG. 23 is a timing chart illustrating a beam distribution to a plurality of treatment rooms according to Embodiment 5 of the invention.

FIG. 21 is a configuration diagram showing a particle beam therapy system according to Embodiment 5 of the invention, and FIG. 22 is a diagram showing a beam-path controller in FIG. 21. FIG. 23 is a timing chart illustrating a beam distribution to a plurality of treatment rooms according to Embodiment 5 of the invention. When irradiation requests from the plurality of treatment rooms 29 are overlapping, for example, when the respiratory gate signal gsig1 for the treatment room 1 is in "ON" state and the respiratory gate signal gsig2 for the other treatment room 2 is in "ON" state, the particle beam therapy system 51 of Embodiment 5 controls so as to make switching of the charged particle beam 81 between toward the respective corresponding treatment rooms 1, 2 (treatment rooms 29a, 29b) in a short time. Further, when an irradiation request from only one of the treatment rooms 29 is issued, the particle beam therapy system 51 of Embodiment 5 controls to make ON-OFF switching of the emitter control signal csiga in a short time, to thereby make switching of the charged particle beam 81 for the corresponding treatment room 29 in a short time. In other words, the particle beam therapy system 51 of Embodiment 5 is a particle beam therapy system that performs switching in a short time between emission of the beam from the emitter 62 and stopping of that beam, and performs switching of the path between toward the respective treatment rooms 29 in a short time by the beam-path changer 16.

The treatment management device 95 in Embodiment 5 includes, like in Embodiment 3, a beam-path controller 65 that outputs a kicker control signal csigb whose signal value varies in a time period shorter than in Embodiment 1. The beam-path controller 65 includes: an emitter control-signal generator 57 for generating an emitter control signal csiga; a kicker control-signal generator (beam-path changer control-signal generator) 50 for generating the kicker control signal csigb; and a control signal generator 35 for outputting a plurality of control signals to the emitter control-signal generator 57 and the kicker control-signal generator 50. The control signal generator 35 includes: a time-sharing signal generator 45 for generating a time-sharing signal ssiga with a cycle of Tc2 that is shorter than that in Embodiment 1; and a respiratory gate-signal generator 34 for generating the respiratory gate signals gsig1, gsig2. As shown in FIG. 23, the time-sharing signal generator 45 generates the time-sharing signal ssiga with the cycle Tc2 that is shorter than the cycle Tc1 in Embodiment 1.

Operations of the particle beam therapy system 51 of Embodiment 5 will be described using FIG. 23. In FIG. 23, the abscissa represents time t. Each ordinate for the time-sharing signal ssiga, the respiratory gate signals gsig1, gsig2, the emitter control signal csiga, and the kicker control signal csigb represents a signal value of each of these signals, and each ordinate for the irradiation currents Ibem1, Ibem2 represents a current value. Note that, in order not to complicate the figure, illustrated here is a case where the time-sharing signal ssiga selects the treatment room 1 and the treatment room 2 at its H level and L level, respectively. When the time-sharing signal ssiga is at H level, the treatment room 1 is designated, and when the time-sharing signal ssiga is at L level, the treatment room 2 is designated. Note that the time-sharing signal ssiga can be constituted in a form of the time-sharing signals ssig-1, ssig-2 and ssig-3 shown in FIG. 7.

The emitter control-signal generator 57 receives the respiratory gate signals gsig1, gsig2 and the time-sharing signal ssiga, to thereby generate the emitter control signal csiga as follows. First of all, with respect to the emission command (signal-value H state) for ordering the emitter 62 to emit the charged particle beam 81, the following four cases arise. When only one of the respiratory gate signals (respiratory gate signal gsig1 or respiratory gate signal gsig2) is "ON" (signal-value H state), the time-sharing signal ssiga designates the treatment room 1, and the respiratory gate signal gsig1 for the treatment room 1 is "ON" (signal-value H state) (First Case), the emitter control-signal generator 57 outputs the emission command (signal-value H state) for ordering the emitter 62 to emit the charged particle beam 81. Further, when only one of the respiratory gate signals (respiratory gate signal gsig1 or respiratory gate signal gsig2) is "ON" (signal-value H state), the time-sharing signal ssiga designates the treatment room 2, and the respiratory gate signal gsig2 for the treatment room 2 is "ON" (signal-value H state) (Second Case), the emitter control-signal generator 57 outputs the emission command (signal-value H state) for ordering the emitter 62 to emit the charged particle beam 81. Further, when the plurality of respiratory gate signals (respiratory gate signal gsig1 and respiratory gate signal gsig2) are "ON" (signal-value H state), the time-sharing signal ssiga designates the treatment room 1, and the respiratory gate signal gsig1 for the treatment room 1 is "ON" (signal-value H state) (Third Case), the emitter control-signal generator 57 outputs the emission command (signal-value H state) for ordering the emitter 62 to emit the charged particle beam 81.

Further, when the plurality of respiratory gate signals (respiratory gate signal gsig1 and respiratory gate signal gsig2) are "ON" (signal-value H state), the time-sharing signal ssiga designates the treatment room 2, and the respiratory gate signal gsig2 for the treatment room 2 is "ON" (signal-value H state) (Fourth Case), the emitter control-signal generator 57 outputs the emission command (signal-value H state) for ordering the emitter 62 to emit the charged particle beam 81. In other than the above four cases, the emitter control-signal generator 57 outputs the emission stop command (signal-value L state) for ordering the emitter 62 to stop emission of the charged particle beam 81. In FIG. 23, the period from the time t2 to the time t3, the period from the time t4 to the time t5, the period from the time t6 to the time t7, the period from the time t8 to the time t13, the period from the time t14 to the time t15, the period from the time t16 to the time t17 and the period from the time t18 to the time t19 are each a period where the emission command of the charged particle beam 81 is outputted.

The kicker control-signal generator 50 receives the respiratory gate signals gsig1, gsig2, and the time-sharing signal ssiga, to thereby generate the kicker control signal csigb as follows. In FIG. 23, when only one respiratory gate signals is "ON" (signal-value H state), namely, only the respiratory gate signal gsig1 is "ON" (signal-value H state), the kicker control-signal generator 50 outputs a path-1 command (signal-value Ib1 state) for ordering switching of the path so that the charged particle beam 81 is guided to the treatment room 1 (treatment room 29a). Further, when only the other one respiratory gate signal is "ON" (signal-value H state), namely, only the respiratory gate signal gsig2 is "ON" (signal-value H state), the kicker control-signal generator 50 outputs a path-2 command (signal-value Ib2 state) for ordering switching of the path so that the charged particle beam 81 is guided to the treatment room 2 (treatment room 29b).

Meanwhile, when the plurality of respiratory gate signals (respiratory gate signal gsig1 and respiratory gate signal gsig2) are "ON" (signal-value H state), the time-sharing signal ssiga designates the treatment room 1, and the respiratory gate signal gsig1 for the treatment room 1 is "ON" (signal-value H state), the kicker control-signal generator 50 outputs the path-1 command (signal-value Ib1 state) for ordering switching of the path so that the charged particle beam 81 is guided to the treatment room 1 (treatment room 29a). Further, when the plurality of respiratory gate signals (respiratory gate signal gsig1 and respiratory gate signal gsig2) are "ON" (signal-value H state), the time-sharing signal ssiga designates the treatment room 2, and the respiratory gate signal gsig2 for the treatment room 2 is "ON" (signal-value H state), the kicker control-signal generator 50 outputs the path-2 command (signal-value Ib2 state) for ordering switching of the path so that the charged particle beam 81 is guided to the treatment room (treatment room 29b).

The kicker control-signal generator 50 outputs, in the case of the path-1 command, a control current of the signal value Ib1 to the kicker electromagnet 10, and outputs, in the case of the path-2 command, a control current of the signal value Ib2 to the kicker electromagnet 10. Note that, in FIG. 23, such a case is shown where, when neither the path-1 command nor the path-2 command is outputted, the signal value of the kicker control signal csigb is at a signal level of other than Ib1 and also other than Ib2, for example, at zero level.

In each of periods from the time t2 to the time t3, from the time t4 to the time t5, from the time t6 to the time t7, from the time t8 to the time t9, from the time t10 to the time 11 and from the time t12 to the time t13, the emitter control signal csiga provides the emission command (signal-value H state) and the kicker control signal csigb provides the path-1 command (signal-value Ib1 state), so that, in the particle beam therapy system 51 of Embodiment 5, the charged particle beam 81 is emitted and the irradiation current Ibem1 is supplied to the irradiation target 31a of the patient 30a in the treatment room 1 (treatment room 29a). In each of periods from the time t9 to the time t10, from the time t11 to the time t12, from the time t14 to the time t15, from the time t16 to the time t17 and from the time t18 to the time t19, the emitter control signal csiga provides the emission command (signal-value H state) and the kicker control signal csigb provides the path-2 command (signal-value Ib2 state), so that, in the particle beam therapy system 51 of Embodiment 5, the charged particle beam 81 is emitted and the irradiation current Ibem2 is supplied to the irradiation target 31b of the patient 30b in the treatment room 2 (treatment room 29b).

The particle beam therapy system 51 of Embodiment 5 achieves the same effect as in Embodiment 1. The particle beam therapy system 51 of Embodiment 5 includes the beam-path controller 65 that generates the kicker control signal csigb and the emitter control signal csiga, by use of the time-sharing signal ssiga with a cycle shorter than that of the time-sharing signal ssig in Embodiment 1; and can supply the irradiation current with a short time width to the irradiation target. 31 of the patient 30 with respect to the treatment room from which an irradiation request is issued and which is designated by the time-sharing signal ssiga. Describing more specifically, as shown from the time t8 to the time t13 in FIG. 23, when the respiratory gate signal gsig1 and the respiratory gate signal gsig2 are simultaneously in "ON" state, the beam-path controller 65 causes the path command provided in the kicker control signal csigb to change plural times in a short time period; and, as shown from the time t2 to the time t8 and from the time t13 to the time t19, when only one respiratory gate signal is "ON" (signal-value H state), the emitter control signal csiga is subjected to ON-OFF switching with the same cycle Tc2 as that of the time-sharing signal ssiga; so that the irradiation current with a short time width can be supplied to the irradiation target 31 of the patient 30.

Like Embodiment 3, the particle beam therapy system 51 of Embodiment 5 can supply the irradiation current with a time width shorter than that in Embodiment 1 to the irradiation target 31 of the patient 30; such a method of rapidly switching the beam path as in Embodiment 5 is profitable in the case, like repainting irradiation, where irradiation is performed plural times while decreasing each irradiation dose (the number of particles subjected to irradiation per a specified time period), namely, in the case of irradiation in a manner like that, in pictorial art, a light-colored paint is repeatedly painted. Because of no use of the mask signal msig, the particle beam therapy system 51 of Embodiment 5 has such a merit that the control signal generator 35 is simplified in its control as compared to Embodiment 3.

It is noted that, in FIG. 23, such a case is shown where the number of the respiratory gate signals is two; however, the particle beam therapy system 51 of Embodiment 5 can be applied also in a case where the number of the respiratory gate signals is three or more. Further, in the cycle Tc2 of the time-sharing signal ssiga, a time period allocated to each of the treatment rooms 29 for its selection is not limited to the case where it is evenly set, and may be set arbitrarily.

Embodiment 6

In Embodiment 5, such a case has been shown where, in the particle beam therapy system 51 not provided with the damper 11 in the beam transport system 59, the charged particle beam 81 is controlled to be switched toward the plurality of treatment rooms 29 in a short time without using the mask signal msig, and an irradiation current with a short time width is supplied to one of the treatment rooms 29. In Embodiment 6, such a case will be described where, in the particle beam therapy system 51 provided with the damper 11 in the beam transport system 59, the charged particle beam 81 is controlled to be switched between toward the plurality of treatment rooms 29 in a short time without using the mask signal msig, and an irradiation current with a short time width is supplied to one of the treatment rooms 29.

Figure 24:
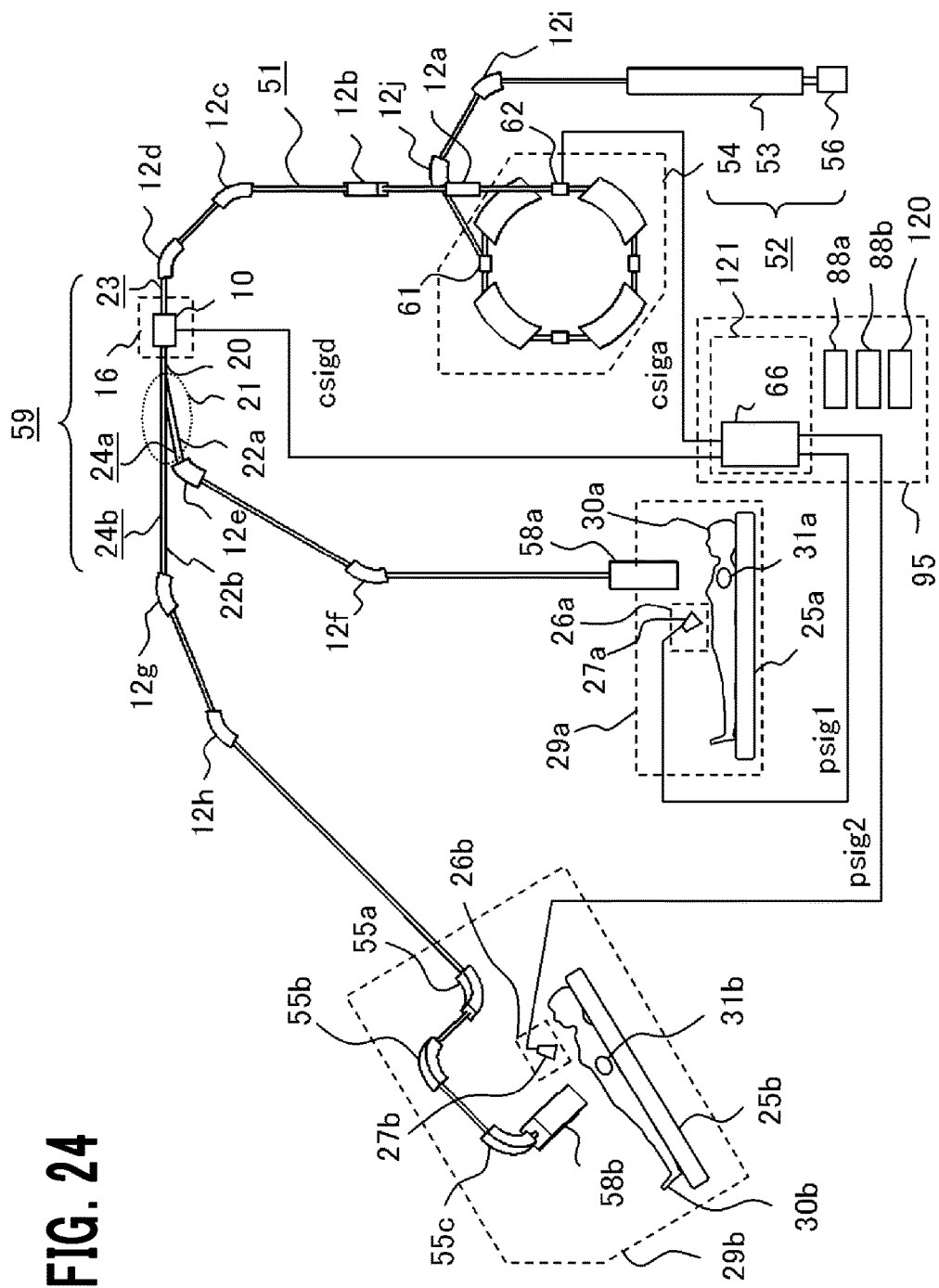
FIG. 24 is a configuration diagram showing a particle beam therapy system according to Embodiment 6 of the invention.
Figure 25:
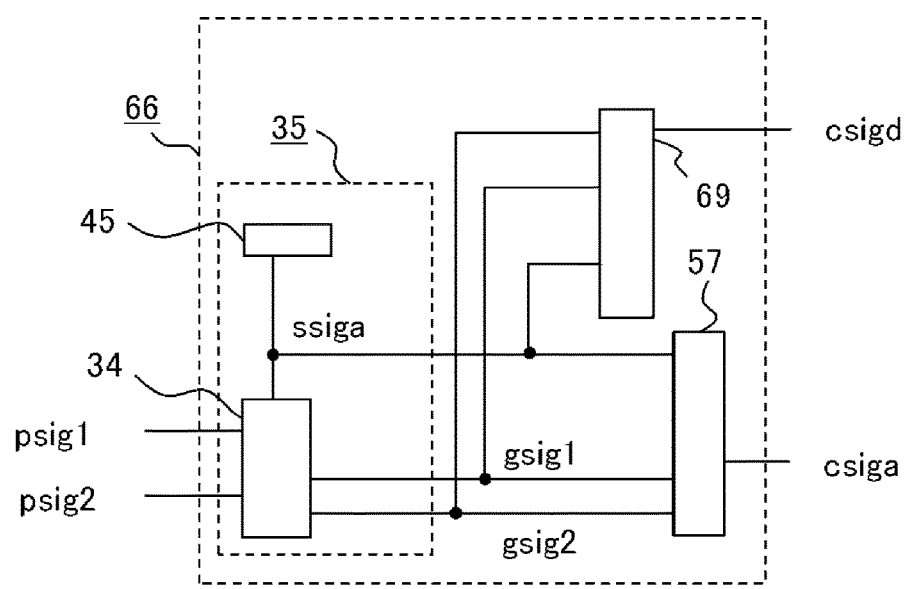
FIG. 25 is a diagram showing a beam-path controller in FIG. 24.
Figure 26:
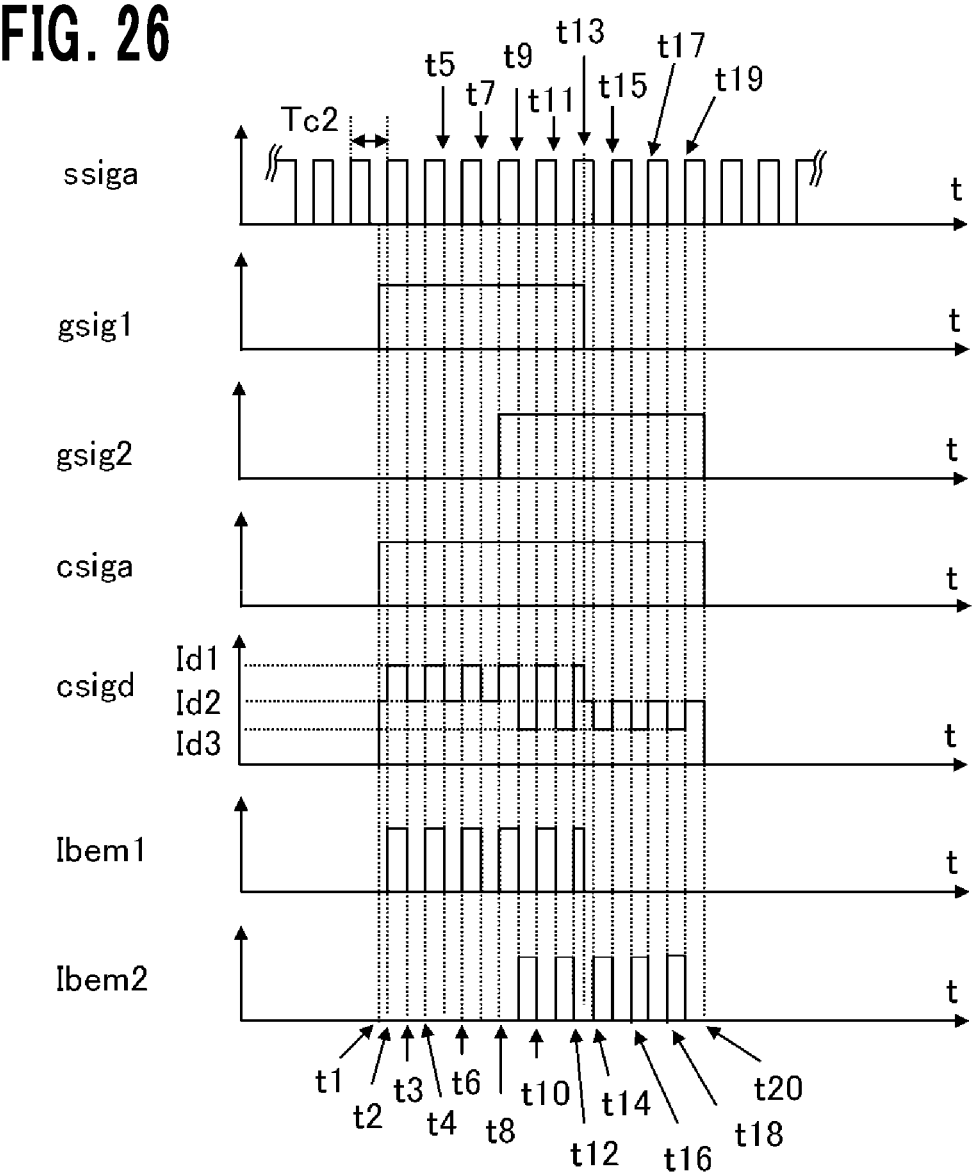
FIG. 26 is a timing chart illustrating a beam distribution to a plurality of treatment rooms according to Embodiment 6 of the invention.

FIG. 24 is a configuration diagram showing a particle beam therapy system according to Embodiment 6 of the invention, and FIG. 25 is a diagram showing a beam-path controller in FIG. 24. FIG. 26 is a timing chart illustrating a beam distribution to a plurality of treatment rooms according to Embodiment 6 of the invention. When irradiation requests from the plurality of treatment rooms 29 are overlapping, for example, when the respiratory gate signal gsig1 for the treatment room 1 is in "ON" state and the respiratory gate signal gsig2 for the other treatment room 2 is in "ON" state, the particle beam therapy system 51 of Embodiment 6 controls so as to make switching of the charged particle beam 81 between toward the respective corresponding treatment rooms 1, 2 (treatment rooms 29a, 29b) in a short time. Further, when an irradiation request from only one of the treatment rooms 29 is issued, the particle beam therapy system 51 of Embodiment 6 controls to make switching between the path toward the corresponding treatment room 29 and the path toward the damper 11 in a short time. In other words, the particle beam therapy system 51 of Embodiment 6 is a particle beam therapy system that performs switching between the paths toward the plurality of treatment rooms 29 and switching between the paths toward the one treatment room 29 and toward the damper 11, in a short time by the beam-path changer 16.

The treatment management device 95 in Embodiment 6 includes a beam-path controller 66 that outputs a kicker control signal csigd whose signal value varies in a time period shorter than in Embodiment 2. The beam-path controller 66 includes: an emitter control-signal generator 57 for generating an emitter control signal csiga; a kicker control-signal generator 69 for generating the kicker control signal csigd; and a control signal generator 35 for outputting a plurality of control signals to the emitter control-signal generator 57 and the kicker control-signal generator 69. The control signal generator 35 includes: a time-sharing signal generator 45 for generating a time-sharing signal ssiga with a cycle of Tc2 that is shorter than that in Embodiment 2; and a respiratory gate-signal generator 34 for generating the respiratory gate signals gsig1, gsig2. As shown in FIG. 26, the time-sharing signal generator 45 generates the time-sharing signal ssiga with the cycle Tc2 that is shorter than the cycle Tc1 in Embodiment 2.

Operations of the particle beam therapy system 51 of Embodiment 6 will be described using FIG. 26. In FIG. 26, the abscissa represents time t. Each ordinate for the time-sharing signal ssiga, the respiratory gate signals gsig1, gsig2, the emitter control signal csiga, and the kicker control signal csigd represents a signal value of each of these signals, and each ordinate for the irradiation currents Ibem1, Ibem2 represents a current value. Note that, in order not to complicate the figure, illustrated here is a case where the time-sharing signal ssiga selects the treatment room 1 and the treatment room 2 at its H level and L level, respectively. When the time-sharing signal ssiga is at H level, the treatment room 1 is designated, and when the time-sharing signal ssiga is at L level, the treatment room 2 is designated. Note that the time-sharing signal ssiga can be constituted in a form of the time-sharing signals ssig-1, ssig-2 and ssig-3 shown in FIG. 7.

The emitter control-signal generator 57 receives the respiratory gate signals gsig1, gsig2 and the time-sharing signal ssiga, to thereby generate the emitter control signal csiga as follows. When at least one of the respiratory gate signals (respiratory gate signal gsig1 or respiratory gate signal gsig2) is "ON" (signal-value H state) (First Case), the emitter control-signal generator 57 outputs the emission command (signal-value H state) for ordering the emitter 62 to emit the charged particle beam 81. In FIG. 26, the period from the time t1 to the time t20 is a period where the emission command of the charged particle beam 81 is outputted.

The kicker control-signal generator 69 receives the respiratory gate signals gsig1, gsig2, and the time-sharing signal ssiga, to thereby generate the kicker control signal csigd as follows. As shown from the time t2 to the time t8 and from the time t14 to the time t20 in FIG. 26, when one treatment room 29 for which the respiratory gate signal is being "ON", is selected by the time-sharing signal ssiga, the kicker control-signal generator 69 outputs a path command (radiation-permissive path command) for ordering switching of the path so that the particle beam 81 is guided to the corresponding treatment room 29, while, when the other treatment room 29 is selected by the time-sharing signal ssiga, the kicker control-signal generator 69 outputs another path command (path shutoff command) for ordering switching of the path so that the particle beam 81 is guided to the damper 11.

Further, this similarly applies also to the case where the plurality of respiratory gate signals are "ON" (signal-value H state), so that, when the treatment room 29 for which the respiratory gate signal is being "ON", is selected by the time-sharing signal ssiga, the kicker control-signal generator 69 outputs a path command (radiation-permissive path command) for ordering switching of the path so that the particle beam 81 is guided to the corresponding treatment room 29, while, when the other treatment room 29 is selected by the time-sharing signal ssiga, the kicker control-signal generator 69 outputs another path command (radiation-permissive path command) for ordering switching of the path so that the particle beam 81 is guided to the corresponding treatment room 29. When such a situation continues where, even for any one of the different treatment rooms, the respiratory gate signal is "ON" (signal-value H state) and the corresponding treatment room 29 for which the respiratory gate signal is "ON" (signal-value H state) is selected by the time-sharing signal ssiga, the kicker control-signal generator 69 outputs the path command (irradiation-permissive path command) for ordering switching of the path so that the charged particle beam 81 is guided to change from toward one treatment room 29 to toward the other treatment room 29, as shown from the time t8 to the time t12 in FIG. 26.

The kicker control signal csigd in FIG. 26 will be described specifically. As shown from the time t1 to the time t8, when only the respiratory gate signal gsig1 is "ON" (signal-value H state), if the time-sharing signal ssiga designates the treatment room 1, the kicker control-signal generator 69 outputs a path-1 command (signal-value Id1 state) for ordering switching of the path so that the charged particle beam 81 is guided to the treatment room 1 (treatment room 29a). Further, when only the respiratory gate signal gsig1 is "ON" (signal-value H state), if the time-sharing signal ssiga designates the other treatment room 2, the kicker control-signal generator 69 outputs a path-2 command (signal-value Id3 state) for ordering switching of the path so that the charged particle beam 81 is guided to the damper 11.

During the time t8 to the time t13, irradiation requests from the plurality of treatment rooms 29 are overlapping, and thus, the plurality of respiratory gate signals (respiratory gate signal gsig1 and respiratory gate signal gsig2) are "ON" (signal-value H state). In this overlapping situation of the irradiation requests, when the time-sharing signal ssiga designates the treatment room 1 and the respiratory gate signal gsig1 for the treatment room 1 is "ON" (signal-value H state), the kicker control-signal generator 69 outputs the path-1 command (signal-value Id1 state) for ordering switching of the path so that the charged particle beam 81 is guided to the treatment room 1 (treatment room 29a). Further, in the overlapping situation of the irradiation requests, when the time-sharing signal ssiga designates the treatment room 2 and the respiratory gate signal gsig2 for the treatment room 2 is "ON" (signal-value H state), the kicker control-signal generator 69 outputs the path-2 command (signal-value Id3 state) for ordering switching of the path so that the charged particle beam 81 is guided to the treatment room 2 (treatment room 29b).

During the time t13 to the time t20, there is shown a case where only the respiratory gate signal gsig2 is "ON" (signal-value H state). When only the respiratory gate signal gsig2 is "ON" (signal-value H state), if the time-sharing signal ssiga designates the treatment room 2, the kicker control-signal generator 69 outputs the path-2 command (signal-value Id3 state) for ordering switching of the path so that the charged particle beam 81 is guided to the treatment room 2 (treatment room 29b). Further, when only the respiratory gate signal gsig2 is "ON" (signal-value H state), if the time-sharing signal ssiga designates the other treatment room 1, the kicker control-signal generator 69 outputs the path-3 command (signal-value Id2 state) for ordering switching of the path so that the charged particle beam 81 is guided to the damper 11.

The kicker control-signal generator 69 outputs, in the case of the path-1 command, a control current of the signal value Id1 to the kicker electromagnet 10, outputs, in the case of the path-2 command, a control current of the signal value Id3 to the kicker electromagnet 10, and outputs, in the case of the path-3 command, a control current of the signal value Id2 to the kicker electromagnet 10. Note that, in FIG. 26, such a case is shown where, when none of the path-1 command, path-2 command and the path-3 command is outputted, the signal value of the kicker control signal csigd is at a signal level of other than Id1, Id2 and Id3, for example, at zero level.

In each of periods from the time t2 to the time t3, from the time t4 to the time t5, from the time t6 to the time t7, from the time t8 to the time t9, from the time t10 to the time t11 and from the time t12 to the time t13, the emitter control signal csiga provides the emission command (signal-value H state) and the kicker control signal csigd provides the path-1 command (signal-value Id1 state), so that, in the particle beam therapy system 51 of Embodiment 6, the charged particle beam 81 is emitted and the irradiation current Ibem1 is supplied to the irradiation target 31a of the patient 30a in the treatment room 1 (treatment room 29a). In each of periods from the time t9 to the time t10, from the time t11 to the time t12, from the time t14 to the time t15, from the time t16 to the time t17 and from the time t18 to the time t19, the emitter control signal csiga provides the emission command (signal-value H state) and the kicker control signal csigd provides the path-2 command (signal-value Id3 state), so that, in the particle beam therapy system 51 of Embodiment 6, the charged particle beam 81 is emitted and the irradiation current Ibem2 is supplied to the irradiation target 31b of the patient 30b in the treatment room 2 (treatment room 29b). In each of periods from the time t1 to the time t2, from the time t3 to the time t4, from the time t5 to the time t6, from the time t7 to the time t8, from the time t13 to the time t14, from the time t15 to the time t16, from the time t17 to the time t18 and from the time t19 to the time t20, although the emitter control signal csiga provides the emission command (signal-value H state), the kicker control signal csigd provides the path-3 command (signal-value Id2 state), so that, in the particle beam therapy system 51 of Embodiment 6, the charged particle beam 81 is shut off by the damper 11.

The particle beam therapy system 51 of Embodiment 6 achieves the same effect as in Embodiment 2. The particle beam therapy system 51 of Embodiment 6 includes the beam-path controller 66 that generates the kicker control signal csigd and the emitter control signal csiga, by use of the time-sharing signal ssiga with a cycle shorter than that of the time-sharing signal ssig in Embodiment 1; and can supply the irradiation current with a short time width to the irradiation target 31 of the patient 30 with respect to the treatment room from which an irradiation request is issued and which is designated by the time-sharing signal ssiga. Describing more specifically, as shown from the time t1 to the time t20 in FIG. 26, when at least one of the respiratory gate signals (gsig1, gsig2) is in "ON" state, the beam-path controller 66 performs switching of the beam path by changing plural times the path command (path-1 command, path-2 command, path-3 command) provided in the kicker control signal csigd in a short time; so that the irradiation current with a short time width can be supplied to the irradiation target 31 of the patient 30.

According to the particle beam therapy system 51 of Embodiment 6, at the time of supplying the irradiation current with a short time width to the irradiation target 31 of the patient 30 in the designated treatment room, switching of the beam path is made by changing only the beam-path changer 16 plural times in a short time period, without changing the emitter 62 that is slower in ON-OFF switching than the kicker electromagnet 10 in a short time by use of the emitter control signal csiga, so that the irradiation current with a time width shorter than that in Embodiment 5 can be supplied to the irradiation target 31 of the patient 30.

Like Embodiment 4, the particle beam therapy system 51 of Embodiment 6 can supply the irradiation current with a time width shorter than that in Embodiment 1 to the irradiation target 31 of the patient 30; such a method of rapidly switching the beam path as in Embodiment 6 is profitable in the case, like repainting irradiation, where irradiation is performed plural times while decreasing each irradiation dose (the number of particles subjected to irradiation per a specified time period), namely, in the case of irradiation in a manner like that, in pictorial art, a light-colored paint is repeatedly painted. Because of no use of the mask signal msig, the particle beam therapy system 51 of Embodiment 6 has such a merit that the control signal generator 35 is simplified in its control as compared to Embodiment 4.

It is noted that, in FIG. 26, such a case is shown where the number of the respiratory gate signals is two; however, the particle beam therapy system 51 of Embodiment 6 can be applied also in a case where the number of the respiratory gate signals is three or more. Further, in the cycle Tc2 of the time-sharing signal ssiga, a time period allocated to each of the treatment rooms 29 for its selection is not limited to the case where it is evenly set, and may be set arbitrarily.

Embodiment 7

In Embodiments 1 to 6, the description has been made using the case where the kicker electromagnet 10 is used as the beam-path changer 16; however, in place of the kicker electromagnet 10, a beam deflector 15 to be described later may be used. Here, since the kicker electromagnet 10 includes a small deflectable angle for deflecting the charged particle beam 81, such a requirement is imposed that the bending magnet 12e for constituting the beam path has to be placed to stay away from the kicker electromagnet 10 at the downstream side thereof. This requirement may become a bottleneck when the particle beam therapy system is to be designed compact. Accordingly, in Embodiment 7, such a case will be shown where the beam deflector 15 is used, thereby to achieve rapid switching of the beam path and to allow the particle beam therapy system to be designed compact.

Figure 27:
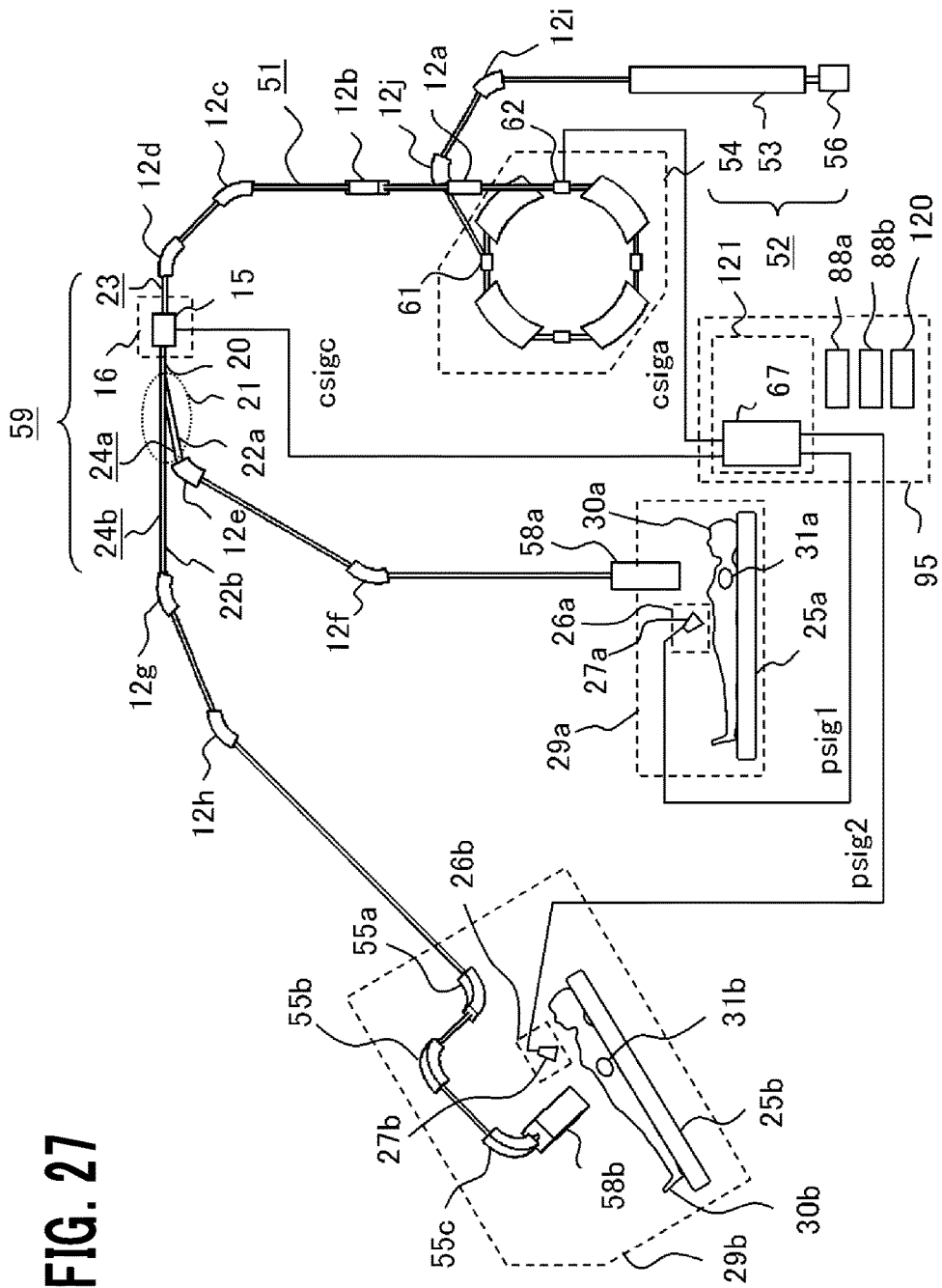
FIG. 27 is a configuration diagram showing a particle beam therapy system according to Embodiment 7 of the invention.
Figure 28:
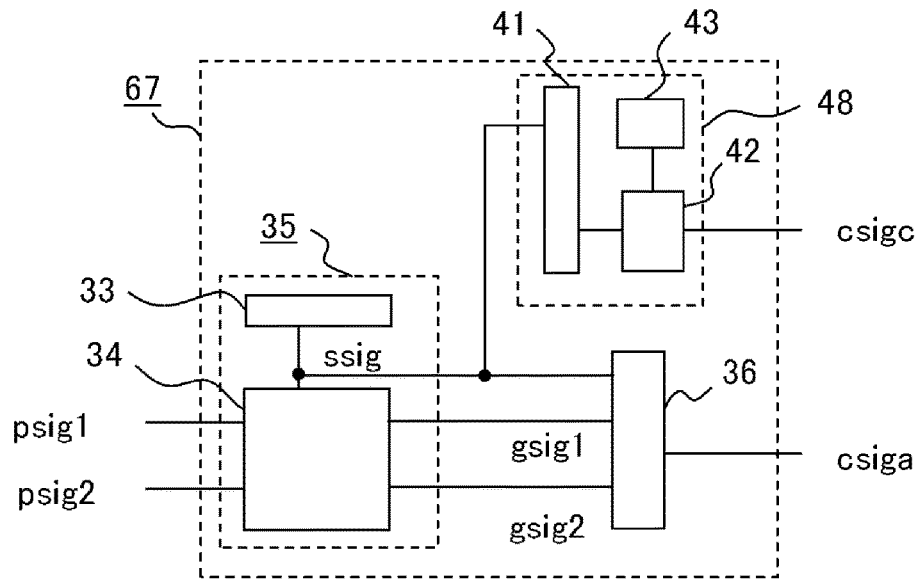
FIG. 28 is a diagram showing a beam-path controller in FIG. 27.
Figure 29:
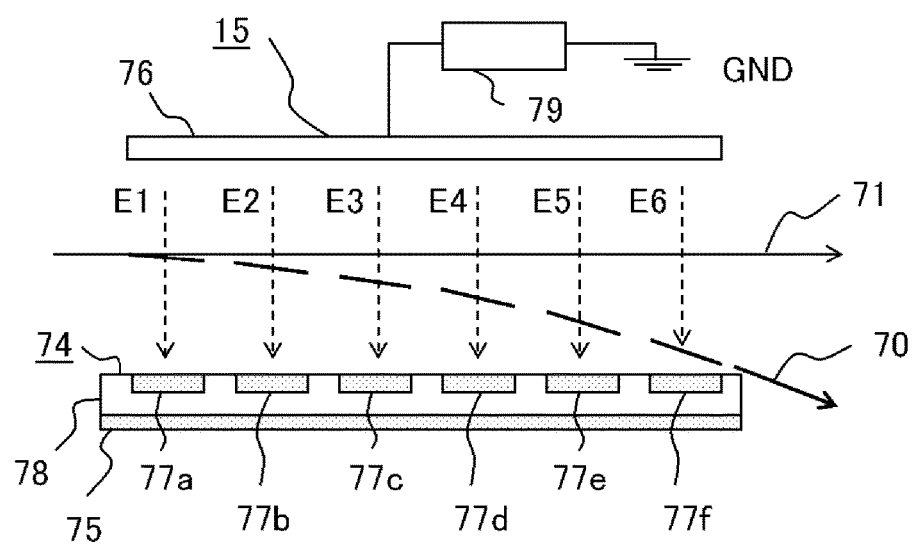
FIG. 29 is a side view showing a beam deflector in FIG. 27.
Figure 30:
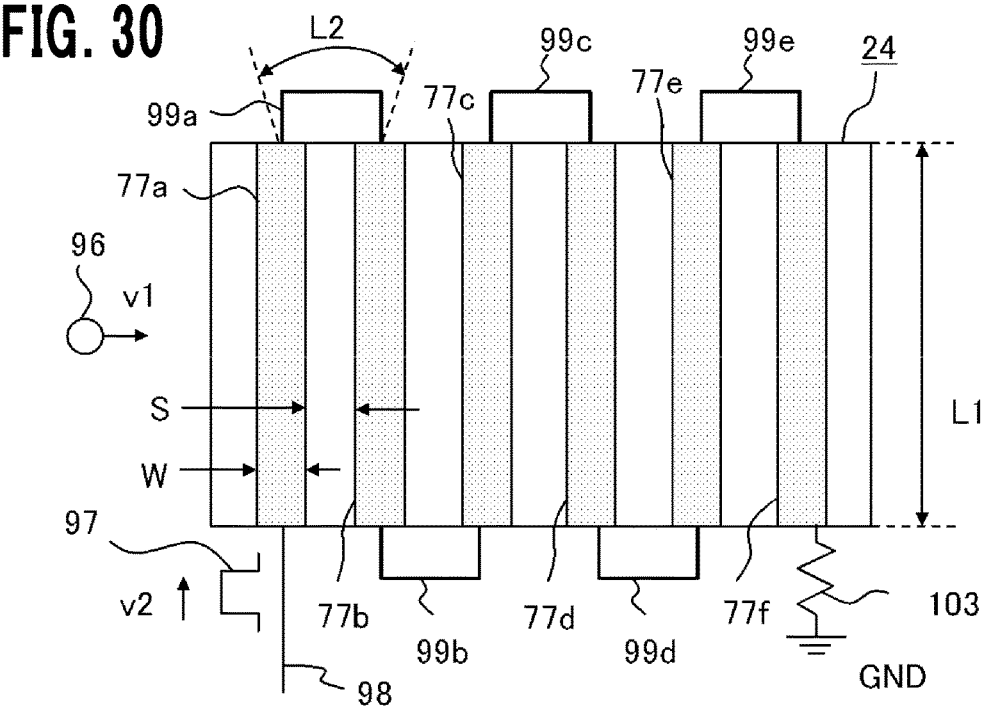
FIG. 30 is a top view of the beam deflector in FIG. 27, viewed from its upper side.
Figure 31:
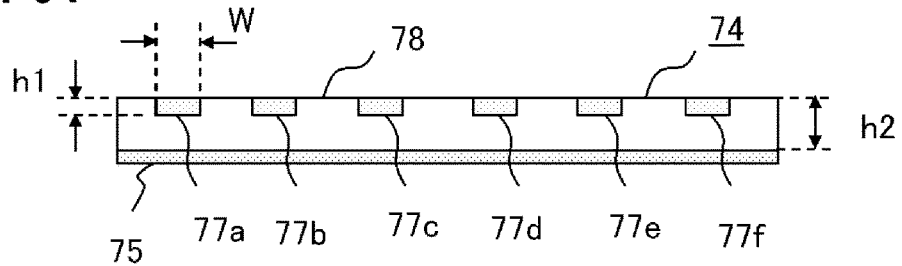
FIG. 31 is a diagram illustrating a micro-strip line in the beam deflector in FIG. 27.
Figure 32:
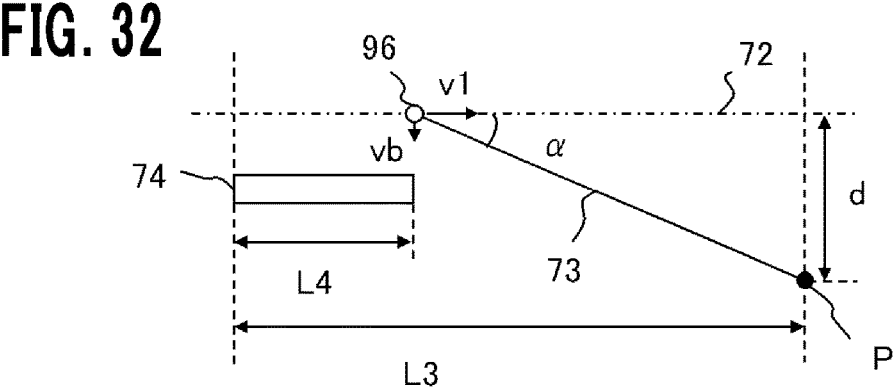
FIG. 32 is a diagram illustrating a beam control by the beam deflector in FIG. 27.
Figure 33:
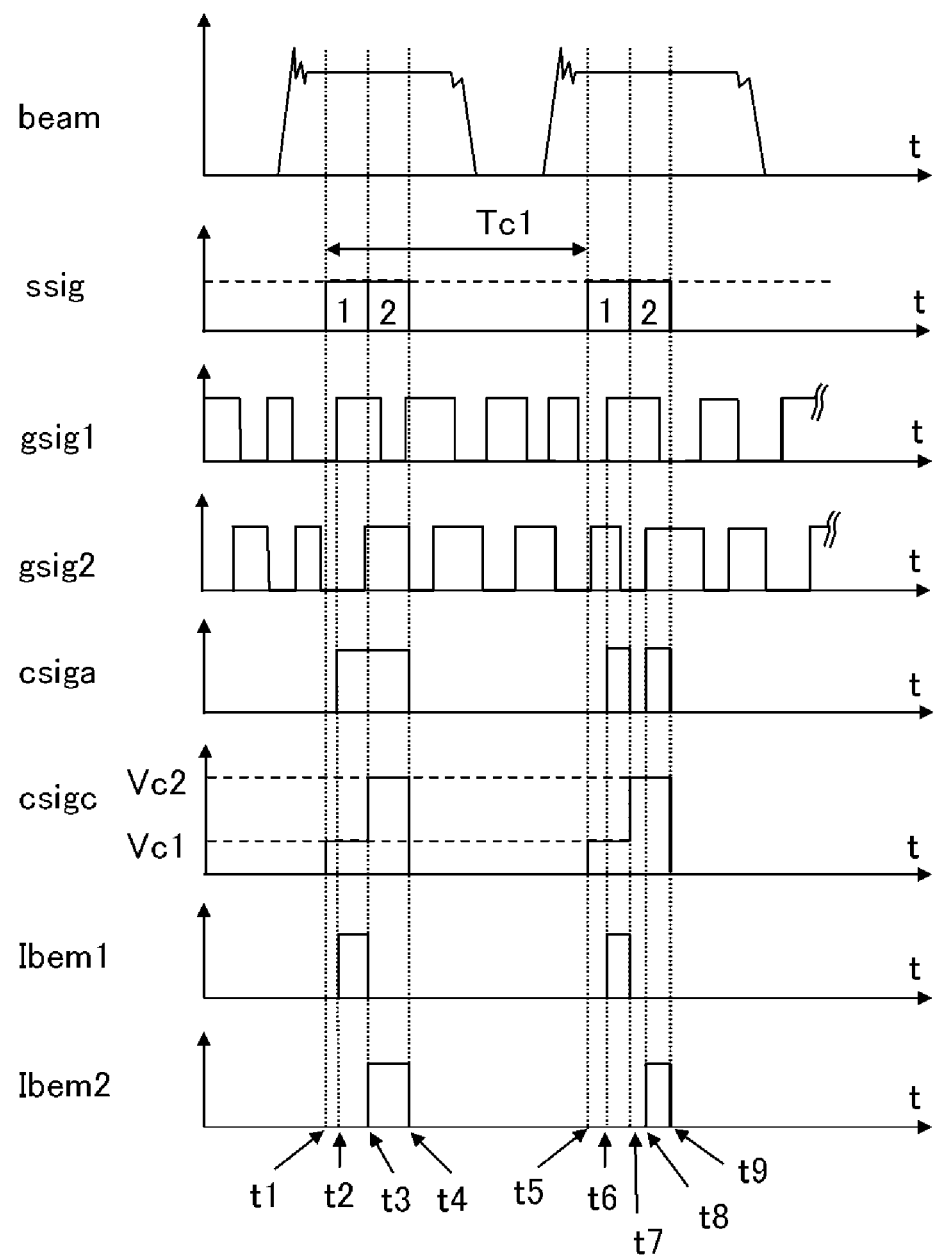
FIG. 33 is a timing chart illustrating a beam distribution to a plurality of treatment rooms according to Embodiment 7 of the invention.

FIG. 27 is a configuration diagram showing a particle beam therapy system according to Embodiment 7 of the invention, and FIG. 28 is a diagram showing a beam-path controller in FIG. 27. FIG. 29 is a side view showing a beam deflector in FIG. 27, and FIG. 30 is a top view of the beam deflector in FIG. 27, viewed from its upper side. FIG. 31 is a diagram illustrating a micro-strip line in the beam deflector in FIG. 27, and FIG. 32 is a diagram illustrating a beam control by the beam deflector in FIG. 27. FIG. 33 is a timing chart illustrating a beam distribution to a plurality of treatment rooms according to Embodiment 7 of the invention. The particle beam therapy system 51 of Embodiment 7 differs from that of Embodiment 1 in that the beam deflector 15 is used as the beam-path changer 16 and the treatment management device 95 includes a beam-path controller 67 that outputs a beam-deflector control signal csigc (beam-path changer control signal) for controlling the beam deflector 15.

The beam-path controller 67 includes: a time-sharing signal generator 33 for generating the time-sharing signal ssig; a respiratory gate-signal generator 34 for generating the respiratory gate signals gsig1, gsig2; an emitter control-signal generator 36 for generating the emitter control signal csiga; and a beam-deflector control-signal generator (beam-path changer control-signal generator) 48 for generating the beam-deflector control signal csigc. The time-sharing signal generator 33 and the respiratory gate-signal generator 34 constitute a control signal generator 35. The beam-deflector control-signal generator 48 includes a pulse controller 41, a high-speed switch 42 and a deflector power source 43.

Configurations of the beam deflector 15 and the beam-deflector control-signal generator 48 are disclosed in Japanese Patent Application Laid-open No. 2012-024254. Before describing them in detail using FIG. 28 to FIG. 32, a summary thereof will be described. A beam deflector 15 disclosed in Japanese Patent Application Laid-open No. 2012-024254 includes, for the purpose of suppressing a transient dose at the time of shutting off the beam in a scanning irradiation method to thereby improve an accuracy in irradiation dose: a line electrode plate 74 in which a plurality of conductive plates 77a to 77f are placed so that a traverse direction of each of them is arranged along the beam traveling direction; and an electrode plate 76 placed in parallel to the line electrode plate 74. In the beam deflector 15 disclosed in Japanese Patent Application Laid-open No. 2012-024254, there is included a passing region between the line electrode plate 74 and the electrode plate 76 through which the charged particle beam 81 passes. The plurality of the conductive plates 77a to 77f are serially connected in their longitudinal directions and are subjected to impedance matching. A beam-deflector control device (beam-deflector control-signal generator 48) is configured to output a voltage pulse 97 whose transmission base time is synchronized with a particle-movement base time, said transmission base time being a transmission cycle in which the voltage pulse is transmitted through each of the plurality of conductive plates 77a to 77f in the longitudinal direction, and said particle-movement base time being a passing cycle in which the charged particle beam 81 passes through each of the plurality of conductive plates 77a to 77f in the traverse direction. The voltage pulse 97 corresponds to the beam-deflector control signal csigc. For the conductive plates, numeral 77 is used collectively, and this numeral is used as being suffixed with each of "a" to "f" when they are to be described distinctively.

The beam deflector 15 includes the line electrode plate 74 and the electrode plate 76 opposite to the line electrode plate 74. The line electrode plate 74 is an electrostatic electrode plate of a micro-strip line type. The line electrode plate 74 is provided by placing the plurality of conductive plates 77, such as copper plates or the like, in parallel on a front face of a base plate 78, such as a GFRP (glass fiber reinforced plastics) plate or the like, and by placing a backside conductor 75, such as a copper plate or the like, on a back face of the base plate 78. The backside conductor 75 is placed at a ground level (connected to GND), the electrode plate 76 is connected to a DC power source (direct-current power source) 79, and the voltage pulse 97 is transmitted through each of the conductive plates 77a to 77f of the line electrode plate 74. The electrode plate 76 and the line electrode plate 74 are placed in parallel relative to an incident beam axis of the charged particle beam 81. The beam deflector 15 includes a passing region between the line electrode plate 74 and the electrode plate 76 through which the charged particle beam 81 passes. When the voltage pulse 97 is not inputted to the line electrode plate 74, namely, when a voltage at the ground level is applied thereto, the charged particle beam 81 is deflected due to the respective electric fields E1 to E6 established between the electrode plate 76 and the line electrode plate 74 (the direction is from the electrode plate 76 to the line electrode plate 74). When the voltage pulse 97 is inputted to the line electrode plate 74, this acts to cancel the respective electric fields E1 to E6 otherwise established between the electrode plate 76 and the line electrode plate 74, so that the charged particle beam 81 goes straightforward. The electric field E1 is an electric field between the conductive plate 77a and the electrode plate 76. Likewise, the electric fields E2 to E6 are electric fields respectively between the conductive plates 77b to 77f and the electrode plate 76. Note that in FIG. 29, the line electrode plate 74 and the electrode plate 76 are each shown as its cross section.

A deflection angle at which the charged particle beam 81 is deflected by the beam deflector 15, is determined by the respective electric fields E1 to E6 established between the electrode plate 76 and the line electrode plate 74. Let's assume the case where a voltage of Vb is applied by the DC power source 79 to the electrode plate 76. When the voltage Vp of the voltage pulse 97 applied to the line electrode plate 74 is Vb (Vp=Vb), the charged particle beam 81 is not deflected, so that the charged particle beam 81 results in a straightforward beam 71, thus passing through the beam deflector 15 along the incident beam axis. When the voltage Vp of the voltage pulse 97 applied to the line electrode plate 74 is a voltage at the ground level (0 V) (Vp=0), the charged particle beam 81 is deflected, so that the charged particle beam 81 results in a deflection beam 70, thus passing through the beam deflector 15 while being deflected from the incident beam axis. When the voltage Vp of the voltage pulse 97 applied to the line electrode plate 74 is more than 0 V but less than Vb (0<Vp<Vb), the charged particle beam 81 passes through the beam deflector 15 on a path between the deflection beam 70 and the straightforward beam 71. Note that, when the voltage Vp of the voltage pulse 97 applied to the line electrode plate 74 is a voltage higher than Vb, the charged particle beam 81 passes through the beam deflector 15 on a path deflected upward from the straightforward beam 71. As described above, by transmitting the voltage pulse 97 with an arbitrary voltage Vp to the line electrode plate 74, it is possible to deflect the charged particle beam 81 at an arbitrary deflection angle.

In the line electrode plate 74, as shown in FIG. 31, the conductive plates 77a to 77f, each having a width of W, a length of L1 (see, FIG. 30) and a thickness of h1, are placed in an exposed manner on the base plate 78 having a thickness of h2. Since the line electrode plate 74 is provided with a micro-strip line structure, based on a principle of impedance matching (impedance matching adjustment) between micro-strip lines, the conductive plates 77a to 77f have each a predetermined impedance (for example, 50Ω). Further, as shown in FIG. 30, the conductive plates 77a to 77f are placed as being spaced apart to each other by an interval S. Here, assuming that the dielectric constant of the base plate 78 is $\in_r$, the characteristic impedance $Z_0$ of the micro strip line is represented as shown in a formula (1).

$$Z_0 = 87/(\in_r + 1.41)^{1/2} \times ln(A/B) \quad (1)$$

Note that A and B are represented as shown in a formula (2) and a formula (3), respectively.

$$A = 5.98 \times (h2 - h1) \quad (2)$$

$$B = 0.8 \times W \times h1 \quad (3)$$

By making selection on the dielectric constant $\in_r$, the width W, the thickness h1 and the thickness h2, a given impedance (for example, 50Ω) can be obtained.

As shown in FIG. 30, the six conductive plates 77a to 77f of the line electrode plate 74 are connected to each other via respective delay lines 99 (99a to 99e) so that they are serially connected to constitute a single transmission line. For the delay lines, numeral 99 is used collectively, and this numeral is used as being suffixed with each of "a" to "e" when they are to be described distinctively. To the conductive plate 77a, an input line 98 for introducing the voltage pulse 97 thereto is connected, and to the terminal end of the conductive plate 77f, a terminal resistance 103 with its one end being grounded is connected. The respective conductive plates 77a to 77f of the line electrode plate 74 have each a given impedance (for example, 50Ω) and are grounded at the terminal end via the terminal resistance 103 for impedance matching, so that the voltage pulse 97 resulting from switching and inputted to the line electrode plate 74 can be transmitted in the line electrode plate 74 without causing reflection. Note that the impedance of each of the delay lines 99 (99a to 99e) and the terminal resistance 103 is made equal to the impedance of each of the conductive plates 77a to 77f.

Meanwhile, the delay lines 99a to 99e may be formed, like a printed wiring, on the base plate 78 using a lithography technology or a multi-layer interconnection technology. When the delay lines 99a to 99e are formed on the base plate 78, a soldering work, etc. for bonding the delay lines 99a to 99e becomes unnecessary, so that it is possible to easily perform adjustment of impedance in the line electrode plate 74.

How to control traveling of the charged particle beam 81 by the beam deflector 15 will be described in detail. Since the charged particle beam 81 is a flux of plural charged particles 96 (referred to as particle (s) 96, as appropriate), the line electrode plate 74 is configured so that a predetermined synchronous relationship to be described later is established between a time period in which one of the particles 96 passes through the conductive plate 77 in its traverse direction (shorter-side length) and a time period in which the voltage pulse 97 passes through the conductive plate 77 in its longitudinal direction (longer-side length), and thus, only a particle group influenced by the voltage pulse 97 at the first conductive plate 77a is to be influenced also by the voltage pulse 97 at each of the next conductive plates 77b to 77f. This makes the particle group corresponding to the width (time width) of the voltage pulse resulting from switching by the voltage Vb, not to be influenced by the electric field E at the time the particle group is incident to the line electrode plate 74, so that it is possible to cause the beam to go straightforward. Further, when the voltage Vp of the voltage pulse 97 is set to other than Vb, it is possible to deflect the beam.

Let's assume the case where the particle 96 passes through the center along the line electrode plate 74. This is because, while paying attention to a center component of the beam, the beam is put in use after being adjusted so that the center component passes through the line electrode plate 74. When the velocity of the particle 96 is defined as v1, a time period in which the particle 96 passes through the conductive plate 77 is W/v1. A time period (particle-movement base time) TP0 in which the particle 96 passes through the conductive plate 77 in the traverse direction (shorter-side length) to reach the next conductive plate 77, is (W+S)/v1. When the velocity of the voltage pulse 97 transmitted through the conductive plate 77 having a predetermined transmission characteristic is defined as v2, a time period in which the voltage pulse 97 passes through the conductive plate 77 in the longitudinal direction (longer-side length) is L1/v2. Meanwhile, based on a propagation delay time TD of the delay line 99, its effective length L2 that corresponds to the longitudinal length of the conductive plate 77 is adopted here. The effective length L2 can be calculated by v2×TD. A time period in which the pulse passes through the first conductive plate 77 and then passes through the delay line 99, namely, a time period (transmission base time) TV0 in which the pulse passes through the first conductive plate 77 to reach the next conductive plate 77, is given as (L1+L2)/v2. The line electrode plate 74 is configured so that the particle-movement base time TP0 and the transmission base time TV0 are matched to each other. This achieves the above predetermined synchronous relationship, so that, as described above, the particle group corresponding to the width (time width) of the voltage pulse resulting from switching by the voltage Vb, is not influenced by the electric field E at the time it is incident to the line electrode plate 74, thus making it possible to cause the beam to go straightforward. Note that the particle-movement base time TP0 is a passing cycle in which the charged particle beam 81 passes through each of the plurality of conductive plates 77a to 77f in the traverse direction, and the transmission base time TV0 is a transmission cycle in which the pulse passes through each of the conductive plates 77a to 77f in the longitudinal direction.

Description will be made about the velocity v1 of the particle 96 and the transmission velocity v2 of the voltage pulse 97 that are required to achieve the above predetermined synchronous relationship in which the particle-movement base time TP0 and the transmission base time TV0 are matched to each other. The velocity v1 of the particle 96 and the transmission velocity v2 of the voltage pulse 97 are represented as shown in a formula (4) and a formula (5), respectively.

$$v1 = c \times \sqrt{(1-(Es/(Es+K))^2)} \quad (4)$$

$$v2 = 1/\sqrt{(L \times C)} \quad (5)$$

Here, "K" represents energy (MeV) of the particle 96, "c" represents the light velocity, "Es" represents the static energy of a proton, "L" represents the inductance of the conductive plate 77 and "C" represents the electric capacitance of the conductive plate 77.

Description will be made about the electric field E to be applied using the beam deflector 15 to the charged particle beam 81. FIG. 32 is a diagram illustrating a condition for calculating the electric field E. Indicated at 72 is a straightforward-beam parallel axis that is parallel to the straight beam 71 that is the charged particle beam 81 passing through the beam deflector 15. A point "P" is an evaluation point at which a deflected distance d of the charged particle beam 81 is evaluated, and which corresponds, for example, to an entrance point into the bending magnet 12e in the downstream beam-transport system 24a. The length of the line electrode plate 74 is defined as L4, and the distance on the straightforward-beam parallel axis from the front end of the line electrode plate 74 to the evaluation point P is defined as L3. At the terminal end of the line electrode plate 74, although the charged particle 96 has a velocity component of v1 in the direction of the straightforward-beam parallel axis, the charged particle beam 96 affords, upon being influenced by the electric field E, a component vertical to the line electrode plate 74. The vertical component (vertical velocity component) in the velocity of the charged particle 96 is defined as vb. Further, an angle by a deflection beam trajectory 73 and the straightforward-beam parallel axis 72 is defined as α. The vertical velocity component vb of the charged particle 96 is v1×tan α, so that it is represented as shown in a formula (6).

$$vb = v1 \times d/(L3-L4) \quad (6)$$

Let's assume a potential difference Vd required for the charged particle 96 to have the vertical velocity component vb at the terminal end of the line electrode plate 74. When the mass of proton is defined as m1 and an electric charge thereof is defined as q, the kinetic energy is ½×m1×vb² at the terminal end of the line electrode plate 74 and the energy afforded by the charged particle 96 due to the potential difference Vd is q×Vd, so that the potential difference V is represented as shown in a formula (7).

$$Vd = (\tfrac{1}{2} \times m1 \times vb^2)/q \quad (7)$$

The potential difference Vd required at the terminal end of the line electrode plate 74 is to be shared by an n1 number of the respective conductive plates 77 in the line electrode plate 74. Namely, it suffices to develop the electric field E between the n1 number of the conductive plates 77 in the line electrode plate 74 and the electrode plate 76 so that the charged particle 96 is subjected to a potential difference of Vd/n1 per one of the conductive plates 77. When the particle passes through the width W of the conductive plate 77, the time period taken to pass through the width W is v1/W, so that a moving distance da in the direction vertical to the line electrode plate 74 is represented as shown in a formula (8).

$$da = (vb/n1) \times (W/v1) \quad (8)$$

Accordingly, since the electric field E to be applied to the charged particle beam 81 in the beam deflector 15 is (Vd/n1)/da, when the formulae (7), (8) are assigned thereto followed by being subjected to arrangement, it is represented as shown in a formula (9).

$$E = (\tfrac{1}{2} \times m1 \times vb \times v1)/(q \times W) \quad (9)$$

When the formula (6) is assigned to the formula (9) followed by being subjected to arrangement, the electric field E is represented as shown in a formula (10).

$$E = m1 \times d \times v1^2/(2 \times q \times W \times (L3-L4)) \quad (10)$$

Operations of the particle beam therapy system 51 of Embodiment 7 will be described using FIG. 33. Description will be made about part of operations which differs from Embodiment 1. In FIG. 27, a beam transport system 59 is configured so that the charged particle beam 81 to be transported to the treatment room 1 (treatment room 29a) is deflected by the beam deflector 15 so as to be directed toward the bending magnet 12e, while the charged particle beam 81 to be transported to the treatment room 2 (treatment room 29b) goes straightforward without being deflected by the beam deflector 15 so as to be directed toward the bending magnet 12g. When the time-sharing signal ssig designates the treatment room 1 (treatment room 29a), the beam-path controller 67 outputs a path-1 command (signal-value Vc1 state) for ordering switching of the path so that the charged particle beam 81 is guided to the treatment room 1 (treatment room 29a). When the time-sharing signal ssig designates the treatment room 2 (treatment room 29b), the beam-path controller 67 outputs a path-2 command (signal-value Vc2 state) for ordering switching of the path so that the charged particle beam 81 is guided to the treatment room 2 (treatment room 29b). Here, the signal value Vc2 (voltage Vc2) is the voltage Vb applied to the electrode plate 76, and the signal value Vc1 (voltage Vc1) is a voltage lower then Vc2. Although the magnitude relationship between the signal values Vc1, Vc2 of the beam-deflector control signal csigc is reversed from the magnitude relationship between the signal values Ib1, Ib2 of the kicker control signal csigb in Embodiment 1, as described above, the path-1 command is provided when the beam-deflector control signal csigc has the signal value Vc1 and the path-2 command is provided when the beam-deflector control signal csigc has the signal value Vc2. Accordingly, the particle beam therapy system 51 of Embodiment 7 operates similarly to in Embodiment 1.

According to the beam deflector 15, the deflection angle can be made larger than that by the kicker electromagnet 10, so that it is possible to make the distance from the beam deflector 15 to the bending magnet 12e shorter than that in Embodiment 1. In the particle beam therapy system 51 of Embodiment 7, the beam transport system 59 that is more compact than that in Embodiment 1 can be configured.

The particle beam therapy system 51 of Embodiment 7 achieves the same effect as in Embodiment 1. Further, the particle beam therapy system 51 of Embodiment 7 is configured to use the beam deflector 15 in place of the kicker electromagnet 10 in Embodiment 1. With such a configuration, it is possible to switch the beam path faster and to make the deflection angle larger, than that by the kicker electromagnet 10, so that the particle beam therapy system can be designed compact while achieving rapid switching of the beam path.

Embodiment 8

Figure 34:
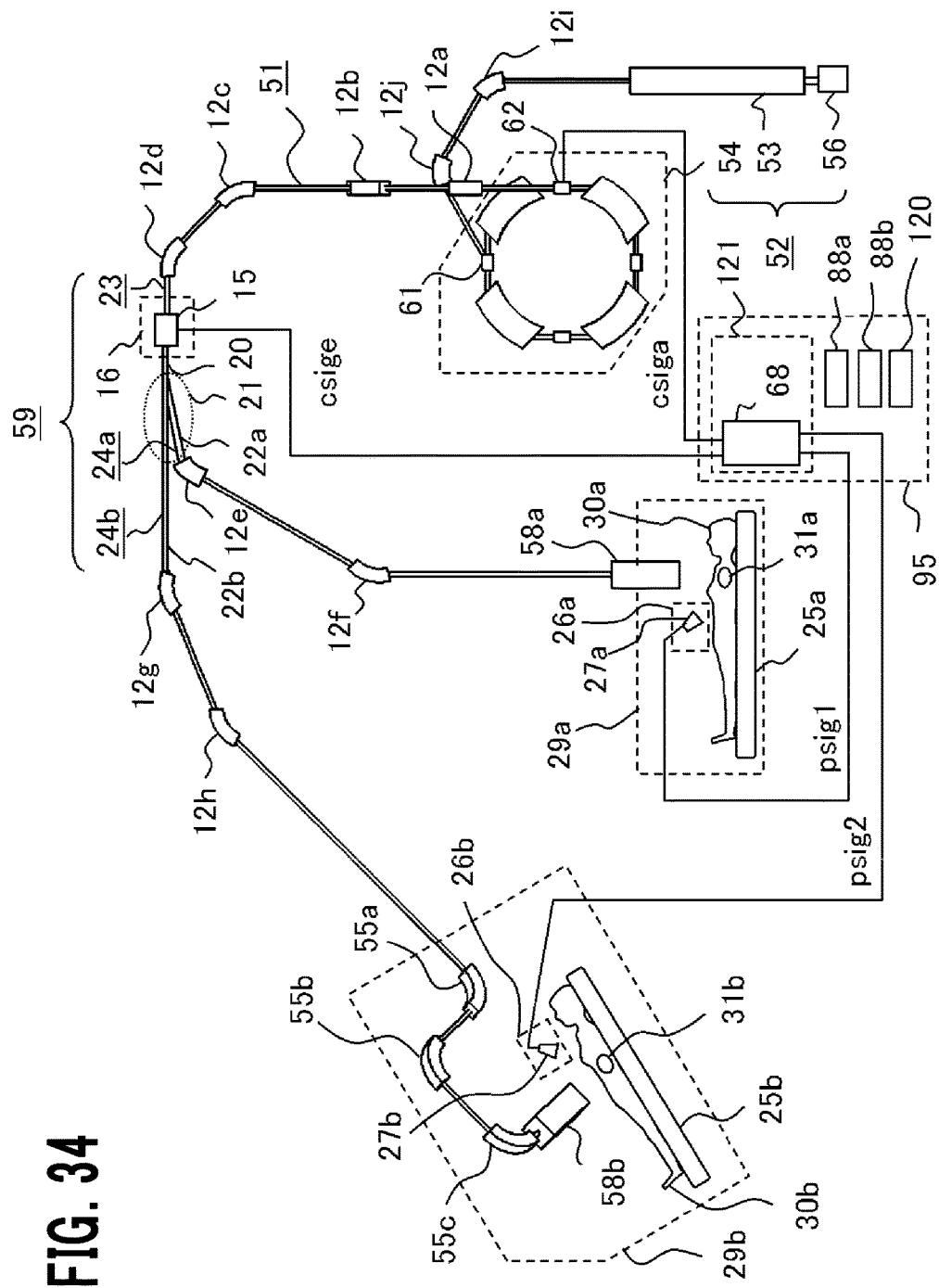
FIG. 34 is a configuration diagram showing a particle beam therapy system according to Embodiment 8 of the invention.
Figure 35:
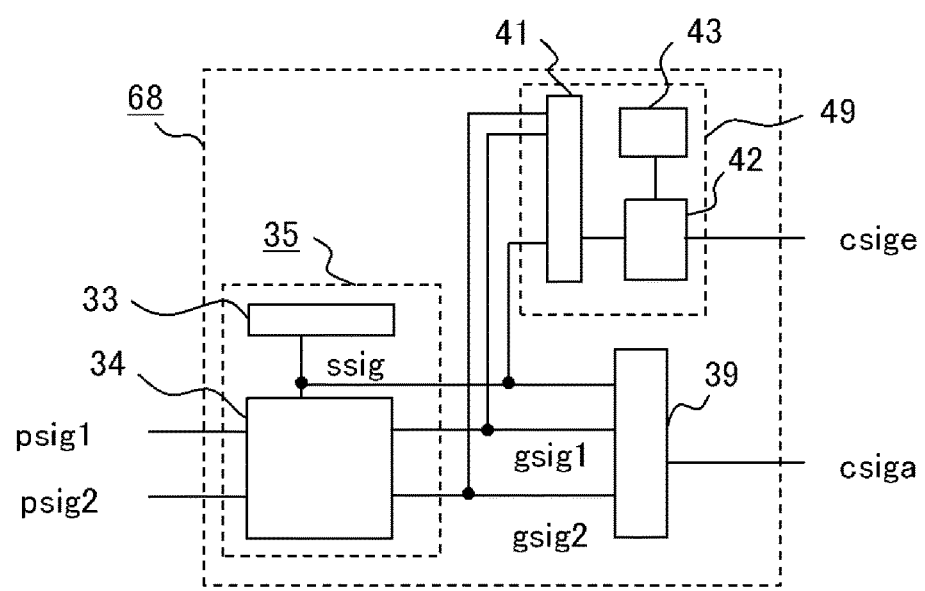
FIG. 35 is a diagram showing a beam-path controller in FIG. 34.
Figure 36:
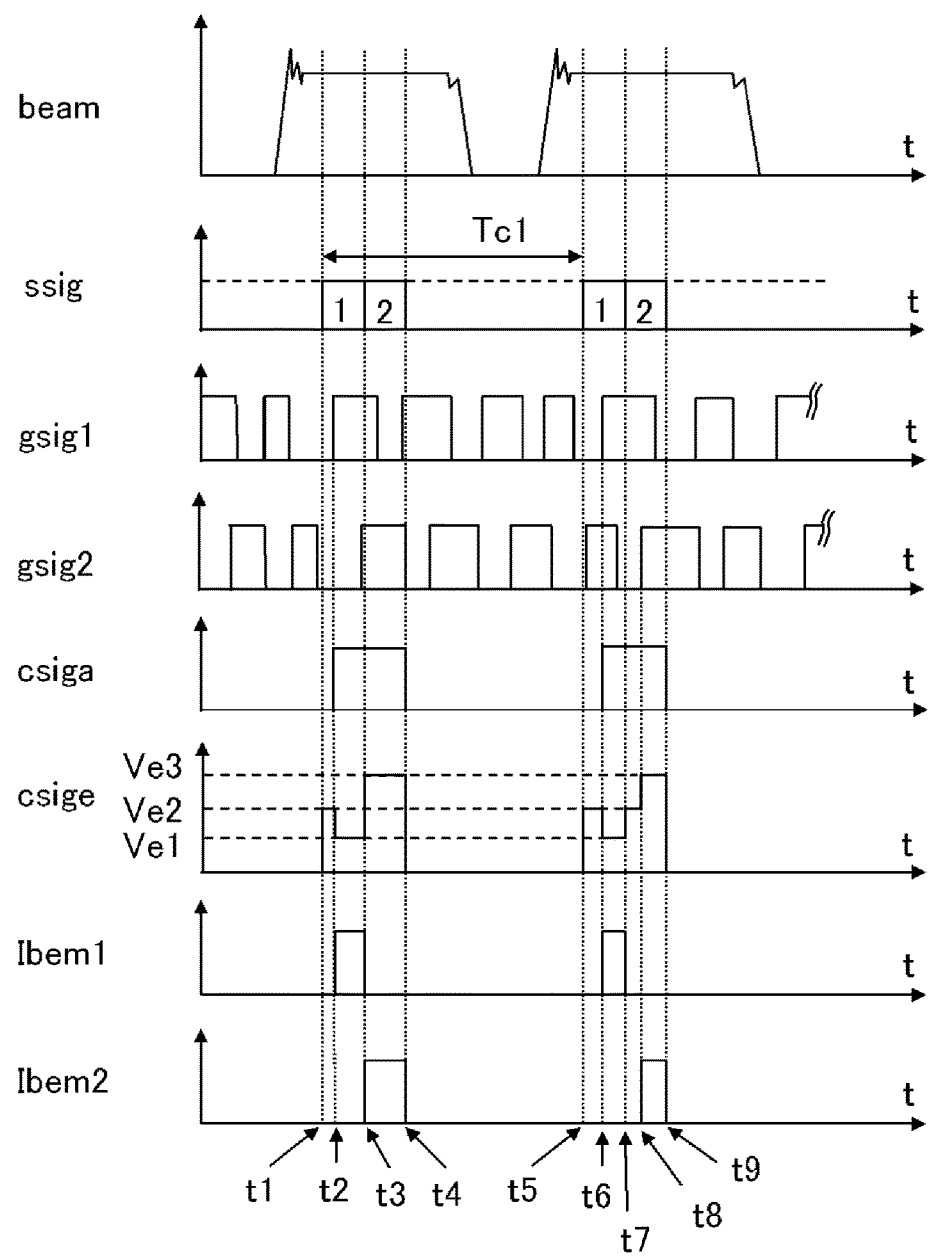
FIG. 36 is a timing chart illustrating a beam distribution to a plurality of treatment rooms according to Embodiment 8 of the invention.

In Embodiment 8, such a case will be shown where, in the particle beam therapy system 51 of Embodiment 2 provided with the damper 11 in the beam transport system 59, the beam deflector 15 is used, thereby to achieve rapid switching of the beam path and to allow the particle beam therapy system to be designed compact. FIG. 34 is a configuration diagram showing a particle beam therapy system according to Embodiment 8 of the invention, and FIG. 35 is a diagram showing a beam-path controller in FIG. 34. FIG. 36 is a timing chart illustrating a beam distribution to a plurality of treatment rooms according to Embodiment 8 of the invention. The particle beam therapy system 51 of Embodiment 8 differs from that of Embodiment 2 in that the beam deflector 15 is used as the beam-path changer 16 and the treatment management device 95 includes a beam-path controller 68 that outputs a beam-deflector control signal csige (beam-path changer control signal) for controlling the beam deflector 15.

The beam-path controller 68 includes: a time-sharing signal generator 33 for generating the time-sharing signal ssig; a respiratory gate-signal generator 34 for generating the respiratory gate signals gsig1, gsig2; an emitter control-signal generator 39 for generating the emitter control signal csiga; and a beam-deflector control-signal generator (beam-path changer control-signal generator) 49 for generating the beam-deflector control signal csige. The time-sharing signal generator 33 and the respiratory gate-signal generator 34 constitute a control signal generator 35. The beam-deflector control-signal generator 49 includes a pulse controller 41, a high-speed switch 42 and a deflector power source 43. The pulse controller 41 in Embodiment 8 receives the respiratory gate signals gsig1, gsig2 and the time-sharing signal ssig, and outputs a generated control signal to the high-speed switch 42. The high-speed switch 42 generates the beam-deflector control signal csige according to the control signal from the pulse controller 41.

Operations of the particle beam therapy system 51 of Embodiment 8 will be described using FIG. 36. Description will be made about part of operations which differs from Embodiment 2. When the time-sharing signal ssig designates the treatment room 1 (treatment room 29a) and the respiratory gate signal gsig1 is "ON", namely, when the condition for transporting the charged particle beam 81 to the treatment room 1 (treatment room 29a) is established, the beam-path controller 68 outputs a path-1 command (signal-value Ve1 state) for ordering switching of the path so that the charged particle beam 81 is guided to the treatment room 1 (treatment room 29a). When the time-sharing signal ssig designates the treatment room 2 (treatment room 29b) and the respiratory gate signal gsig2 is "ON", namely, when the condition for transporting the charged particle beam 81 to the treatment room 2 (treatment room 29b) is established, the beam-path controller 68 outputs a path-2 command (signal-value Ve3 state) for ordering switching of the path so that the charged particle beam 81 is guided to the treatment room 2 (treatment room 29b). When the time-sharing signal ssig designates either one of the treatment rooms (treatment room 1, treatment room 2), and the respiratory gate signal (gsig1, gsig2) corresponding to that treatment room is "OFF", namely, the condition for guiding the charged particle beam 81 to the damper 11 is established, the beam-path controller 68 outputs a path-3 command (signal-value Ve2 state) for ordering switching of the path so that the charged particle beam 81 is guided to the damper 11.

Here, the signal value Ve3 (voltage Ve3) is the voltage Vb applied to the electrode plate 76, and the signal value Ve1 (voltage Ve1) and the signal value Ve2 (voltage Ve2) are each a voltage lower than Ve3. Although the magnitude relationship between the signal values Ve1, Ve3 of the beam-deflector control signal csige is reversed from the magnitude relationship between the signal values Id1, Id3 of the kicker control signal csigd in Embodiment 2, as described above, the path-1 command is provided when the beam-deflector control signal csige has the signal value Ve1, the path-2 command is provided when the beam-deflector control signal csige has the signal value Ve3, and the path-3 command is provided when the beam-deflector control signal csige has the signal value Ve2. Accordingly, the particle beam therapy system 51 of Embodiment 8 operates similarly to in Embodiment 2.

The particle beam therapy system 51 of Embodiment 8 achieves the same effect as in Embodiment 2. Further, the particle beam therapy system 51 of Embodiment 8 is configured to use, in place of the kicker electromagnet 10 in Embodiment 2, the beam deflector 15 that is able to switch the beam path faster and to make the deflection angle larger, than the kicker electromagnet 10, so that the particle beam therapy system can be designed compact while achieving more rapid switching of the beam path than that in Embodiment 2.

Embodiment 9

Figure 37:
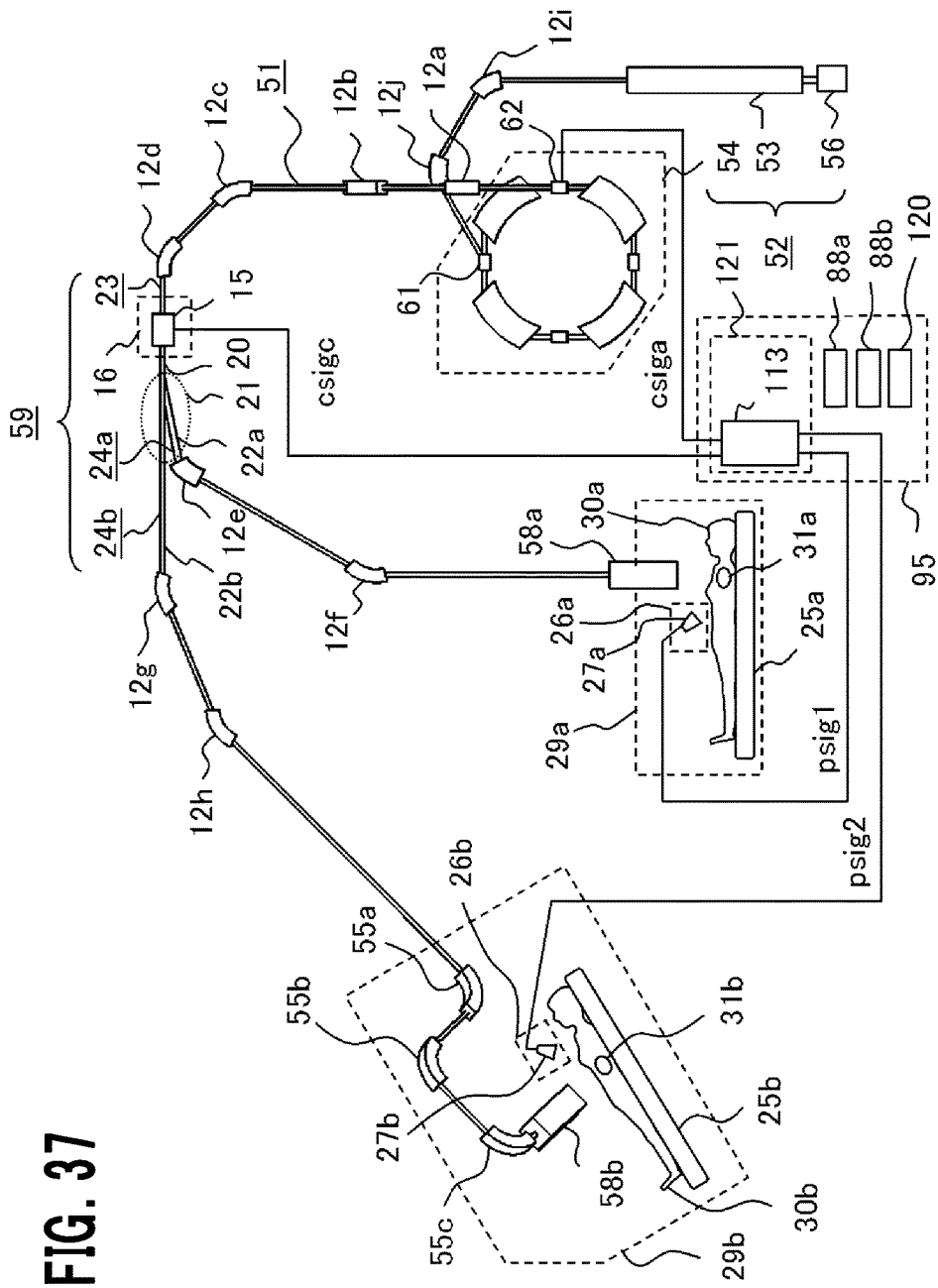
FIG. 37 is a configuration diagram showing a particle beam therapy system according to Embodiment 9 of the invention.
Figure 38:
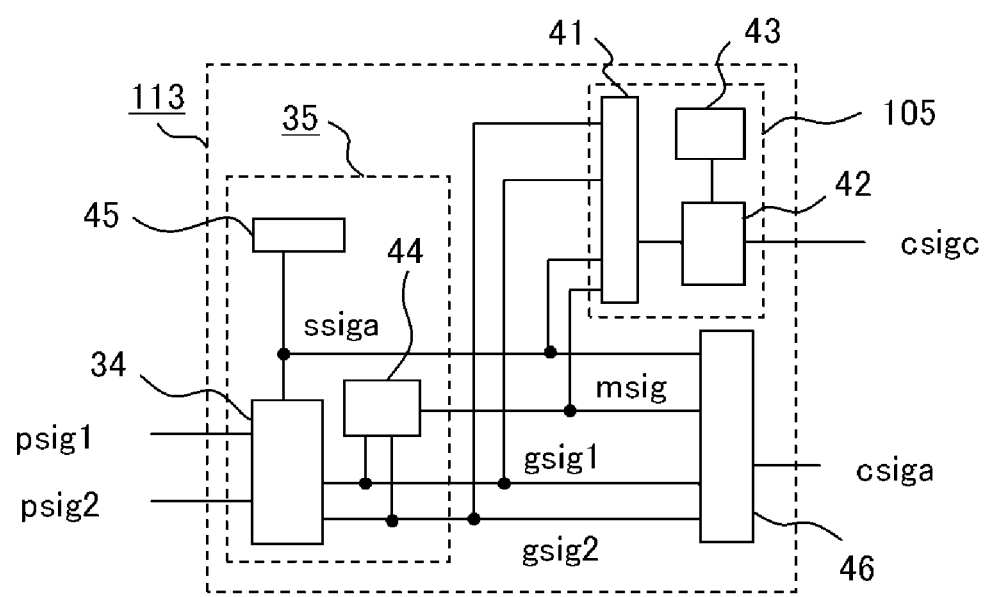
FIG. 38 is a diagram showing a beam-path controller in FIG. 37.
Figure 39:
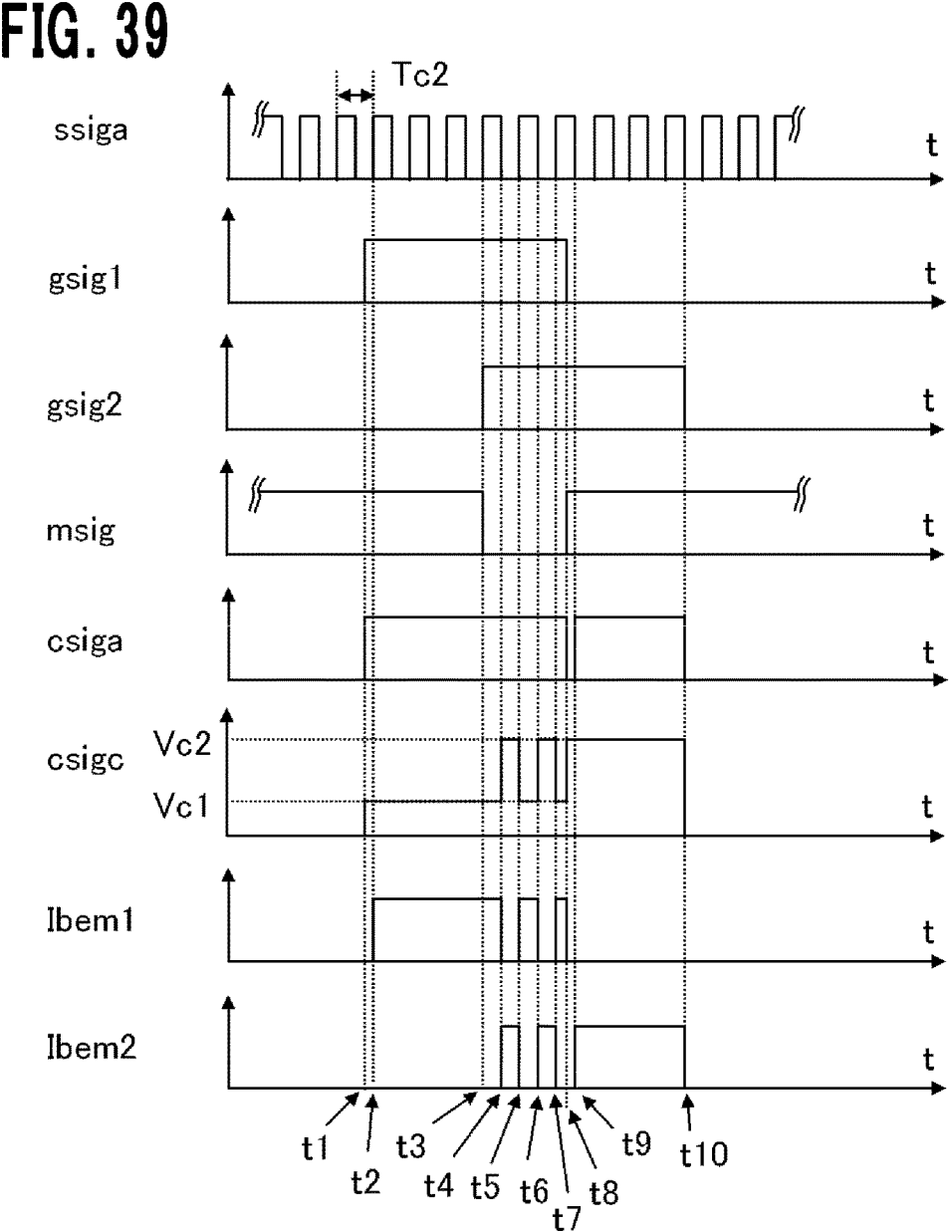
FIG. 39 is a timing chart illustrating a beam distribution to a plurality of treatment rooms according to Embodiment 9 of the invention.

In Embodiment 9, such a case will be shown where, in the particle beam therapy system 51 in Embodiment 3 in which, when irradiation requests from the plurality of treatment rooms 29 are overlapping, the charged particle beam 81 is controlled to be switched between toward the respective corresponding treatment rooms 1, 2 (treatment rooms 29a, 29b) in a short time, a beam deflector 15 is used, thereby to achieve rapid switching of the beam path and to allow the particle beam therapy system to be designed compact. FIG. 37 is a configuration diagram showing a particle beam therapy system according to Embodiment 9 of the invention, and FIG. 38 is a diagram showing a beam-path controller in FIG. 37. FIG. 39 is a timing chart illustrating a beam distribution to a plurality of treatment rooms according to Embodiment 9 of the invention. The particle beam therapy system 51 of Embodiment 9 differs from that of Embodiment 3 in that the beam deflector 15 is used as the beam-path changer 16 and the treatment management device 95 includes a beam-path controller 113 that outputs a beam-deflector control signal csigc for controlling the beam deflector 15.

The beam-path controller 113 includes: an emitter control-signal generator 46 for generating an emitter control signal csiga; abeam-deflector control-signal generator (beam-path changer control signal generator) 105 for generating a beam-deflector control signal csigc; and a control signal generator 35 for outputting a plurality of control signals to the emitter control-signal generator 46 and the beam-deflector control-signal generator 105. The control signal generator 35 includes: a time-sharing signal generator 45 for generating a time-sharing signal ssiga with a cycle of Tc2 that is shorter than the cycle Tc1; a respiratory gate-signal generator 34 for generating respiratory gate signals gsig1, gsig2; and a mask signal generator 44 for generating a mask signal msig for masking a treatment-room selection by the time-sharing signal ssiga. The beam-deflector control-signal generator 105 includes a pulse controller 41, a high-speed switch 42 and a deflector power source 43. The pulse controller 41 in Embodiment 9 receives the respiratory gate signals gsig1, gsig2, the time-sharing signal ssiga and the mask signal msig, and outputs a generated control signal to the high-speed switch 42. The high-speed switch 42 generates the beam-deflector control signal csigc according to the control signal from the pulse controller 41.

Operations of the particle beam therapy system 51 of Embodiment 9 will be described using FIG. 39. Description will be made about part of operations which differs from Embodiment 3. When the condition for transporting the charged particle beam 81 to the treatment room 1 (treatment room 29a) is established, the beam-path controller 113 outputs a path-1 command (signal-value Vc1 state) for ordering switching of the path so that the charged particle beam 81 is guided to the treatment room 1 (treatment room 29a). When the condition for transporting the charged particle beam 81 to the treatment room 2 (treatment room 29b) is established, the beam-path controller 113 outputs a path-2 command (signal-value Vc2 state) for ordering switching of the path so that the charged particle beam 81 is guided to the treatment room 2 (treatment room 29b). Here, the signal values Vc1, Vc2 are just as described in Embodiment 7. The particle beam therapy system 51 of Embodiment 9 operates similarly to in Embodiment 3.

The particle beam therapy system 51 of Embodiment 9 achieves the same effect as in Embodiment 3. Further, the particle beam therapy system 51 of Embodiment 9 is configured to use, in place of the kicker electromagnet 10 in Embodiment 3, the beam deflector 15 that is able to switch the beam path faster and to make the deflection angle larger, than the kicker electromagnet 10, so that the particle beam therapy system can be designed compact while achieving more rapid switching of the beam path than that in Embodiment 3.

Embodiment 10

Figure 40:
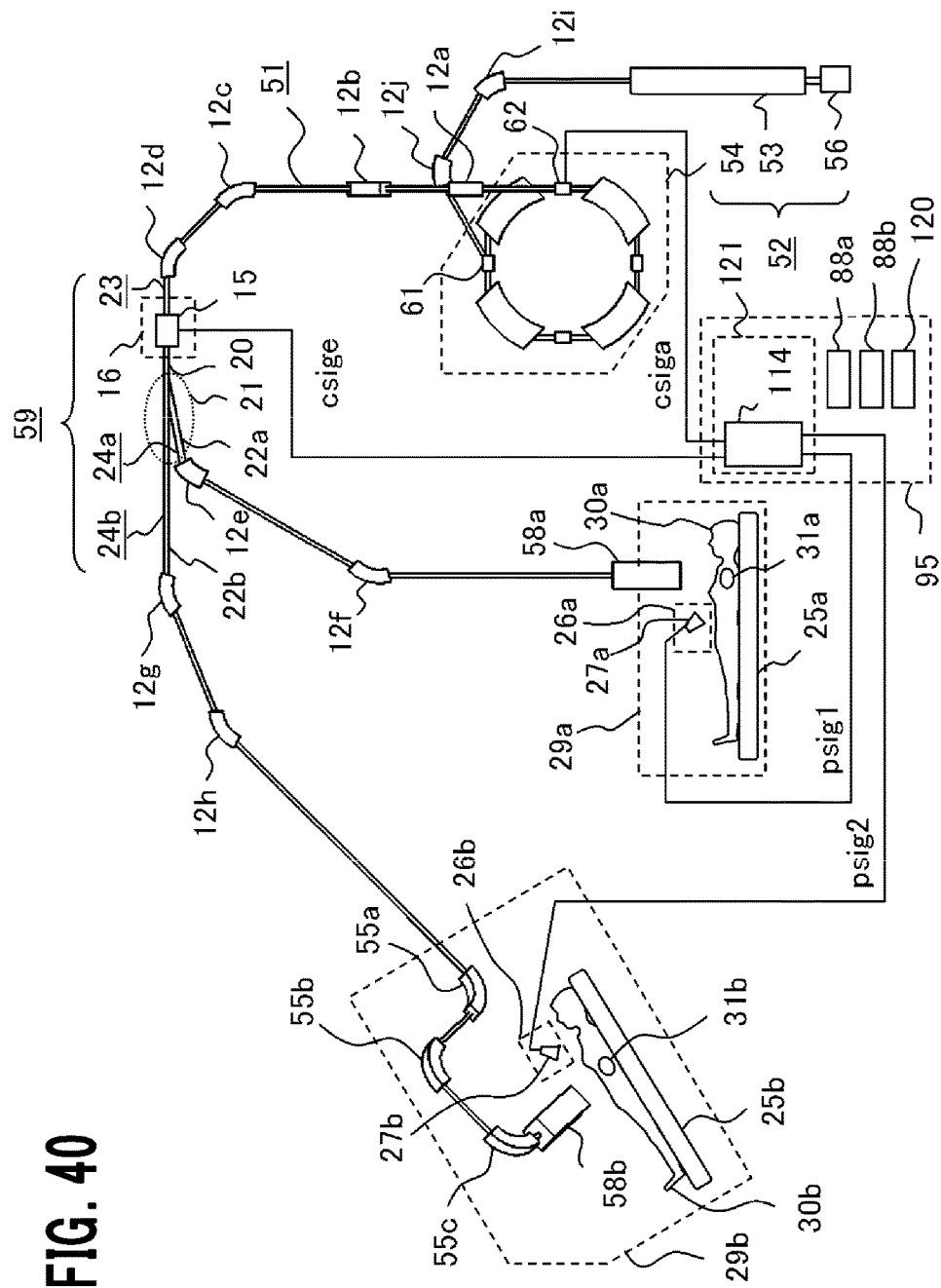
FIG. 40 is a configuration diagram showing a particle beam therapy system according to Embodiment 10 of the invention.
Figure 41:
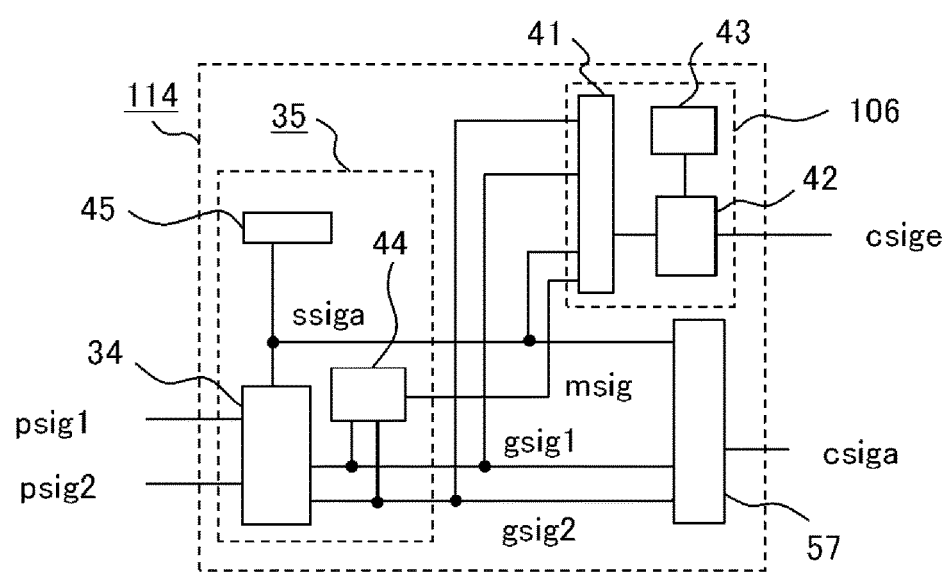
FIG. 41 is a diagram showing a beam-path controller in FIG. 40.
Figure 42:
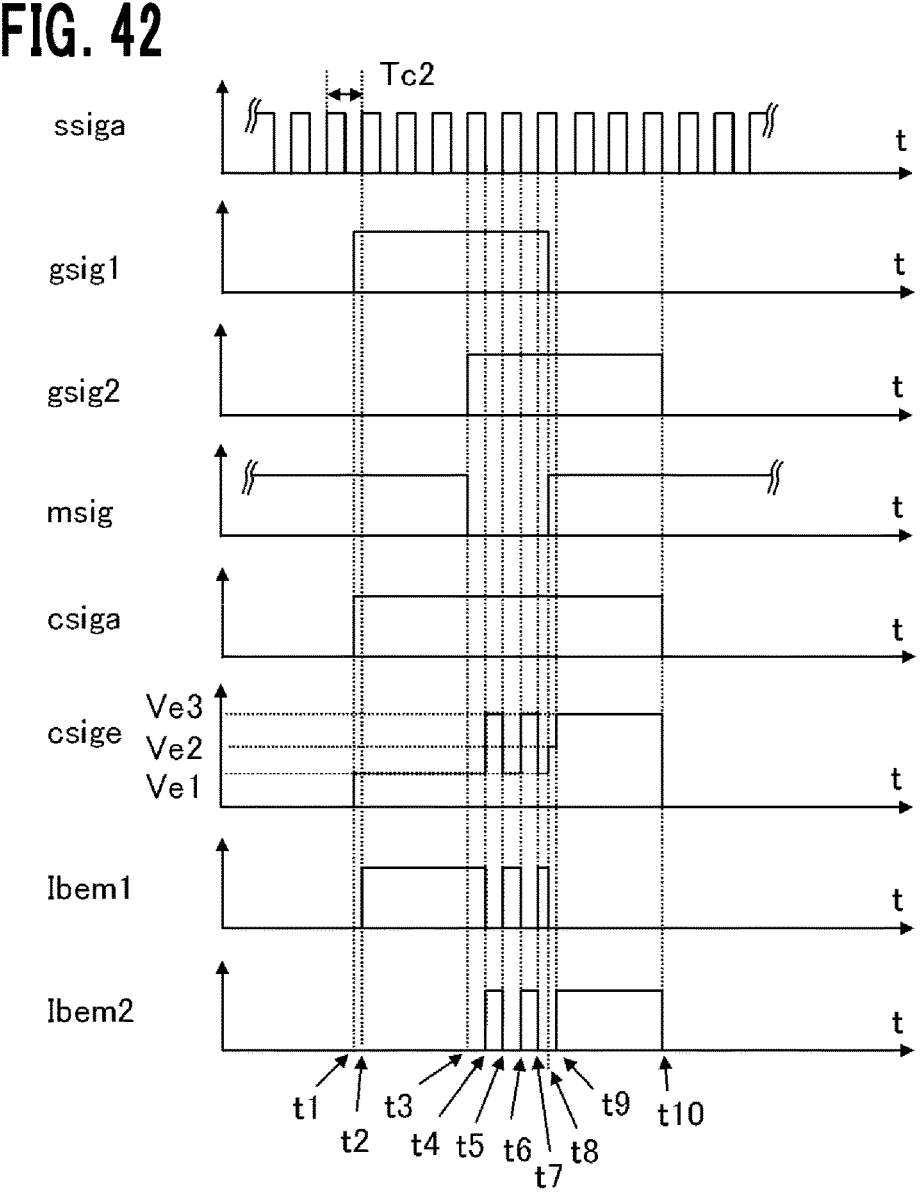
FIG. 42 is a timing chart illustrating a beam distribution to a plurality of treatment rooms according to Embodiment 10 of the invention.

In Embodiment 10, such a case will be shown where, in the particle beam therapy system 51 in Embodiment 4 which is provided with the damper 11 in the beam transport system 59 and in which, when irradiation requests from the plurality of treatment rooms 29 are overlapping, the charged particle beam 81 is controlled to be switched between toward the respective corresponding treatment rooms 1, 2 (treatment rooms 29a, 29b) in a short time, a beam deflector 15 is used, thereby to achieve rapid switching of the beam path and to allow the particle beam therapy system to be designed compact. FIG. 40 is a configuration diagram showing a particle beam therapy system according to Embodiment 10 of the invention, and FIG. 41 is a diagram showing a beam-path controller in FIG. 40. FIG. 42 is a timing chart illustrating a beam distribution to a plurality of treatment rooms according to Embodiment 10 of the invention. The particle beam therapy system 51 of Embodiment 10 differs from that of Embodiment 4 in that the beam deflector 15 is used as the beam-path changer 16 and the treatment management device 95 includes a beam-path controller 114 that outputs a beam-deflector control signal csige for controlling the beam deflector 15.

The beam-path controller 114 includes: an emitter control-signal generator 57 for generating an emitter control signal csiga; a beam-deflector control-signal generator (beam-path changer control-signal generator) 106 for generating a beam-deflector control signal csige; and a control signal generator 35 for outputting a plurality of control signals to the emitter control-signal generator 57 and the beam-deflector control-signal generator 106. The control signal generator 35 includes: a time-sharing signal generator 45 for generating a time-sharing signal ssiga with a cycle of Tc2 that is shorter than the cycle Tc1; a respiratory gate-signal generator 34 for generating respiratory gate signals gsig1, gsig2; and a mask signal generator 44 for generating a mask signal msig for masking a treatment-room selection by the time-sharing signal ssiga. The beam-deflector control-signal generator 106 includes a pulse controller 41, a high-speed switch 42 and a deflector power source 43. The pulse controller 41 in Embodiment 10 receives the respiratory gate signals gsig1, gsig2, the time-sharing signal ssiga and the mask signal msig, and outputs a generated control signal to the high-speed switch 42. The high-speed switch 42 generates the beam-deflector control signal csige according to the control signal from the pulse controller 41.

Operations of the particle beam therapy system 51 of Embodiment 10 will be described using FIG. 42. Description will be made about part of operations which differs from Embodiment 4. When the condition for transporting the charged particle beam 81 to the treatment room 1 (treatment room 29a) is established, the beam-path controller 114 outputs a path-1 command (signal-value Ve1 state) for ordering switching of the path so that the charged particle beam 81 is guided to the treatment room 1 (treatment room 29a). When the condition for transporting the charged particle beam 81 to the treatment room 2 (treatment room 29b) is established, the beam-path controller 114 outputs a path-2 command (signal-value Ve3 state) for ordering switching of the path so that the charged particle beam 81 is guided to the treatment room 2 (treatment room 29b). When the condition for guiding the charged particle beam 81 to the damper 11 is established, the beam-path controller 114 outputs a path-3 command (signal-value Ve2 state) for ordering switching of the path so that the charged particle beam 81 is guided to the damper 11. Here, the signal values Ve1, Ve2, Ve3 are just as described in Embodiment 8. The particle beam therapy system 51 of Embodiment 10 operates similarly to in Embodiment 4.

The particle beam therapy system 51 of Embodiment 10 achieves the same effect as in Embodiment 4. Further, the particle beam therapy system 51 of Embodiment 10 is configured to use, in place of the kicker electromagnet 10 in Embodiment 4, the beam deflector 15 that is able to switch the beam path faster and to make the deflection angle larger, than the kicker electromagnet 10, so that the particle beam therapy system can be designed compact while achieving more rapid switching of the beam path than that in Embodiment 4.

Embodiment 11

Figure 43:
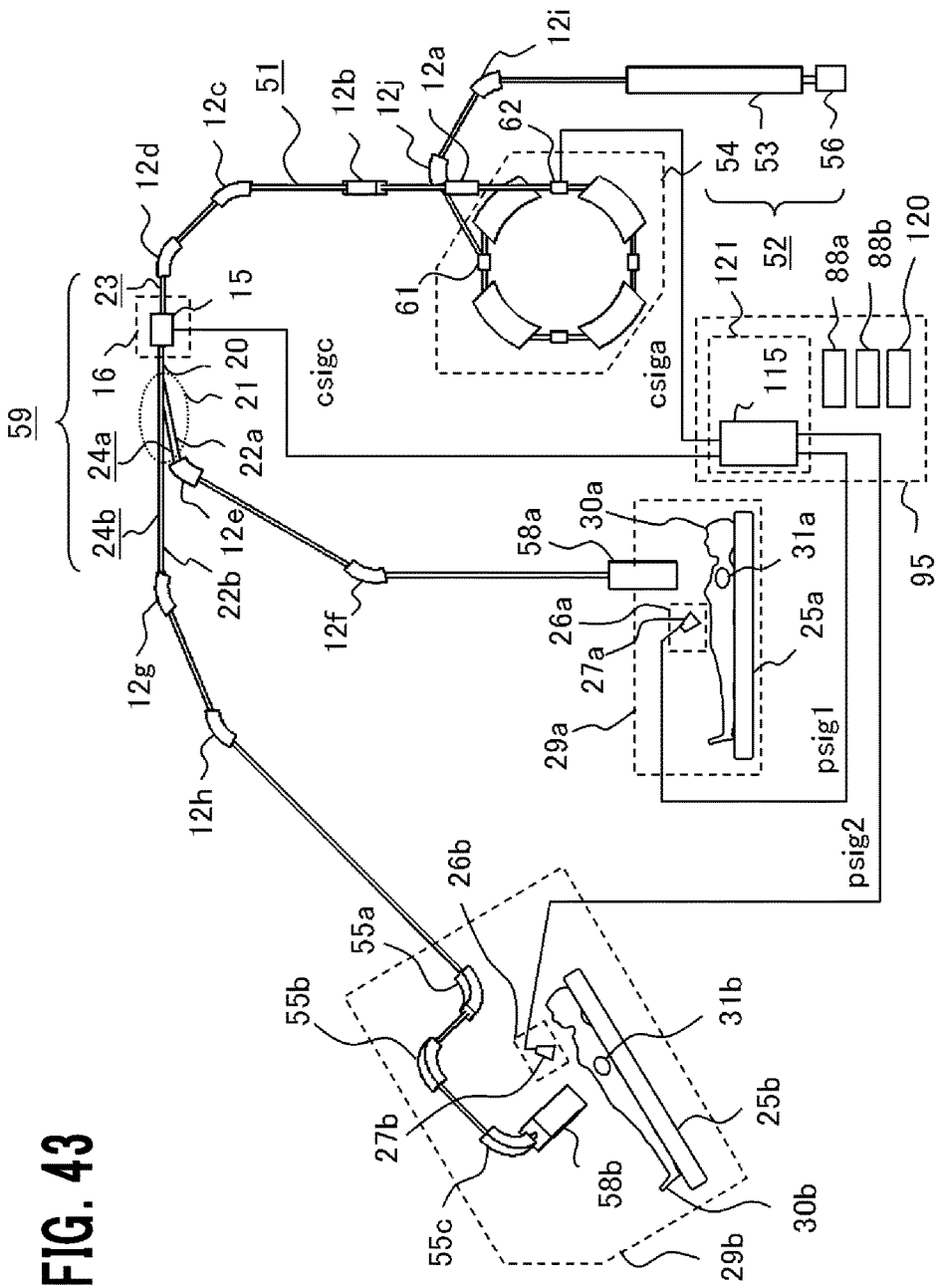
FIG. 43 is a configuration diagram showing a particle beam therapy system according to Embodiment 11 of the invention.
Figure 44:
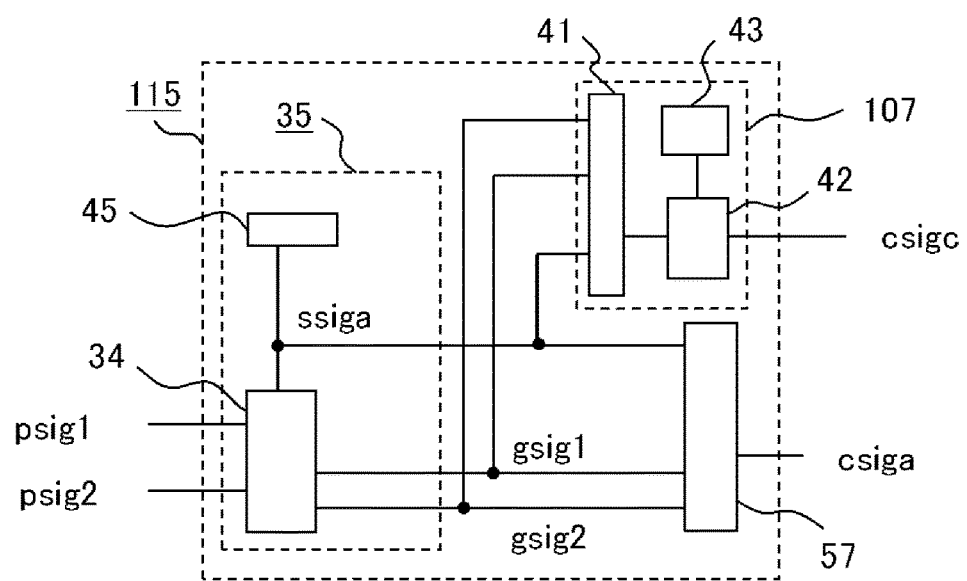
FIG. 44 is a diagram showing a beam-path controller in FIG. 43.
Figure 45:
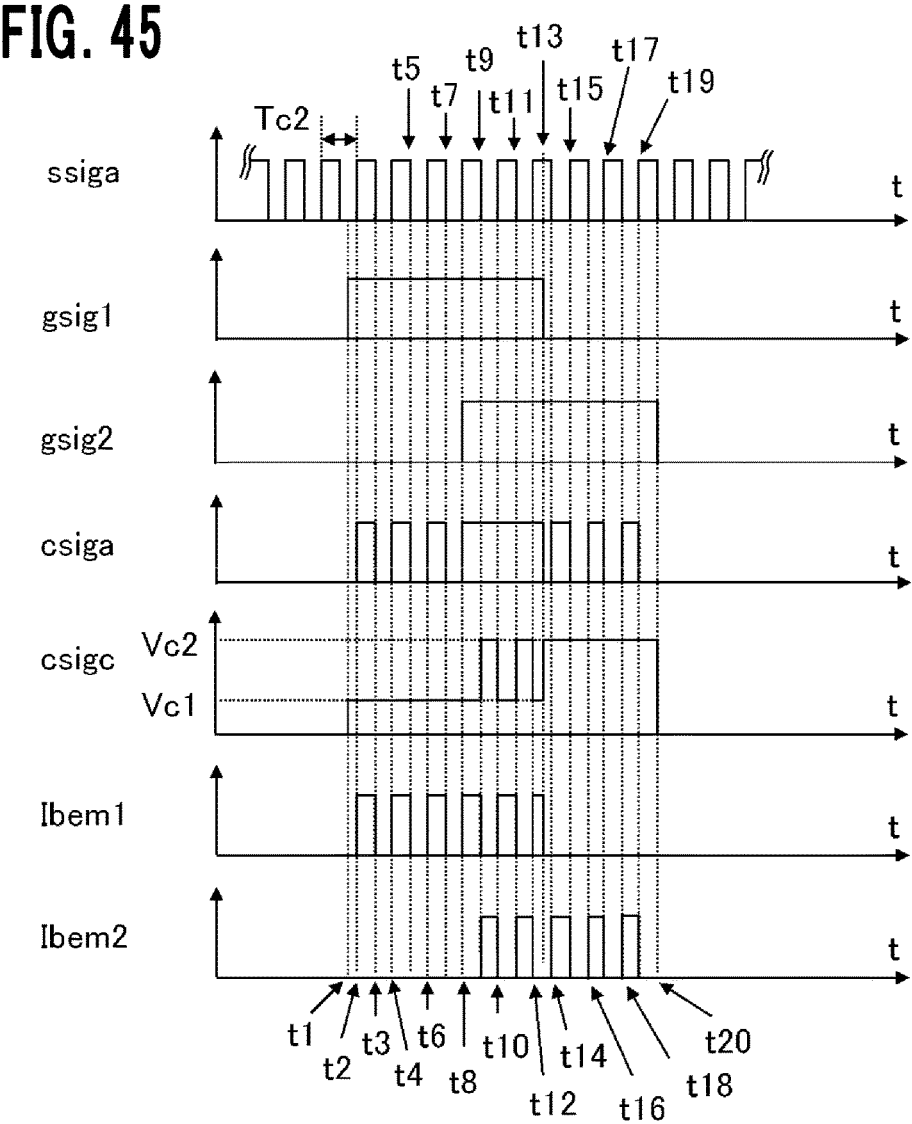
FIG. 45 is a timing chart illustrating a beam distribution to a plurality of treatment rooms according to Embodiment 11 of the invention.

In Embodiment 11, such a case will be shown where, in the particle beam therapy system 51 of Embodiment 5 in which, when irradiation requests from the plurality of treatment rooms 29 are overlapping, the charged particle beam 81 is controlled to be switched between toward the respective corresponding treatment rooms 1, 2 (treatment rooms 29a, 29b) without using the mask signal msig in a short time, a beam deflector 15 is used, thereby to achieve rapid switching of the beam path and to allow the particle beam therapy system to be designed compact. FIG. 43 is a configuration diagram showing a particle beam therapy system according to Embodiment 11 of the invention, and FIG. 44 is a diagram showing a beam-path controller in FIG. 43. FIG. 45 is a timing chart illustrating a beam distribution to a plurality of treatment rooms according to Embodiment 11 of the invention. The particle beam therapy system 51 of Embodiment 11 differs from that of Embodiment 5 in that the beam deflector 15 is used as the beam-path changer 16 and the treatment management device 95 includes a beam-path controller 115 that outputs a beam-deflector control signal csigc for controlling the beam deflector 15.

The beam-path controller 115 includes: an emitter control-signal generator 57 for generating an emitter control signal csiga; a beam-deflector control-signal generator (beam-path changer control-signal generator) 107 for generating a beam-deflector control signal csigc; and a control signal generator 35 for outputting a plurality of control signals to the emitter control-signal generator 57 and the beam-deflector control-signal generator 107. The control signal generator 35 includes: a time-sharing signal generator 45 for generating a time-sharing signal ssiga with a cycle of Tc2 that is shorter than the cycle Tc1; and a respiratory gate-signal generator 34 for generating respiratory gate signals gsig1, gsig2. The beam-deflector control-signal generator 107 includes a pulse controller 41, a high-speed switch 42 and a deflector power source 43. The pulse controller 41 in Embodiment 11 receives the respiratory gate signals gsig1, gsig2 and the time-sharing signal ssiga, and outputs a generated control signal to the high-speed switch 42. The high-speed switch 42 generates the beam-deflector control signal csigc according to the control signal from the pulse controller 41.

Operations of the particle beam therapy system 51 of Embodiment 11 will be described using FIG. 45. Description will be made about part of operations which differs from Embodiment 5. When the condition for transporting the charged particle beam 81 to the treatment room 1 (treatment room 29a) is established, the beam-path controller 115 outputs a path-1 command (signal-value Vc1 state) for ordering switching of the path so that the charged particle beam 81 is guided to the treatment room 1 (treatment room 29a). When the condition for transporting the charged particle beam 81 to the treatment room 2 (treatment room 29b) is established, the beam-path controller 115 outputs a path-2 command (signal-value Vc2 state) for ordering switching of the path so that the charged particle beam 81 is guided to the treatment room 2 (treatment room 29b). Here, the signal values Vc1, Vc2 are just as described in Embodiment 7. The particle beam therapy system 51 of Embodiment 11 operates similarly to in Embodiment 5.

The particle beam therapy system 51 of Embodiment 11 achieves the same effect as in Embodiment 5. Further, the particle beam therapy system 51 of Embodiment 11 is configured to use, in place of the kicker electromagnet 10 in Embodiment 5, the beam deflector 15 that is able to switch the beam path faster and to make the deflection angle larger, than the kicker electromagnet 10, so that the particle beam therapy system can be designed compact while achieving more rapid switching of the beam path than that in Embodiment 5.

Embodiment 12

Figure 46:
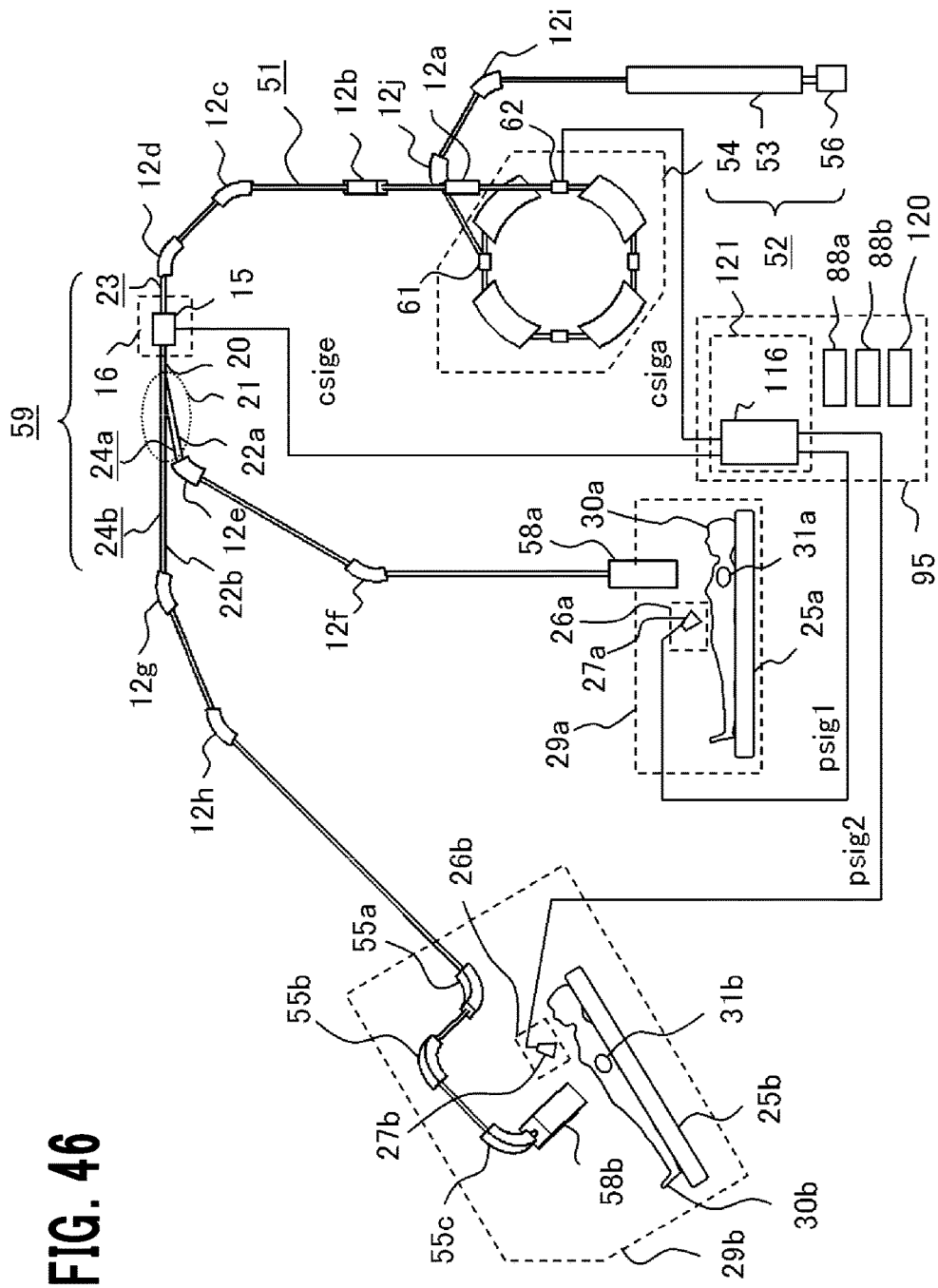
FIG. 46 is a configuration diagram showing a particle beam therapy system according to Embodiment 12 of the invention.
Figure 47:
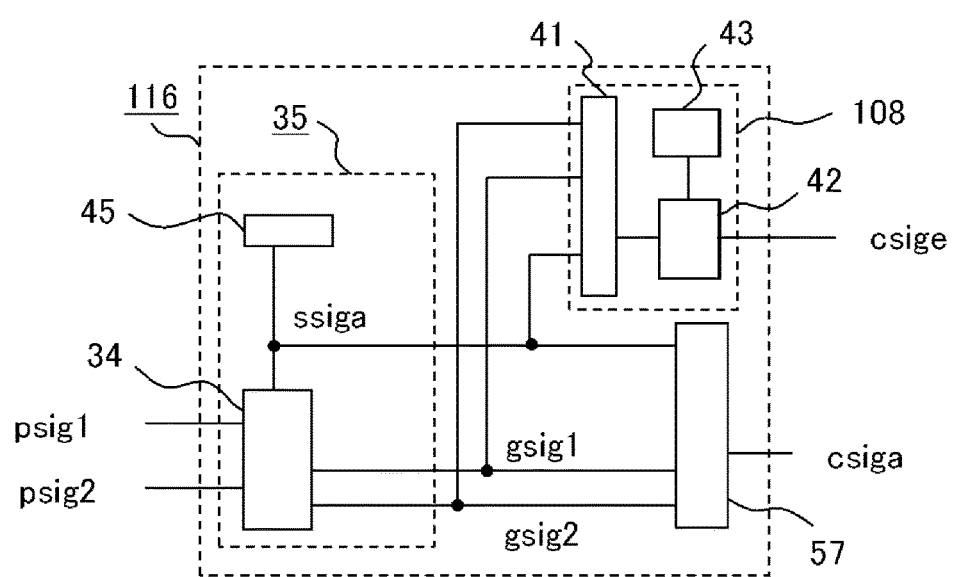
FIG. 47 is a diagram showing a beam-path controller in FIG. 46.

In Embodiment 12, such a case will be shown where, in the particle beam therapy system 51 in Embodiment 6 which is provided with the damper 11 in the beam transport system 59 and in which, when irradiation requests from the plurality of treatment rooms 29 are overlapping, the charged particle beam 81 is controlled to be switched between toward the respective corresponding treatment rooms 1, 2 (treatment rooms 29a, 29b) in a short time without using the mask signal msig, a beam deflector 15 is used, thereby to achieve rapid switching of the beam path and to allow the particle beam therapy system to be designed compact. FIG. 46 is a configuration diagram showing a particle beam therapy system according to Embodiment 12 of the invention, and FIG. 47 is a diagram showing a beam-path controller in FIG. 46. FIG. 48 is a timing chart illustrating a beam distribution to a plurality of treatment rooms according to Embodiment 12 of the invention. The particle beam therapy system 51 of Embodiment 12 differs from that of Embodiment 6 in that the beam deflector 15 is used as the beam-path changer 16 and the treatment management device 95 includes a beam-path controller 116 that outputs a beam-deflector control signal csige for controlling the beam deflector 15.

The beam-path controller 116 includes: an emitter control-signal generator 57 for generating an emitter control signal csiga; a beam-deflector control-signal generator (beam-path changer control-signal generator) 108 for generating the beam-deflector control signal csige; and a control signal generator 35 for outputting a plurality of control signals to the emitter control-signal generator 57 and the beam-deflector control-signal generator 108. The control signal generator 35 includes: a time-sharing signal generator 45 for generating a time-sharing signal ssiga with a cycle of Tc2 that is shorter than the cycle Tc1; and a respiratory gate-signal generator 34 for generating respiratory gate signals gsig1, gsig2. The beam-deflector control-signal generator 108 includes a pulse controller 41, a high-speed switch 42 and a deflector power source 43. The pulse controller 41 in Embodiment 12 receives the respiratory gate signals gsig1, gsig2 and the time-sharing signal ssiga, and outputs a generated control signal to the high-speed switch 42. The high-speed switch 42 generates the beam-deflector control signal csige according to the control signal from the pulse controller 41.

Operations of the particle beam therapy system 51 of Embodiment 12 will be described using FIG. 48. Description will be made about part of operations which differs from Embodiment 6. When the condition for transporting the charged particle beam 81 to the treatment room 1 (treatment room 29a) is established, the beam-path controller 116 outputs a path-1 command (signal-value Ve1 state) for ordering switching of the path so that the charged particle beam 81 is guided to the treatment room 1 (treatment room 29a). When the condition for transporting the charged particle beam 81 to the treatment room 2 (treatment room 29b) is established, the beam-path controller 116 outputs a path-2 command (signal-value Ve3 state) for ordering switching of the path so that the charged particle beam 81 is guided to the treatment room 2 (treatment room 29b). When the condition for guiding the charged particle beam 81 to the damper 11 is established, the beam-path controller 116 outputs a path-3 command (signal-value Ve2 state) for ordering switching of the path so that the charged particle beam 81 is guided to the damper 11. Here, the signal values Ve1, Ve2, Ve3 are just as described in Embodiment 8. The particle beam therapy system 51 of Embodiment 12 operates similarly to in Embodiment 6.

The particle beam therapy system 51 of Embodiment 12 achieves the same effect as in Embodiment 6. Further, the particle beam therapy system 51 of Embodiment 12 is configured to use, in place of the kicker electromagnet 10 in Embodiment 6, the beam deflector 15 that is able to switch the beam path faster and to make the deflection angle larger, than the kicker electromagnet 10, so that the particle beam therapy system can be designed compact while achieving more rapid switching of the beam path than that in Embodiment 6.

It should be noted that, in Embodiments 1 to 12, the description has been made citing the irradiation method in which the charged particle beam 81 is stopped at the time of changing the slice but the charged particle beam 81 is continued to be radiated at the time of irradiation within the same slice; however, the invention is not limited thereto, and may be applied to another method of, such as a spot scanning in which the charged particle beam 81 is stopped on each irradiation-spot basis, a raster scanning, or the like. Further, in the present invention, any combination of the respective embodiments and any appropriate modification or omission in the embodiments may be made without departing from the scope of the invention.

DESCRIPTION OF REFERENCE NUMERALS AND SIGNS

10: kicker electromagnet, 11, 11a, 11b: damper, 15: beam deflector, 16: beam-path changer, 18, 19: beam-path controller, 29, 29a, 29b: treatment room, 30, 30a, 30b: patient, 33: time-sharing signal generator, 36: emitter control-signal generator, 37: kicker control-signal generator (beam-path changer control-signal generator), 39: emitter control-signal generator, 40: kicker control-signal generator (beam-path changer control-signal generator), 41: pulse controller, 42: high-speed switch, 43: deflector power source, 44: mask signal generator, 45: time-sharing signal generator, 46: emitter control-signal generator, 47: kicker control-signal generator (beam-path changer control-signal generator), 48, 49: beam-deflector control-signal generator (beam-path changer control-signal generator), 50: kicker control-signal generator (beam-path changer control-signal generator), 51: particle beam therapy system, 54: circular accelerator (accelerator), 57: emitter control-signal generator, 58, 58a, 58b: particle beam irradiation apparatus, 59: beam transport system, 60: kicker control-signal generator (beam-path changer control-signal generator), 62: emitter, 63, 64, 65, 66, 67, 68: beam-path controller, 69: kicker control-signal generator (beam-path changer control-signal generator), 74: line electrode plate, 75: backside conductor, 76: electrode plate, 77, 77a, 77b, 77c, 77d, 77e, 77f: conductive plate, 81: charged particle beam, 95: treatment management device, 97: voltage pulse, 105, 106, 107, 108: beam-deflector control-signal generator (beam-path changer control-signal generator), 113, 114, 115, 116: beam-path controller, csiga: emitter control signal, csigb: kicker control signal (beam-path changer control signal), csigc: beam-deflector control signal (beam-path changer control signal), csigd: kicker control signal (beam-path changer control signal), csige: beam-deflector control signal (beam-path changer control signal), gsig1, gsig2, gsig3: respiratory gate signal, msig: mask signal, ssig, ssiga: time-sharing signal, TV0: transmission base time, TP0: particle-movement base time.

The invention claimed is:

1. A particle beam therapy system, comprising:
a plurality of treatment rooms;
a plurality of particle beam irradiation apparatuses placed respectively in the plurality of treatment rooms;
an accelerator that accelerates a charged particle beam; and
a beam transport system that transports the charged particle beam accelerated by the accelerator to the plurality of particle beam irradiation apparatuses;
wherein the beam transport system includes a beam-path changer for changing a beam path so as to transport the charged particle beam to any one of the plurality of particle beam irradiation apparatuses;
wherein the accelerator comprises an emitter;
wherein the emitter is configured to receive an emitter control signal and the beam-path changer is configured to receive a beam-path changer control signal so that, with respect to the plurality of particle beam irradiation apparatuses in which treatment is performed at a same treatment period of time, the charged particle beam is transported to each one of the plurality of particle beam irradiation apparatuses for each time period allocated thereto; and
wherein, with respect to a plurality of respiration gate signals for permitting radiation of the charged particle beam that are generated, from individual monitoring of respiratory states of a plurality of patients to be irradiated with the charged particle beam by the plurality of particle beam irradiation apparatuses, respectively for the plurality of patients, when at least two of the plurality of respiration gate signals become simultaneously "ON", the emitter, based on the emitter control signal, and the beam-path changer, based on the beam-path changer control signal, operate so that the charged particle beam is transported, without depending on the plurality of respiratory gate signals, to the particle beam irradiation apparatus in the treatment room designated by a time-sharing signal for cyclically selecting each one of the plurality of particle beam irradiation apparatuses, on the basis of the plurality of respiratory gate signals and the time-sharing signal.

2. The particle beam therapy system of claim 1, wherein the beam-path changer control signal comprises a signal by which a path command for transporting the charged particle beam to a designated one of the treatment rooms is changed according to a treatment-room designation in the time-sharing signal; and wherein the emitter control signal comprises one of:
in a case where the respiratory gate signal corresponding to the treatment room designated by the time time-sharing signal is "ON", a signal indicative of an emission command for ordering emission of the charged particle beam; and
in another case, a signal indicative of an emission stop command for ordering stopping of emission of the charged particle beam.

3. The particle beam therapy system of claim 1, wherein the beam transport system is provided with a damper for shutting off the charged particle beam, at a downstream side of the beam-path changer; and wherein
the beam-path changer control signal comprises one of:
in a case where the respiratory gate signal corresponding to the treatment room designated by the time-sharing signal is "ON", a signal indicative of a path command for transporting the charged particle beam to the treatment room that meets such a condition; and
in a case where the respiratory gate signal corresponding to the treatment room designated by the time-sharing signal is "OFF", a signal indicative of a path shutoff command for guiding the charged particle beam to the damper; and wherein the emitter control signal comprises one of:
in a case where the respiratory gate signal corresponding to a treatment-room designation designated in every cycle of the time-sharing signal is "ON", a signal indicative of an emission command for ordering emission of the charged particle beam; and
in a case where the emission command is once generated and, in that cycle, a last treatment-room designation is cancelled thereafter, a signal indicative of an emission stop command for ordering stopping of emission of the charged particle beam.

4. The particle beam therapy system of claim 1, further comprising:
a time-sharing signal generator that generates the time-sharing signal, said time-sharing signal having a cycle by which a treatment-room designation is changed two or more times during continuing of "ON" state of the respiratory gate signal; and
a mask signal generator that generates a mask signal for masking the treatment-room designation by the time-sharing signal;
wherein the emitter control signal is based on the plurality of respiration gate signals, the mask signal and the time-sharing signal;
wherein the beam-path changer control signal is based on the plurality of respiration gate signals, the mask signal and the time-sharing signal;

wherein the emitter control signal comprises one of:
in a case where the mask signal indicates a masking command and the respiratory gate signal is "ON", a signal indicative of an emission command for ordering emission of the charged particle beam;
in a case where the mask signal indicates a mask cancelling command and the treatment room corresponding to the respiratory gate signal of "ON" is designated by the time-sharing signal, a signal indicative of an emission command for ordering emission of the charged particle beam; and
in another case, a signal indicative of an emission stop command for ordering stopping of emission of the charged particle beam; and wherein the beam-path changer control signal comprises one of:
in a case where the mask signal indicates a masking command and only one of the plurality of respiratory gate signals is "ON", a signal indicative of a path command for transporting the charged particle beam to the treatment room that meets such a condition; and
in a case where the mask signal indicates a mask cancelling command, at least two of the plurality of respiratory gate signals are simultaneously "ON", and the treatment room corresponding to the respiratory gate signal of "ON" is designated by the time-sharing signal, a signal indicative of a path command for transporting the charged particle beam to the treatment room that meets such a condition.

5. The particle beam therapy system of claim 1, wherein the beam transport system is provided with a damper for shutting off the charged particle beam at a downstream side of the beam-path changer;

wherein the particle beam therapy system further includes:
a time-sharing signal generator that generates the time-sharing signal, said time-sharing signal having a cycle by which a treatment-room designation is changed two or more times during continuing of "ON" state of the respiratory gate signal; and
a mask signal generator that generates a mask signal for masking the treatment-room designation by the time-sharing signal;
wherein the emitter control signal is based on the plurality of respiration gate signals and the time-sharing signal;
wherein the beam-path changer control signal is based on the plurality of respiration gate signals, the mask signal and the time-sharing signal;
wherein the emitter control signal comprises one of:
in a case where at least one of the plurality of respiration gate signals is "ON", a signal indicative of an emission command for ordering emission of the charges particle beam; and
in another case, a signal indicative of an emission stop command for ordering stopping of emission of the charged particle beam; and
wherein the beam-path changer control signal comprises one of:
in a case where the mask signal indicates a masking command and only one of the plurality of respiratory gate signals is "ON", a signal indicative of a path command for transporting the charged particle beam to the treatment room that meets such a condition;

in a case where the mask signal indicates a mask cancelling command and the respiratory gate signal corresponding to the treatment room designated by the time-sharing signal is "ON", a signal indicative of a path command for transporting the charged particle beam to the treatment room that meets such a condition; and in a case where the mask signal indicates a mask cancelling command and the respiratory gate signal corresponding to the treatment room designated by the time-sharing signal is "OFF", a signal indicative of a path shutoff command for guiding the charged particle beam to the damper.

6. The particle beam therapy system of claim 1, further comprising:

a time-sharing signal generator that generates the time-sharing signal, said time-sharing signal having a cycle by which a treatment-room designation is changed two or more times during continuing of "ON" state of the respiratory gate signal;

wherein the emitter control signal is based on the plurality of respiration gate signals and the time-sharing signal; and wherein the beam-path changer control signal is based on the plurality of respiration gate signals and the time-sharing signal;

wherein the emitter control signal comprises one of:

in a case where only one of the plurality of respiratory gate signals is "ON" and the treatment room corresponding to the respiratory gate signal of "ON" is designated by the time-sharing signal, a signal indicative of an emission command for ordering emission of the charged particle beam;

in a case where at least two of the plurality of respiratory gate signals are simultaneously "ON", and the treatment room corresponding to the respiratory gate signal of "ON" is designated by the time-sharing signal, a signal indicative of an emission command for ordering emission of the charged particle beam; and in another case, a signal indicative of an emission stop command for ordering stopping of emission of the charged particle beam; and wherein the beam-path changer control signal comprises one of:

in a case where only one respiratory gate signal among the plurality of respiratory gate signals is "ON", a signal indicative of a path command for transporting the charged particle beam to the treatment room corresponding to the respiratory gate signal of "ON"; and in a case where at least two of the plurality of respiratory gate signals are simultaneously "ON", and the treatment room corresponding to the respiratory gate signal of "ON" is designated by the time-sharing signal, a signal indicative of a path command for transporting the charged particle beam to the treatment room corresponding to the respiratory gate signal of "ON".

7. The particle beam therapy system of claim 1, wherein the beam transport system is provided with a damper for shutting off the charged particle beam at a downstream side of the beam-path changer;

wherein the particle beam therapy system further includes:

a time-sharing signal generator that generates the time-sharing signal, said time-sharing signal having a cycle by which a treatment-room designation is changed two or more times during continuing of "ON" state of the respiratory gate signal;

wherein the emitter control signal is based on the plurality of respiration gate signals and the time-sharing signal;

wherein the beam-path changer control signal is based on the plurality of respiration gate signals and the time-sharing signal;

wherein the emitter control signal comprises one of:

in a case where at least one of the plurality of respiration gate signals is "ON", a signal indicative of an emission command for ordering emission of the charges particle beam; and in another case, a signal indicative of an emission stop command for ordering stopping of emission of the charged particle beam; and wherein the beam-path changer control signal comprises one of:

in a case where the respiratory gate signal corresponding to the treatment room designated by the time-sharing signal is "ON", a signal indicative of a path command for transporting the charged particle beam to the treatment room that meets such a condition; and in a case where the respiratory gate signal corresponding to the treatment room designated by the time-sharing signal is "OFF", a signal indicative of a path shutoff command for guiding the charged particle beam to the damper.

8. The particle beam therapy system of claim 1, wherein the beam-path changer is a kicker electromagnet.

9. The particle beam therapy system of claim 1, further comprising:

a beam-path controller that includes a high-speed switch and a deflector power source;

wherein the beam path chancier is a beam deflector; and wherein the high-speed switch selects an output voltage of the deflector power source according to a control signal generated by the beam-path controller, to thereby generate the beam-path changer control signal.

10. The particle beam therapy system of claim 2, further comprising:

a beam-path changer control-signal generator that includes a pulse controller, a high-speed switch and a deflector power source;

wherein the beam-path chancier is a beam deflector;

wherein the pulse controller outputs to the high-speed switch, a control signal generated based on a signal inputted to the beam-path changer control-signal generator; and wherein the high-speed switch selects an output voltage of the deflector power source according to the control signal to thereby generate the beam-path changer control signal.

11. The particle beam therapy system of claim 9, wherein the beam deflector includes:

a line electrode plate in which a plurality of conductive plates are placed so that a traverse direction of each of the conductive plates is arranged along a traveling direction of the charged particle beam;

an electrode plate placed in parallel to the line electrode plate; and a passing region formed between the line electrode plate and the electrode plate through which the charged particle beam passes;

wherein the plurality of conductive plates are serially connected in their longitudinal directions, and are subjected to impedance matching; and wherein the beam-path controller outputs the beam-path changer control signal which is a voltage pulse whose transmission base time is synchronized with a particle-movement base time, said transmission base time being a transmission cycle in which the voltage pulse is transmitted through each of the plurality of conductive plates in the longitudinal direction, and said particle-movement base time being a passing cycle in which the charged particle beam passes through each of the plurality of conductive plates in the traverse direction.

12. The particle beam therapy system of claim 10, wherein the beam deflector includes:
   a line electrode plate in which a plurality of conductive plates are placed so that a traverse direction of each of the conductive plates is arranged along a traveling direction of the charged particle beam;
   an electrode plate placed in parallel to the line electrode plate; and
   a passing region formed between the line electrode plate and the electrode plate through which the charged particle beam passes;
wherein the plurality of conductive plates are serially connected in their longitudinal directions, and are subjected to impedance matching; and
wherein the beam-path changer control-signal generator outputs the beam-path changer control signal which is a voltage pulse whose transmission base time is synchronized with a particle-movement base time, said transmission base time being a transmission cycle in which the voltage pulse is transmitted through each of the plurality of conductive plates in the longitudinal direction, and said particle-movement base time being a passing cycle in which the charged particle beam passes through each of the plurality of conductive plates in the traverse direction.

13. The particle beam therapy system of claim 11, wherein the line electrode plate includes a base plate, wherein the plurality of conductive plates placed on a front-face side of the base plate, wherein a backside conductor is provided on a back-face side of the base plate is connected to a ground level; and wherein a structure of the base plate, the plurality of conductive plates and the backside conductor is a microstrip line structure.

14. The particle beam therapy system of claim 2, wherein the beam-path changer is a kicker electromagnet.

15. The particle beam therapy system of claim 3, wherein the beam-path changer is a kicker electromagnet.

16. The particle beam therapy system of claim 4, wherein the beam-path changer is a kicker electromagnet.

17. The particle beam therapy system of claim 5, wherein the beam-path changer is a kicker electromagnet.

18. The particle beam therapy system of claim 6, wherein the beam-path changer is a kicker electromagnet.

19. The particle beam therapy system of claim 7, wherein the beam-path changer is a kicker electromagnet.

20. The particle beam therapy system of claim 3, further comprising:
   a beam-path changer control-signal generator comprising a pulse controller, a high-speed switch and a deflector power source;
   wherein the beam-path changer is a beam deflector;
   wherein the pulse controller outputs to the high-speed switch, a control signal generated based on a signal inputted to the beam-path changer control-signal generator; and
   wherein the high-speed switch selects an output voltage of the deflector power source according to the control signal to thereby generate the beam-path changer control signal.

* * * * *